US011759527B2

(12) United States Patent
Boghaert et al.

(10) Patent No.: US 11,759,527 B2
(45) Date of Patent: Sep. 19, 2023

(54) ANTI-EGFR ANTIBODY-DRUG CONJUGATES

(71) Applicant: AbbVie Inc., North Chicago, IL (US)

(72) Inventors: Erwin R. Boghaert, Pleasant Prairie, WI (US); Andrew C. Phillips, Libertyville, IL (US); Andrew J. Souers, Libertyville, IL (US); Kamel Izeradjene, Gurnee, IL (US); John E. Harlan, Lake Zurich, IL (US)

(73) Assignee: AbbVie Inc., North Chicago, IL (US)

( * ) Notice: Subject to any disclaimer, the term of this patent is extended or adjusted under 35 U.S.C. 154(b) by 102 days.

(21) Appl. No.: 17/580,134

(22) Filed: Jan. 20, 2022

(65) Prior Publication Data
US 2022/0226494 A1    Jul. 21, 2022

Related U.S. Application Data

(60) Provisional application No. 63/139,766, filed on Jan. 20, 2021.

(51) Int. Cl.
| | |
|---|---|
| *A61K 47/68* | (2017.01) |
| *C07K 16/28* | (2006.01) |
| *A61P 35/00* | (2006.01) |
| *A61K 39/00* | (2006.01) |

(52) U.S. Cl.
CPC ...... *A61K 47/6849* (2017.08); *A61K 47/6803* (2017.08); *A61P 35/00* (2018.01); *C07K 16/2863* (2013.01); *A61K 2039/505* (2013.01); *C07K 2317/73* (2013.01); *C07K 2317/92* (2013.01)

(58) Field of Classification Search
CPC ............ A61K 47/6849; A61K 47/6803; A61K 2039/505
See application file for complete search history.

(56) References Cited

U.S. PATENT DOCUMENTS

| | | |
|---|---|---|
| 4,399,216 A | 8/1983 | Axel et al. |
| 4,444,887 A | 4/1984 | Hoffmann |
| 4,486,414 A | 12/1984 | Pettit |
| 4,510,245 A | 4/1985 | Cousens et al. |
| 4,526,938 A | 7/1985 | Churchill et al. |
| 4,634,665 A | 1/1987 | Axel et al. |
| 4,676,980 A | 6/1987 | Segal et al. |
| 4,716,111 A | 12/1987 | Osband et al. |
| 4,814,470 A | 3/1989 | Colin et al. |
| 4,816,397 A | 3/1989 | Boss et al. |
| 4,816,444 A | 3/1989 | Pettit et al. |
| 4,816,567 A | 3/1989 | Cabilly et al. |
| 4,879,278 A | 11/1989 | Pettit et al. |
| 4,880,078 A | 11/1989 | Inoue et al. |
| 4,880,935 A | 11/1989 | Thorpe |
| 4,942,184 A | 7/1990 | Haugwitz et al. |
| 4,943,533 A | 7/1990 | Mendelsohn et al. |
| 4,960,790 A | 10/1990 | Stella et al. |
| 4,968,615 A | 11/1990 | Koszinowski et al. |
| 4,978,744 A | 12/1990 | Pettit et al. |
| 4,980,286 A | 12/1990 | Morgan et al. |
| 4,986,988 A | 1/1991 | Pettit et al. |
| 5,076,973 A | 12/1991 | Pettit et al. |
| 5,122,368 A | 6/1992 | Greenfield et al. |
| 5,124,471 A | 6/1992 | Gansow et al. |
| 5,128,326 A | 7/1992 | Balazs et al. |
| 5,138,036 A | 8/1992 | Pettit et al. |
| 5,157,049 A | 10/1992 | Haugwitz et al. |
| 5,168,062 A | 12/1992 | Stinski |
| 5,179,017 A | 1/1993 | Axel et al. |
| 5,208,020 A | 5/1993 | Chari et al. |
| 5,212,290 A | 5/1993 | Vogelstein et al. |
| 5,225,539 A | 7/1993 | Winter |
| 5,278,324 A | 1/1994 | Kingston et al. |
| 5,286,850 A | 2/1994 | Gansoh et al. |
| 5,290,540 A | 3/1994 | Prince et al. |
| 5,362,831 A | 11/1994 | Mongelli et al. |
| 5,380,751 A | 1/1995 | Chen et al. |
| 5,399,363 A | 3/1995 | Liversidge et al. |
| 5,401,828 A | 3/1995 | Vogelstein et al. |
| 5,403,858 A | 4/1995 | Bastard et al. |
| 5,407,683 A | 4/1995 | Shively |
| 5,410,024 A | 4/1995 | Pettit et al. |
| 5,413,923 A | 5/1995 | Kucherlapati et al. |
| 5,415,869 A | 5/1995 | Straubinger et al. |
| 5,424,073 A | 6/1995 | Rahman et al. |
| 5,433,364 A | 7/1995 | Hill et al. |

(Continued)

FOREIGN PATENT DOCUMENTS

| | | |
|---|---|---|
| CN | 102741291 A | 10/2012 |
| EP | 0077671 B1 | 6/1986 |

(Continued)

OTHER PUBLICATIONS

Accession No. NP001774.1, B-cell antigen receptor complex-associated protein alpha chain isoform 1 precursor *Homo sapiens*.
Ammons W.S., et al., "In vitro and in vivo pharmacology and pharmacokinetics of a human engineered monoclonal antibody to epithelial cell adhesion molecule," Neoplasia, 2003, vol. 5 (2), pp. 146-154.
An et al., "Epidermal Growth Factor Receptor (EGFR) and EGFRvIII in Glioblastoma (GBM): Signaling Pathways and Targeted Therapies," Oncogene 37(12):1561-1575, 2018.
Arden., et al., "The Genes Encoding the Receptors for Prolactin and Growth Hormone Map to Human Chromosome 5," The American Journal of Human Genetics—Cell, 1989, vol. 45, p. A129.
Arden K.C., et al., "The Receptors for Prolactin and Growth Hormone are Localized in the Same Region of Human Chromosome 5," Cytogenetic and Cell Genetics, 1990, vol. 53(2-3), pp. 161-165.

(Continued)

*Primary Examiner* — Vanessa L. Ford
*Assistant Examiner* — Sandra Dillahunt
(74) *Attorney, Agent, or Firm* — Glen Gesicki

(57) ABSTRACT

The present disclosure relates to anti-Epidermal Growth Factor Receptor (EGFR) antibody drug conjugates (ADCs) which inhibit Bcl-xL, including compositions and methods using such ADCs, and methods for making such ADCs.

3 Claims, 3 Drawing Sheets

Specification includes a Sequence Listing.

(56) References Cited

U.S. PATENT DOCUMENTS

| | | |
|---|---|---|
| 5,434,287 A | 7/1995 | Gansow et al. |
| 5,438,072 A | 8/1995 | Bobee et al. |
| 5,504,191 A | 4/1996 | Pettit et al. |
| 5,521,284 A | 5/1996 | Pettit et al. |
| 5,530,097 A | 6/1996 | Pettit et al. |
| 5,530,101 A | 6/1996 | Queen et al. |
| 5,545,806 A | 8/1996 | Lonberg et al. |
| 5,554,725 A | 9/1996 | Pettit |
| 5,565,332 A | 10/1996 | Hoogenboom et al. |
| 5,569,825 A | 10/1996 | Lonberg et al. |
| 5,585,089 A | 12/1996 | Queen et al. |
| 5,599,902 A | 2/1997 | Pettit et al. |
| 5,622,929 A | 4/1997 | Willner et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,641,803 A | 6/1997 | Carretta et al. |
| 5,648,260 A | 7/1997 | Winter et al. |
| 5,658,570 A | 8/1997 | Newman et al. |
| 5,661,016 A | 8/1997 | Lonberg et al. |
| 5,663,149 A | 9/1997 | Pettit et al. |
| 5,665,671 A | 9/1997 | Zanin |
| 5,665,860 A | 9/1997 | Pettit et al. |
| 5,679,377 A | 10/1997 | Bernstein et al. |
| 5,681,722 A | 10/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,705,503 A | 1/1998 | Goodall et al. |
| 5,712,374 A | 1/1998 | Kuntsmann et al. |
| 5,714,350 A | 2/1998 | Co et al. |
| 5,714,352 A | 2/1998 | Jakobovits |
| 5,714,586 A | 2/1998 | Kunstmann et al. |
| 5,723,323 A | 3/1998 | Kauffman et al. |
| 5,728,687 A | 3/1998 | Bissery |
| 5,739,116 A | 4/1998 | Hamann et al. |
| 5,750,106 A | 5/1998 | Ostberg |
| 5,763,192 A | 6/1998 | Kauffman et al. |
| 5,766,886 A | 6/1998 | Studnicka et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,773,464 A | 6/1998 | Walker et al. |
| 5,780,588 A | 7/1998 | Pettit et al. |
| 5,795,965 A | 8/1998 | Tsuchiya et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,263 A | 10/1998 | Scola et al. |
| 5,824,514 A | 10/1998 | Kauffman et al. |
| 5,824,805 A | 10/1998 | King et al. |
| 5,840,929 A | 11/1998 | Chen |
| 5,855,913 A | 1/1999 | Hanes et al. |
| 5,869,680 A | 2/1999 | Mas et al. |
| 5,874,064 A | 2/1999 | Edwards et al. |
| 5,877,296 A | 3/1999 | Hamann et al. |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,034,065 A | 3/2000 | Pettit et al. |
| 6,090,382 A | 7/2000 | Salfeld et al. |
| 6,114,598 A | 9/2000 | Kucherlapati et al. |
| 6,180,370 B1 | 1/2001 | Queen et al. |
| 6,204,023 B1 | 3/2001 | Robinson et al. |
| 6,207,418 B1 | 3/2001 | Hori et al. |
| 6,214,345 B1 | 4/2001 | Firestone et al. |
| 6,235,883 B1 | 5/2001 | Jakobovits et al. |
| 6,239,104 B1 | 5/2001 | Pettit et al. |
| 6,323,315 B1 | 11/2001 | Pettit et al. |
| 6,350,861 B1 | 2/2002 | Co et al. |
| 6,410,319 B1 | 6/2002 | Raubitschek et al. |
| 6,441,163 B1 | 8/2002 | Chari et al. |
| 6,660,843 B1 | 12/2003 | Feige et al. |
| 6,867,187 B2 | 3/2005 | Clevenger et al. |
| 6,913,748 B2 | 7/2005 | Widdison |
| 7,223,837 B2 | 5/2007 | De Groot et al. |
| 7,227,002 B1 | 6/2007 | Kufer et al. |
| 7,263,946 B2 | 9/2007 | Worthy et al. |
| 7,422,899 B2 | 9/2008 | Elenbaas et al. |
| 7,447,597 B2 | 11/2008 | Wang et al. |
| 7,507,716 B2 | 3/2009 | Diogenes et al. |
| 7,521,541 B2 | 4/2009 | Eigenbrot et al. |
| 7,589,180 B2 | 9/2009 | Old et al. |
| 7,598,028 B2 | 10/2009 | Macoska |
| 7,612,181 B2 | 11/2009 | Wu et al. |
| 7,723,270 B1 | 5/2010 | McCafferty et al. |
| 7,741,319 B2 | 6/2010 | Howard et al. |
| 7,767,792 B2 | 8/2010 | Johns et al. |
| 7,855,275 B2 | 12/2010 | Eigenbrot et al. |
| 7,867,493 B2 | 1/2011 | Damiano et al. |
| 7,989,434 B2 | 8/2011 | Feng |
| 7,994,135 B2 | 8/2011 | Doronina et al. |
| 8,039,273 B2 | 10/2011 | Jeffrey et al. |
| 8,142,784 B2 | 3/2012 | Ebens, Jr. et al. |
| 8,187,836 B2 | 5/2012 | Hsieh |
| 8,236,319 B2 | 8/2012 | Chari et al. |
| 8,301,397 B2 | 10/2012 | Bertoncini et al. |
| 8,309,093 B2 | 11/2012 | Gudas et al. |
| 8,349,308 B2 | 1/2013 | Yurkovetskiy et al. |
| 8,389,282 B2 | 3/2013 | Sadelain et al. |
| 8,399,512 B2 | 3/2013 | Akullian et al. |
| 8,455,219 B2 | 6/2013 | Hsieh |
| 8,455,622 B2 | 6/2013 | McDonagh et al. |
| 8,524,214 B2 | 9/2013 | Yurkovetskiy et al. |
| 8,535,678 B2 | 9/2013 | Law et al. |
| 8,568,728 B2 | 10/2013 | Jeffrey |
| 8,648,046 B2 | 2/2014 | Chen |
| 8,754,035 B2 | 6/2014 | Chen |
| 8,809,051 B2 | 8/2014 | Jakobovits et al. |
| 8,809,151 B2 | 8/2014 | Flachowsky et al. |
| 8,822,647 B2 | 9/2014 | Jensen |
| 8,883,979 B2 | 11/2014 | Ma et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,072,798 B2 | 7/2015 | Ritter et al. |
| 9,105,939 B2 | 8/2015 | Matsuyama et al. |
| 9,109,630 B2 | 8/2015 | Misada |
| 9,401,234 B2 | 7/2016 | Tseng et al. |
| 9,428,082 B2 | 8/2016 | Hotary et al. |
| 9,493,568 B2 | 11/2016 | Reilly et al. |
| 9,562,102 B2 | 2/2017 | Old et al. |
| 9,618,978 B2 | 4/2017 | Sip |
| 9,649,374 B2 | 5/2017 | Otto et al. |
| 9,827,330 B2 | 11/2017 | Reilly et al. |
| 10,098,968 B2 | 10/2018 | Reilly et al. |
| 10,112,999 B2 | 10/2018 | Reilly et al. |
| 10,184,003 B2 | 1/2019 | Anderson et al. |
| 10,640,563 B2 | 5/2020 | Benatuil et al. |
| 2002/0137134 A1 | 9/2002 | Gerngross |
| 2003/0054497 A1 | 3/2003 | Co et al. |
| 2003/0083263 A1 | 5/2003 | Doronina et al. |
| 2004/0018590 A1 | 1/2004 | Gerngross et al. |
| 2004/0028687 A1 | 2/2004 | Waelti |
| 2005/0009751 A1 | 1/2005 | Senter et al. |
| 2005/0042664 A1 | 2/2005 | Wu et al. |
| 2005/0123536 A1 | 6/2005 | Law et al. |
| 2005/0180972 A1 | 8/2005 | Wahl et al. |
| 2005/0238649 A1 | 10/2005 | Doronina et al. |
| 2005/0271615 A1 | 12/2005 | Shabat et al. |
| 2006/0024317 A1 | 2/2006 | Boyd et al. |

(56) References Cited

U.S. PATENT DOCUMENTS

| | | | |
|---|---|---|---|
| 2006/0074008 A1 | 4/2006 | Senter et al. | |
| 2006/0104968 A1 | 5/2006 | Bookbinder et al. | |
| 2006/0116422 A1 | 6/2006 | De Groot et al. | |
| 2006/0134709 A1 | 6/2006 | Stavenhagen et al. | |
| 2007/0173497 A1 | 7/2007 | Howard et al. | |
| 2007/0269438 A1 | 11/2007 | Elenbaas et al. | |
| 2007/0280931 A1 | 12/2007 | Chen et al. | |
| 2009/0220510 A1 | 9/2009 | Old et al. | |
| 2009/0285757 A1 | 11/2009 | Khaw | |
| 2009/0318668 A1 | 12/2009 | Beusker et al. | |
| 2010/0056762 A1 | 3/2010 | Old | |
| 2010/0092475 A1 | 4/2010 | Johns et al. | |
| 2010/0129314 A1 | 5/2010 | Singh et al. | |
| 2010/0152725 A1 | 6/2010 | Pearson et al. | |
| 2010/0166744 A1 | 7/2010 | Wong | |
| 2010/0322937 A1 | 12/2010 | Johns et al. | |
| 2011/0076232 A1 | 3/2011 | Old et al. | |
| 2011/0150759 A1 | 6/2011 | Johns et al. | |
| 2011/0150760 A1 | 6/2011 | Damiano et al. | |
| 2011/0217363 A1 | 9/2011 | Chen | |
| 2011/0313230 A1 | 12/2011 | Johns et al. | |
| 2012/0107332 A1 | 5/2012 | Jeffrey | |
| 2012/0183471 A1 | 7/2012 | Old et al. | |
| 2012/0294796 A1 | 11/2012 | Johnson et al. | |
| 2012/0315276 A1 | 12/2012 | Otto et al. | |
| 2012/0321632 A1 | 12/2012 | Otto et al. | |
| 2013/0022606 A1 | 1/2013 | Otto et al. | |
| 2013/0028917 A1 | 1/2013 | Howard et al. | |
| 2013/0028919 A1 | 1/2013 | Howard et al. | |
| 2013/0117871 A1 | 5/2013 | Kucherlapati et al. | |
| 2013/0118921 A1 | 5/2013 | Harding et al. | |
| 2013/0129739 A1 | 5/2013 | Ottto et al. | |
| 2013/0171147 A1 | 7/2013 | Otto et al. | |
| 2013/0189218 A1 | 7/2013 | Akullian et al. | |
| 2013/0224228 A1 | 8/2013 | Jackson et al. | |
| 2013/0266573 A1 | 10/2013 | Old et al. | |
| 2013/0272968 A1 | 10/2013 | Otto et al. | |
| 2013/0303509 A1 | 11/2013 | Hansen et al. | |
| 2013/0309256 A1 | 11/2013 | Lyon et al. | |
| 2014/0017265 A1 | 1/2014 | Yurkovetskiy et al. | |
| 2014/0032227 A1 | 1/2014 | Zopf et al. | |
| 2014/0227294 A1 | 8/2014 | Anderson et al. | |
| 2014/0286968 A1 | 9/2014 | Leanna et al. | |
| 2014/0286969 A1 | 9/2014 | Tschoepe et al. | |
| 2014/0322130 A1 | 10/2014 | Scott et al. | |
| 2014/0322275 A1 | 10/2014 | Brogdon et al. | |
| 2014/0328750 A1 | 11/2014 | Johnson et al. | |
| 2015/0337042 A1 | 11/2015 | Reilly et al. | |
| 2016/0009807 A1 | 1/2016 | Govindappa et al. | |
| 2016/0158377 A1 | 6/2016 | Ackler et al. | |
| 2016/0185858 A1 | 6/2016 | Smith et al. | |
| 2016/0339117 A1 | 11/2016 | Ackler et al. | |
| 2017/0182179 A1 | 6/2017 | Ackler et al. | |
| 2019/0010237 A1 | 1/2019 | Reilly et al. | |
| 2019/0134216 A1 | 5/2019 | Reilly et al. | |
| 2019/0142941 A1 | 5/2019 | Ackler et al. | |
| 2019/0153107 A1 | 5/2019 | Boghaert et al. | |
| 2019/0153108 A1 | 5/2019 | Boghaert et al. | |
| 2019/0343961 A1 | 11/2019 | Boghaert et al. | |
| 2020/0188525 A1 | 6/2020 | Reilly et al. | |
| 2020/0239553 A1 | 7/2020 | Ackler et al. | |
| 2020/0246323 A1 | 8/2020 | Ackler et al. | |
| 2020/0246460 A1 | 8/2020 | Ackler et al. | |
| 2020/0297863 A1 | 9/2020 | Reilly et al. | |
| 2020/0405878 A1 | 12/2020 | Reilly et al. | |
| 2021/0171637 A1 | 6/2021 | Benatuil et al. | |

FOREIGN PATENT DOCUMENTS

| | | | |
|---|---|---|---|
| EP | 0229246 B1 | 8/1993 | |
| EP | 0239400 B1 | 8/1994 | |
| EP | 1176195 A1 | 1/2002 | |
| EP | 0592106 B1 | 11/2004 | |
| EP | 0519596 B1 | 2/2005 | |
| EP | 1800695 A1 | 6/2007 | |
| EP | 2530089 A1 | 12/2012 | |
| EP | 1176195 B1 | 5/2013 | |
| EP | 3148592 A2 | 4/2017 | |
| GB | 8901334 | 5/1990 | |
| GB | 9101134 | 1/1992 | |
| GB | 9201755 | 4/1993 | |
| JP | 2010501163 A | 1/2010 | |
| JP | 2019521114 A | 7/2019 | |
| WO | WO-8912624 A2 | 12/1989 | |
| WO | WO-9005144 A1 | 5/1990 | |
| WO | WO-9005370 A1 | 5/1990 | |
| WO | WO-9014424 A1 | 11/1990 | |
| WO | WO-9014430 A1 | 11/1990 | |
| WO | WO-9014443 A1 | 11/1990 | |
| WO | WO-9103489 A1 | 3/1991 | |
| WO | WO-9105548 A1 | 5/1991 | |
| WO | WO-9109967 A1 | 7/1991 | |
| WO | WO-9116350 A1 | 10/1991 | |
| WO | WO-9201047 A1 | 1/1992 | |
| WO | WO-9203461 A1 | 3/1992 | |
| WO | WO-9211272 A1 | 7/1992 | |
| WO | WO-9219244 A2 | 11/1992 | |
| WO | WO-9222332 A2 | 12/1992 | |
| WO | WO-9306213 A1 | 4/1993 | |
| WO | WO-9321232 A1 | 10/1993 | |
| WO | WO-9416729 A1 | 8/1994 | |
| WO | WO-9418219 A1 | 8/1994 | |
| WO | WO-9515770 A1 | 6/1995 | |
| WO | WO-9616988 A1 | 6/1996 | |
| WO | WO-9620698 A2 | 7/1996 | |
| WO | WO-9720032 A1 | 6/1997 | |
| WO | WO-9729131 A1 | 8/1997 | |
| WO | WO-9731655 A2 | 9/1997 | |
| WO | WO-9732572 A2 | 9/1997 | |
| WO | WO-9744013 A1 | 11/1997 | |
| WO | WO-9822451 A1 | 5/1998 | |
| WO | WO-9828288 A1 | 7/1998 | |
| WO | WO-9831346 A1 | 7/1998 | |
| WO | WO-9835704 A1 | 8/1998 | |
| WO | WO-9906834 A2 | 2/1999 | |
| WO | WO-9909021 A1 | 2/1999 | |
| WO | WO-9914209 A1 | 3/1999 | |
| WO | WO-9915154 A1 | 4/1999 | |
| WO | WO-9918113 A1 | 4/1999 | |
| WO | WO-9919500 A1 | 4/1999 | |
| WO | WO-9920253 A1 | 4/1999 | |
| WO | WO-9925044 A1 | 5/1999 | |
| WO | WO-9954342 A1 | 10/1999 | |
| WO | WO-9966903 A2 | 12/1999 | |
| WO | WO-0109785 A1 | 2/2001 | |
| WO | WO-0190198 A1 | 11/2001 | |
| WO | WO-02088172 A2 | 11/2002 | |
| WO | WO-02092771 A2 | 11/2002 | |
| WO | WO-03016466 A2 | 2/2003 | |
| WO | WO-03035835 A2 | 5/2003 | |
| WO | WO-03093793 A2 | 11/2003 | |
| WO | WO-2004010957 A2 | 2/2004 | |
| WO | WO-2004050016 A2 | 6/2004 | |
| WO | WO-2004078140 A2 | 9/2004 | |
| WO | WO-2005081854 A2 | 9/2005 | |
| WO | WO-2005081898 A2 | 9/2005 | |
| WO | WO-2005100584 A2 | 10/2005 | |
| WO | WO-2005123780 A2 | 12/2005 | |
| WO | WO-2006042146 A2 | 4/2006 | |
| WO | WO-2006083562 A2 | 8/2006 | |
| WO | WO-2006089668 A1 | 8/2006 | |
| WO | WO-2006111759 A1 | 10/2006 | |
| WO | WO-2006129623 A1 | 12/2006 | |
| WO | WO-2007080392 A2 | 7/2007 | |
| WO | WO-2007150020 A1 | 12/2007 | |
| WO | WO-2008017828 A2 | 2/2008 | |
| WO | WO-2008022295 A2 | 2/2008 | |
| WO | WO-2008033495 A2 | 3/2008 | |
| WO | WO-2008091701 A2 | 7/2008 | |
| WO | WO-2008097866 A2 | 8/2008 | |
| WO | WO-2008097870 A2 | 8/2008 | |
| WO | WO-2008100624 A2 | 8/2008 | |
| WO | WO-2008103947 A2 | 8/2008 | |
| WO | WO-2008103953 A2 | 8/2008 | |

(56) References Cited

FOREIGN PATENT DOCUMENTS

| | | |
|---|---|---|
| WO | WO-2008115404 A1 | 9/2008 |
| WO | WO-2008135237 A1 | 11/2008 |
| WO | WO-2009023265 A1 | 2/2009 |
| WO | WO-2009134776 A2 | 11/2009 |
| WO | WO-2009134952 A2 | 11/2009 |
| WO | WO-2009134976 A1 | 11/2009 |
| WO | WO-2010080503 A1 | 7/2010 |
| WO | WO-2010096434 A2 | 8/2010 |
| WO | WO-2010111198 A1 | 9/2010 |
| WO | WO-2011000370 A1 | 1/2011 |
| WO | WO-2011057216 A1 | 5/2011 |
| WO | WO-2011058321 A1 | 5/2011 |
| WO | WO-2011069795 A1 | 6/2011 |
| WO | WO-2011069796 A1 | 6/2011 |
| WO | WO-2011069797 A1 | 6/2011 |
| WO | WO-2011069798 A1 | 6/2011 |
| WO | WO-2011109400 A2 | 9/2011 |
| WO | WO-2011130598 A1 | 10/2011 |
| WO | WO-2011151405 A1 | 12/2011 |
| WO | WO-2011161031 A1 | 12/2011 |
| WO | WO-2012027494 A1 | 3/2012 |
| WO | WO-2012075383 A2 | 6/2012 |
| WO | WO-2012135360 A1 | 10/2012 |
| WO | WO-2012136519 A1 | 10/2012 |
| WO | WO-2012151512 A2 | 11/2012 |
| WO | WO-2012163932 A1 | 12/2012 |
| WO | WO-2013055897 A1 | 4/2013 |
| WO | WO-2013078377 A1 | 5/2013 |
| WO | WO-2013173337 A2 | 11/2013 |
| WO | WO-2014093379 A1 | 6/2014 |
| WO | WO-2014093394 A1 | 6/2014 |
| WO | WO-2014093640 A1 | 6/2014 |
| WO | WO-2014093786 A1 | 6/2014 |
| WO | WO-2014100762 A1 | 6/2014 |
| WO | WO-2014139324 A1 | 9/2014 |
| WO | WO-2014143765 A1 | 9/2014 |
| WO | WO-2014152199 A1 | 9/2014 |
| WO | WO-2014153002 A1 | 9/2014 |
| WO | WO-2015026907 A1 | 2/2015 |
| WO | WO-2015057852 A1 | 4/2015 |
| WO | WO-2015143382 A1 | 9/2015 |
| WO | WO-2015146132 A1 | 10/2015 |
| WO | WO-2015157595 A1 | 10/2015 |
| WO | WO-2016064749 A2 | 4/2016 |
| WO | WO-2016094505 A1 | 6/2016 |
| WO | WO-2016094509 A1 | 6/2016 |
| WO | WO-2016094517 A1 | 6/2016 |
| WO | WO-2017096163 A1 | 6/2017 |
| WO | WO-2017214233 A1 * | 12/2017 ............ A61K 47/65 |
| WO | WO-2017214282 A1 | 12/2017 |
| WO | WO-2017214301 A1 | 12/2017 |
| WO | WO-2017214322 A1 | 12/2017 |
| WO | WO-2017214339 A1 | 12/2017 |
| WO | WO-2017214456 A1 | 12/2017 |
| WO | WO-2017214458 A2 | 12/2017 |
| WO | WO-2017214462 A2 | 12/2017 |

OTHER PUBLICATIONS

Ausubel, et al., Current Protocols in Molecular Biology, 1993, 6.3.1-6.3.6,2.10.1-2.10.1-2.10.16.
Ausubel F.M., et al., "A Compendium of Methods from Current Protocols in Molecular Biology," in: Short Protocols in Molecular Biology, John Wiely & Sons, 1989.
Bauernhofer T., et al., "Prolactin Receptor is A Negative Prognostic Factor in Patients with Squamous Cell Carcinoma of the Head and Neck," British Journal of Cancer, 2011, vol. 104(10), pp. 1641-1648.
Boghaert E.R., et al., "Tumoricidal Effect of Calicheamicin Immunoconjugates Using a Passive Targeting Strategy," International Journal of Oncology, 2006, vol. 28 (3), pp. 675-684.
Boutin J.M., et al., "Identification of a CDNA Encoding a Long Form of Prolactin Receptor in Human Hepatoma and Breast Cancer Cells," Molecular endocrinology, 1989, vol. 3(9), pp. 1455-1461.
Chen J., et al., "The Bcl-2/Bcl-XL/Bcl-w inhibitor, navitoclax, enhances the activity of chemotherapeutic agents in vitro and in vivo," Molecular Cancer Therapeutics, 2011, vol. 10 (12), pp. 2340-2349.
Competitive Inhibition, Internet Citation [online], Sep. 13, 2011 [retrieved on Oct. 3, 2011], Retrieved from the Internet: https://en.wikipedia.org/wiki/Competitive_inhibition, 4 pages.
Damiano J.S., et al., "Molecular Pathways: Blockade of the PRLR Signaling Pathway as a Novel Antihormonal Approach forthe Treatment of Breast and Prostate Cancer," Clinical Cancer Research, Apr. 2013, vol. 19(7), pp. 1644-1650.
Damiano J.S., et al., "Neutralization of Prolactin Receptor Function by Monoclonal Antibody Lfa102 a Novel Potential Therapeutic for the Treatment of Breast Cancer," Molecular Cancer Therapeutics, 2013, vol. 12 (3), pp. 295-305.
Database Caplus Chemical Abstracts Service, Columbus, Ohio, US; Database Registry No. 159857-80-4, Entered STN: Dec. 30, 1994.
Doronina S.O., et al., "Novel Peptide Linkers for Highly Potent Antibody-auristatin Conjugate," Bioconjugate Chemistry, Oct. 2008, vol. 19 (10), pp. 1960-1963.
Extended European Search Report EP18152359.8 dated May 24, 2018.
Galsgaard E.D., et al., "Re-evaluation of the Prolactin Receptor Expression in Human Breast Cancer," Journal of Endocrinology, 2009, vol. 201 (1), pp. 115-128.
Gennaro A.R., ed., Remington, The Science and Practice of Pharmacy, 19th Edition, Mack Publishing, 1995, Table of Contents.
Gill S., et al., "Expression of Prolactin Receptors in Normal, Benign, and Malignant Breast Tissue: an Immunohistological Study," Journal of clinical pathology, 2001, vol. 54 (12), pp. 956-960.
Gussow D., et al., "Humanization of Monoclonal Antibodies," Methods in Enzymology, 1991, vol. 203, pp. 99-121.
Harbaum L., et al., "Clinicopathological Significance of Prolactin Receptor Expression in Colorectal Carcinoma and Corresponding Metastases," Modern Pathology : An Official Journal of The United States and Canadian Academy of Pathology, Inc, 2010, vol. 23 (7), pp. 961-971.
Henry M.D., et al., "A Prostate-Specific Membrane Antigen-Targeted Monoclonal Antibody-Chemotherapeutic Conjugate Designed forthe Treatment of Prostate Cancer," Cancer Research, 2004, vol. 64, pp. 7995-8001.
Herbst R.S., et al., "IMC-C225, An Anti-Epidermal Growth Factor Receptor Monoclonal Antibody, for Treatment of Head and Neck Cancer," Expert Opinion on Biological, 2001, vol. 1 (4), pp. 719-732.
International Preliminary Report on Patentability for Application No. PCT/US2013/077452, dated Mar. 31, 2015.
International Preliminary Report on Patentability from PCT/US2017/036399, dated Dec. 11, 2018, 7 pages.
International Search Report and Written Opinion for Application No. PCT/US2013/077452, dated May 8, 2014.
International Search Report and Written Opinion for Application No. PCT/US2018/049412, dated Nov. 26, 2018, 9 pages.
Janeway C.A., "The Structure of a Typical Antibody Molecule," Immunobiology, vol. 5, Garland Publishing, New York, 2001.
Johns et al., "The antitumor monoclonal antibody 806 recognizes a high-mannose form of the EGF receptor that reaches the cell surface when cells over-express the receptor" FASEB J. (2005) 1-18, 19(3).
Jung S., et al., "Improving in Vivo Folding and Stability of a Single-Chain Fv Antibody Fragment by Loop Grafting," Protein Engineering, 1997, vol. 10 (8), pp. 959-966.
Leav I., et al., "Prolactin Receptor Expression in the Developing Human Prostate and in Hyperplastic, Dysplastic, and Neoplastic Lesions," The American Journal of Pathology, 1999, vol. 154 (3), pp. 863-870.
Levina V.V., et al., "Biological Significance of Prolactin in Gynecologic Cancers," Cancer Research, 2009, vol. 69 (12), pp. 5226-5233.
Li H., et al., "Activation of Signal Transducer and Activator of Transcription 5 in Human Prostate Cancer is Associated with High Histological Grade," Cancer research, 2004, vol. 64 (14), pp. 4774-4782.

(56) References Cited

OTHER PUBLICATIONS

Ling C., et al., "Identification of Functional Prolactin (PRL) Receptor Gene Expression: PRL Inhibits Lipoprotein Lipase Activity in Human White Adipose Tissue," The Journal of Clinical Endocrinology & Metabolism, Apr. 2003, vol. 88 (4), pp. 1804-1808.
Lynch D.H., et al., "Therapeutic Potential of ABX-EGF: A Fully Human Anti-Epidermal Growth Factor Receptor Monoclonal Antibody for Cancer Treatment," Seminars in Oncology, 2002, vol. 29 (1), pp. 47-50.
Martei Y.M., et al., "Identifying Patients at High Risk of Breast Cancer Recurrence: Strategies to Improve Patient Outcomes," Breast Cancer, Oct. 2015, vol. 7, pp. 337-343.
Mendelsohn J., et al., "Epidermal Growth Factor Receptor Targeting in Cancer," Seminars in Oncology, 2006, vol. 33 (4), pp. 369-385.
Mullard A., "Maturing Antibody-Drug Conjugate Pipeline Hits 30," Nature Reviews Drug Discovery, 2013, vol. 12(5), pp. 329-332.
Perez E.A., "Microtubule Inhibitors: Differentiating Tubulin-inhibiting Agents Based on Mechanisms of Action, Clinical Activity, and Resistance," Molecular Cancer Therapeutics, Aug. 2009, vol. 8 (8), pp. 2086-2095.
Remington's Pharmaceutical Sciences, Alfonso R.D., eds., Mack Publishing Co., 1980, Table of Contents.
Rutkowska., et al., "EGFRvIII: An Oncogene with Ambiguous Role," Journal of Oncology vol. 2019, pp. 1-20, 2019.
Ryan J., et al., "BH3 Profiling in Whole Cells by Fluorimeter or FACS," Methods, 2013, vol. 61 (2), pp. 156-164.
Sambrook J., et al., "Expression of Cloned Genes in *Escherichia coli*," in: Molecular Cloning: A Laboratory Manual, Second Edition, TOC, Cold Spring Harbor Laboratory Press, 1989.
Sambrook J., et al., "Molecular Cloning," A Laboratory Manual, Second Edition, Cold Spring Harbor Laboratory Press, 1989, Table of Contents.
Shinkawa T., et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, 2003, vol. 278 (5), pp. 3466-3473.
Singapore Search Report for Application No. 11201704710P, dated Apr. 18, 2018, 4 pages.
Singapore Written Opinion for Application No. 11201704710P, dated Apr. 23, 2018, 10 pages.
Sissom J.F., et al., "Anti-Growth Action on Mouse Mammary and Prostate Glands of a Monoclonal Antibody to Prolactin Receptor," The American journal of pathology, 1988, vol. 133 (3), pp. 589-595.
Touraine P., et al., "Increased Expression of Prolactin Receptor Gene Assessed by Quantitative Polymerase Chain Reaction in Human Breast Tumors Versus Normal Breast Tissues," The Journal of clinical endocrinology and metabolism, 1998, vol. 83 (2), pp. 667-674.
Tworoger S.S., et al., "Association Between Plasma Prolactin Concentrations and Risk of Breast Cancer Among Predominately Premenopausal Women," Cancer research, 2006, vol. 66 (4), pp. 2476-2482.
Tworoger S.S., et al., "Plasma Prolactin Concentrations and Risk of Postmenopausal Breast Cancer," Cancer research, 2004, vol. 64 (18), pp. 6814-6819.
Van Agthoven J., et al., "Structural Characterization of the Stem-Stem Dimerization Interface between Prolactin Receptor Chains Complexed with the Natural Hormone," Journal of Molecular Biology, 2010, vol. 404 (1), pp. 112-126.
Wennbo H., et al., "Activation of the Prolactin Receptor But Not the Growth Hormone Receptor is Important for Induction of Mammary Tumors in Transgenic Mice," The Journal of clinical investigation, 1997, vol. 100 (11), pp. 2744-2751.
Wennbo H., et al., "Transgenic Mice Overexpressing the Prolactin Gene Develop Dramatic Enlargement of the Prostate Gland," Endocrinology, 1997, vol. 138 (10), pp. 4410-4415.
Xu X., et al., "A Molecular Mimic of Phosphorylated Prolactin Markedly Reduced Tumor Incidence and Size When Du145 Human Prostate Cancer Cells Were Grown in Nude Mice," Cancer research, 2001, vol. 61 (16), pp. 6098-6104.
Yazaki P.J., et al., "Humanization of the Anti-Cea T84.66 Antibody Based on Crystal Structure Data," Protein Engineering, Design and Selection, 2004, vol. 17 (5), pp. 481-489.
A Study Evaluating Safety and Pharmacokinetics of ABBV-221 in Subjects With Advanced Solid Tumor Types Likely to Exhibit Elevated Levels of Epidermal Growth Factor Receptor, NCT02365662, 2015.
Ahmed M., et al., "Humanized Affinity-Matured Monoclonal Antibody 8h9 Has Potent Antitumor Activity and Binds to FG Loop of Tumor Antigen B7-H3," The Journal of Biological Chemistry, 2015, vol. 290 (50), pp. 30018-30029.
Alley S.C., et al., "Contribution of Linker Stability to the Activities of Anticancer Immunoconjugates," Bioconjugate Chemistry, 2008, vol. 19 (3), pp. 759-765.
Amir R.J., et al., "Self-lmmolative Dendrimers," Angew. Chem. (International Ed. In English), 2003, vol. 42 (37), pp. 4494-4499.
Amsberry K.L., et al., "The Lactonization of 2'-hydroxyhydrocinnamic Acid Amides: A Potential Prodrug for Amines," The Journal of Organic Chemistry, 1990, vol. 55 (23), pp. 5867-5877.
Amundson S.A., et al., "An Informatics Approach Identifying Markers of Chemosensitivity in Human Cancer Cell Lines," Cancer Research, 2000, vol. 60 (21), pp. 6101-6110.
Arnon R., et al., "Monoclonal Antibodies for Immunotargeting of Drugs in Cancer Therapy," Monoclonal Antibodies and Cancer Therapy, Alan R. Liss, Inc., 1985, pp. 243-256.
Atalay G., et al., "Novel Therapeutic Strategies Targeting the Epidermal Growth Factor Receptor (EGFR) Family and its Downstream Effectors in Breast Cancer," Annals of Oncology, 2003, vol. 14 (9), pp. 1346-1363.
Ausubel et al., "Current Protocols in Molecular Biology," John Wiley &Sons, NY, 1993.
Ausubel F.M., et al., eds., Current Protocols in Molecular Biology, vol. 1, Green Publishing Associates, Inc., and John Wiley & Sons, Inc., 1993, pp. 6.3.1-6.3.6 and 2.10.3.
Axup J.Y., et al., "Synthesis of Site-Specific Antibody-Drug Conjugates Using Unnatural Amino Acids," Proceedings of the National Academy of Sciences of the United States of America, 2012, vol. 109 (40), pp. 16101-16106.
Badescu G., et al., "Bridging Disulfides for Stable and Defined Antibody Drug Conjugates," Bioconjugate Chemistry, 2014, vol. 25 (6), pp. 1124-1136.
Baldwin R.W., et al., Monoclonal Antibodies for Cancer Detection and Therapy, London Academic Press, 1985, pp. 159-179.
Banerjee C., et al., "BET Bromodomain Inhibition as a Novel Strategy for Reactivation of HIV-1," Journal of Leukocyte Biology, 2012, vol. 92 (6), pp. 1147-1154.
Baselga J., et al., "Phase I Studies of Anti-Epidermal Growth Factor ReceptorChimeric Antibody C225 alone and in Combination with Cisplatin," Journal of Clinical Oncology, 2000, vol. 18(4), pp. 904-914.
Baselga J., et al., "Phase II Study of Weekly Intravenous Recombinant Humanized Anti-P185her2 Monoclonal Antibody in Patients with Her2/Neu-Overexpressing Metastatic Breast Cancer," Journal of Clinical Oncology, 1996, vol. 14 (3), pp. 737-744.
Baselga J., "The EGFR as a Target for Anticancer Therapy—focus on Cetuximab," European Journal of Cancer, 2001, vol. 37 (Suppl. 4), pp. S16-S22.
Batra S.K., et al., "Epidermal Growth Factor Ligand-Independent, Unregulated, Cell-Transforming Potential of a Naturally Occurring Human Mutant EGFRvIII Gene," Cell Growth and Differentiation, 1995, vol. 6 (10), pp. 1251-1259.
Benatuil L., et al., "An Improved Yeast Transformation Method for the Generation of Very Large Human Antibody Libraries," Protein Engineering, Design and Selection, 2010, vol. 23 (4), pp. 155-159.
Berge S.M., et al., "Pharmaceutical Salts," Journal of Pharmaceutical Sciences, 1977, vol. 66 (1), pp. 1-19.
Bird R.E., et al., "Single-Chain Antigen-Binding Proteins," Science, 1988, vol. 242 (4877), pp. 423-426.
Boger D.L., et al., "CC-1065 and the Duocarmycins: Unraveling the Keys to a New Class of Naturally Derived DNA Alkylating Agents,"

(56) References Cited

OTHER PUBLICATIONS

Proceedings of the National Academy of Sciences of the United States of America, 1995, vol. 92 (9), pp. 3642-3649.
Boger D.L., et al., "Design, Synthesis, and Evaluation of DNA Minor Groove Binding Agents," Pure and Applied Chemistry, 1993, vol. 65 (6), pp. 1123-1132.
Boland W., et al., "The Emerging Role of Nimotuzumab in the Treatment of Non-Small Cell Lung Cancer," Biologies, 2010, vol. 4, pp. 289-298.
Bostrom J., et al., "Variants of the Antibody Herceptin That Interact with HER2 and VEGF at the Antigen Binding Site," Science, 2009, vol. 323 (5921), pp. 1610-1614.
Bouchier-Hayes L., et al., "Measuring Apoptosis at the Single Cell Level," Methods, 2008, vol. 44 (3), pp. 222-228.
Boyer C.M., et al., "Relative Cytotoxic Activity of Immunotoxins Reactive with Different Epitopes on the Extracellular Domain of the c-ErbB-2 (HER-2/neu) Gene Product p185," International Journal of Cancer, 1999, vol. 82, pp. 525-531.
Brown H.C., et al., "Hydroboration. XVIII. The Reaction of Diisopinocampheylborane with Representative cis-Acyclic, Cyclic, and Bicyclic Olefins. A Convenient Synthesis of Optically Active Alcohols and Olefins of High Optical Purity and Established Configuration," Journal of the American Chemical Society, 1964, vol. 86 (3), pp. 397-403.
Buchwald H., et al., "Long-Term, Continuous Intravenous Heparin Administration by an Implantable Infusion Pump in Ambulatory Patients with Recurrent Venous Thrombosis," Surgery, 1980, vol. 88 (4), pp. 507-516.
Burke P.J., et al., "Design, Synthesis, and Biological Evaluation of Antibody-Drug Conjugates Comprised of Potent Camptothecin Analogues," Bioconjugate Chemistry, 2009, vol. 20 (6), pp. 1242-1250.
Buss J.E., et al., "Altered Epidermal Growth Factor (EGF)-Stimulated Protein Kinase Activity in Variant A431 cells with Altered Growth Responses to EGF," Proceedings of the National Academy of Sciences, 1982, vol. 79 (8), pp. 2574-2578.
Cai S., et al., "CD98 Modulates Integrin Beta1 Function in Polarized Epithelial Cells," Journal of Cell Science, 2005, vol. 118 (Pt 5), pp. 889-899.
Caldas C., et al., "Humanization of the Anti-CD18 Antibody 6.7: an Unexpected Effect of a Framework Residue in Binding to Antigen," Molecular Immunology, 2003, vol. 39 (15), pp. 941-952.
Campos C.B., et al., "Method for Monitoring of Mitochondrial Cytochrome C Release During Cell Death: Immunodetection of Cytochrome C by Flow Cytometry After Selective Permeabilization of the Plasma Membrane," Cytometry, 2006, vol. 69 (6), pp. 515-523.
Canfield S.M., et al., "The Binding Affinity of Human IgG for its High Affinity Fc Receptor is Determined by Multiple Amino Acids in the CH2 Domain and is Modulated by the Hinge Region," The Journal of Experimental Medicine, 1991, vol. 173(6), pp. 1483-1491.
Cantor J.M., et al., "CD98 at the Crossroads of Adaptive Immunity and Cancer," Journal of Cell Science, Mar. 2012, vol. 125 (Pt 6), pp. 1373-1382.
Carter P., et al., "Humanization of an Anti-p185 HER2 Antibody for Human Cancer Therapy," Proceedings of the National Academy of Sciences of the United States of America, 1992, vol. 89 (10), pp. 4285-4289.
Casset F., et al., "A Peptie Mimetic of an Anti-CD4 Monoclonal Antibody by Rational Design," Biochemical and Biophysical Research Communications, 2003, vol. 307 (1), pp. 198-205.
Chao G., "Characterizing and Engineering Antibodies Against the Epidermal Growth Factor Receptor (Project Report)," in: Doctor of Philosophy in Chemical Enginering, 2008, pp. 53-54.
Chao G., et al., "Fine Epitope Mapping of Anti-Epidermal Growth Factor Receptor Antibodies through Random Mutagenesis and Yeast Surface Display," Journal of Molecular Biology, 2004, vol. 342 (2), pp. 539-550.

Chao G., et al., "Isolating and Engineering Human Antibodies Using Yeast Surface Display," Nature Protocols, 2006, vol. 1 (2), pp. 755-768.
Chapoval A. I., et al., "B7-H3: A Costimulatory Molecule for T Cell Activation and IFN-gamma Production," Nature Immunology, 2001, vol. 2 (3), pp. 269-274.
Chari R.V., et al., "Immunoconjugates Containing Novel Maytansinoids: Promising Anticancer Drugs," Cancer Research, 1992, vol. 52 (1), pp. 127-131.
Chari R.V., et al., "Targeted Cancer Therapy: Conferring Specificity to Cytotoxic Drugs," Accounts of Chemical Research, 2008, vol. 41 (1), pp. 98-107.
Chien N.C., et al., "Significant Structural and Functional Change of an Antigen-Binding Site by a Distant Amino Acid Substitution: Proposal of a Structural Mechanism," The Proceedings of the National Academy of Sciences, 1989, vol. 86 (14), pp. 5532-5536.
Chothia C., et al., "Canonical Structures for the Hypervariable Regions of Immunoglobulins," Journall of Molecular Biology, 1987, vol. 196 (4), pp. 901-917.
Chothia C., et al., "Conformations of Immunoglobulin Hypervariable Regions," Nature, 1989, vol. 342 (6252), pp. 877-883.
Chu., et al., Biochemia No. 2, 2001, Roche Molecular Biologicals.
Cleary J.M., et al., "A Phase 1 Study Evaluating Safety and Pharmacokinetics of Losatuxizumab Vedotin (ABBV-221), an Anti-EGFR Antibody-drug Conjugate Carrying Monomethyl Auristatin E, in Patients with Solid Tumors likely to Overexpress EGFR," Investigational New Drugs, Oct. 2020, vol. 38 (5), pp. 1483-1494.
Cleek R.L., et al., "Biodegradable Polymeric Carriers for a bFGF Antibody for Cardiovascular Application," Proceedings of the International Symposium on Controlled Release of Bioactive Materials, 1997, vol. 24, pp. 853-854.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Cochran J.R., et al., "Domain-Level Antibody Epitope Mapping through Yeast Surface Display of Epidermal Growth Factor Receptor Fragments," Journal of Immunological Methods, 2004, vol. 287 (1-2), pp. 147-158.
Co-pending U.S. Appl. No. 09/428,082, filed Oct. 22, 1999.
Co-pending U.S. Appl. No. 16/358,963, filed Mar. 20, 2019.
Crooke S.T., "Molecular Mechanisms of Action of Antisense Drugs," Biochimica et Biophysica Acta, 1999, vol. 1489 (1), pp. 31-44.
Damle N.k., et al., "Antibody-targeted Chemotherapy with Immunoconjugates of Calicheamicin," Current Opinion in Pharmacology, 2003, vol. 3 (4), pp. 386-390.
Danial N.N., et al., "Cell Death: Critical Control Points," Cell, 2004, vol. 116 (2), pp. 205-219.
Datta R., et al., "Overexpression of Bcl-XL by Cytotoxic Drug Exposure Confers Resistance to Ionizing Radiation-induced Internucleosomal DNA Fragmentation," Cell Growth & Differentiation, 1995, vol. 6 (4), pp. 363-370.
Dawson M.A., et al., "Inhibition of BET Recruitment to Chromatin as an Effective Treatment for MLL-fusion Leukaemia," Nature, 2011, vol. 478 (7370), pp. 529-533.
De Groot F.M., et al., "Cascade-Release Dendrimers" Liberate All End Groups Upon a Single Triggering Event in the Dendritic Core, Angewandte Chemie (International Ed. In English), 2003, vol. 42 (37), pp. 4490-4494.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169(6), pp. 3076-3084.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Dick L.W., et al., "Determination of the Origin of the N-terminal Pyro-glutamate Variation in Monoclonal Antibodies Using Model Peptides," Biotechnology and Bioengineering, Jun. 2007, vol. 97 (3), pp. 544-553.

(56) References Cited

OTHER PUBLICATIONS

Dick L.W. Jr., et al., "C-Terminal Lysine Variants in Fully Human Monoclonal Antibodies: Investigation of Test Methods and Possible Causes," Biotechnology and Bioengineering, 2008, vol. 100(6), pp. 1132-1143.
Doronina S.O., et al., "Development of Potent Monoclonal Antibody Auristatin Conjugates for Cancer Therapy," Nature Biotechnology, Jul. 2003, vol. 21 (7), pp. 778-784.
Dorr R.T., et al., "Interactions of Mitomycin C with Mammalian DMA Detected by Alkaline Elution," Cancer Research, Aug. 1985, vol. 45, pp. 3510-3516.
Drobyski W.R., et al., "Phase I Study of Safety and Pharmacokinetics of a Human Anticytomegalovirus Monoclonal Antibody in Allogeneic Bone Marrow Transplant Recipients," Transplantation, 1991, vol. 51 (6), pp. 1190-1196.
Dubowchik et al., The Journal of Organic Chemistry, 1998, vol. 67, pp. 1866-1872.
Dubowchik G.M., et al., "Cathepsin B-Sensitive Dipeptide Prodrugs. 1. a Model Study of Structural Requirements for Efficient Release of Doxorubicin," Bioorganic & Medicinal Chemistry Letters, 1998, vol. 8 (23), pp. 3341-3346.
Dubowchik G.M., et al., "Receptor-mediated and Enzyme-dependent Targeting of Cytotoxic Anticancer Drugs," Pharmacology & Therapeutics, Sep. 1999, vol. 83 (2), pp. 67-123.
Ducry L., et al., "Antibody-Drug Conjugates: Linking Cytotoxic Payloads to Monoclonal Antibodies," Bioconjugate Chemistry, 2010, vol. 21 (1), pp. 5-13.
During M. J., et al., "Controlled Release of Dopamine from a Polymeric Brain Implant: In Vivo Characterization," Annals of Neurology, 1989, vol. 25 (4), pp. 351-356.
Durocher Y., et al., "High-Level and High-Throughput Recombinant Protein Production by Transient Transfection of Suspension-Growing Human 293-EBNA1 Cells," Nucleic Acids Research, 2002, vol. 30 (2), pp. 1-9.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Elleman T.C., et al., "Identification of a Determinant of Epidermal Growth Factor Receptor Ligand-Binding Specificity using a Truncated, High-Affinity form of the Ectodomain," Biochemistry, 2001, vol. 40 (30), pp. 8930-8939.
Estrach S., et al., "CD98hc (SLC3a2) Loss Protects Against Ras-driven Tumorigenesis by Modulating Integrin-mediated Mechanotransduction," Cancer Research, Dec. 2014, vol. 74 (23), pp. 6878-6889.
Feldhaus M.J., et al., "Flow-Cytometric Isolation of Human Antibodies from a Nonimmune *Saccharomyces cerevisiae* Surface Display Library," Nature Biotechnology, 2003, vol. 21 (2), pp. 163-170.
Fernandes H., et al., "Glycosylation-Induced Conformational Modification Positively Regulates Receptor-Receptor Association: A Study with an Aberrant Epidermal Growth Factor Receptor (EGFRvIII/DeltaEGFR) Expressed in Cancer Cells," Journal of Biological Chemistry, 2001, vol. 276 (7), pp. 5375-5383.
Fire A., et al., "Potent and Specific Genetic Interference by Double-Stranded RNA in Caenorhabditis Elegans," Nature, 1998, vol. 391 (6669), pp. 806-811.
Fisher., Laboratory Techniques in Biochemistry and Molecular Biology, Elsevier, 1980.
Flanagan., et al., Monoclonal Antibodies: Methods and Protocols, in: Methods in Molecular Biology, vol. 378.
Francisco J.A., et al., "cAC10-vcMMAE, an Anti-CD30-Monomethyl Auristatin E Conjugate with Potent and Selective Antitumor Activity," Blood, 2003, vol. 102 (4), pp. 1458-1465.
Friedman H.S., et al., "Temozolomide and Treatment of Malignant Glioma," Clinical Cancer Research, 2000, vol. 6 (7), pp. 2585-2597.
Gan H.K., et al., "Targeting of a Conformationally Exposed, Tumor-Specific Epitope of EGFR as a Strategy for Cancer Therapy," Cancer Research, 2012, vol. 72 (12), pp. 1-7.

Garcia De Palazzo IE., et al., "Expression of Mutated Epidermal Growth Factor Receptor by Non-Small Cell Lung Carcinomas," Cancer Research, Jul. 1993, vol. 53 (14), pp. 3217-3220.
Garrett T.P., et al., "Antibodies Specifically Targeting a Locally Misfolded Region of Tumor Associated EGFR," Proceedings of the National Academy of Sciences, 2009, vol. 106 (13), pp. 5082-5087.
Ge H., et al., "Evidence of High Incidence of Egfrviii Expression and Coexpression with Egfr in Human Invasive Breast Cancer by Laser Capture Microdissection and Immunohistochemical Analysis," International Journal of Cancer, Mar. 2002, vol. 98 (3), pp. 357-361.
Gelboin H.V., et al., "Polyinosinic-polycytidylic Acid Inhibits Chemically Induced Tumorigenesis in Mouse Skin.," Science, Jan. 1970, vol. 167 (3915), pp. 205-207.
George J., et al., "Differential Effects of Anti-Beta2-Glycoprotein I Antibodies on Endothelial Cells and on the Manifestations of Experimental Antiphospholipid Syndrome," Circulation, 1998, vol. 97, pp. 900-906.
Gerber H. P., et al., "Antibody Drug-conjugates Targeting the Tumor Vasculature: Current and Future Developments," Mabs, May-Jun. 2009, vol. 1(3), pp. 247-253.
Gerstenberger B.S., et al., "Tert-buyldiphenylsilylethyl ("TBDPSA"): A Practical Protecting Group for Phenols," The Journal of Organic Chemistry, 2005, vol. 70 (4), pp. 1467-1470.
Gill G.N., et al., "Relationship Between Production of Epidermal Growth Factor Receptors, Gene Amplification, and Chromosome 7 Translocation in Variant A431 Cells," Somatic Cell and Molecular Genetics, 1985, vol. 11 (4), pp. 309-318.
Gillies S.D., et al., "High-Level Expression of Chimeric Antibodies Using Adapted cDNA Variable Region Cassettes," Journal of Immunological Methods, Dec. 1989, vol. 125(1-2), pp. 191-202.
Giusti A.M., et al., "Somatic Diversification of S107 from an Antiphosphocholine to an Anti-DNA Autoantibody is due to a Single Base Change in its Heavy Chain Variable Region," Proceedings of the National Academy of Sciences, 1987, vol. 84 (9), pp. 2926-2930.
Goeddel D.V., "Systems for Heterologous Gene Expression," Methods in Enzymology, 1990, vol. 185, pp. 3-7.
Goldberg D. M. (ed.), Cancer Therapy with Radiolabeled Antibodies, CRC Press, 1995, 6 pages.
Goldspiel B.R., et al., "Human Gene Therapy," Clinical Pharmacy, 1993, vol. 12 (7), pp. 488-505.
Goldstein J.C., et al., "Cytochrome C is Released in a Single Step During Apoptosis," Cell Death and Differentiation, 2005, vol. 12 (5), pp. 453-462.
Goodson J.M., "Dental Applications," Medical Applications of Controlled Release, 1984, vol. 2 (Chapter 6), pp. 115-138.
Greene T.W., et al., "Protection for the Amino group," Protective Groups in Organic Synthesis, 1999, Third Edition, pp. 494-653.
Greene T.W., et al., Protective Groups in Organic Synthesis, 3rd Edition, John Wiley and Sons, Inc., 1999, Preface, Table of Contents, Abbreviations.
Greenspan N.S., et al., "Defining Epitopes: It's not as Easy as it seems," Nature Biotechnology, 1999, vol. 17 (10), pp. 936-937.
Hamblett K.J., et al., "Effects of Drug Loading on the Antitumor Activity of a Monoclonal Antibody Drug Conjugate," Clinical Cancer Research, 2004, vol. 10 (20), pp. 7063-7070.
Harlow E., et al., "Antibody: A Laboratory Manual," Cold Spring Harbor Laboratory Press, Cold Spring Harbor, NY, 1998.
Hashiguchi M., et al., "Triggering Receptor Expressed on Myeloid Cell-like Transcript 2 (TLT-2) is a Counter-receptor for B7-H3 and Enhances T Cell Responses," Proceedings of the National Academy of Sciences of the United States of America, Jul. 2008, vol. 105 (30), pp. 10495-10500.
Haura E.B., et al., "Antiapoptotic Signaling Pathways in Non-small-cell Lung Cancer: Biology and Therapeutic Strategies," Clinical Lung Cancer, 2004, vol. 6 (2), pp. 113-122.
Hay M.P., et al., "A 2-nitroimidazole Carbamate Prodrug of 5-amimo-1-(Chloromethyl)-3-[(5,6,7-trimethoxyindol-2-yl)carbony L]-1,2-dihydro-3h--benz[E]indole (Amino-seco-CBI-TMI) for use with ADEPT and GDEPT," Bioorganic & Medicinal Chemistry Letters, Aug. 1999, vol. 9 (15), pp. 2237-2242.

(56) References Cited

OTHER PUBLICATIONS

Hayes G.M., et al., "Antitumor Activity of an Anti-CD98 Antibody," International Journal of Cancer, Aug. 1, 2015, vol. 137 (3), pp. 710-720.

Haynes B. F. et al., "Characterization of a Monoclonal Antibody (4F2) that Binds to Human Monocytes and to a Subset of Activated Lymphocytes," Journal of Immunology, 1981, vol. 126 (4), pp. 1409-1414.

Hellstrom et al., "Antibodies for Drug Delivery," in: Controlled Drug Delivery, 2nd Edition, 1987, Marcel Dekker, Inc.

Herbst R.S., et al., "Monoclonal Antibodies to Target Epidermal Growth Factor Receptor-Positive Tumors: A New Paradigm for Cancer Therapy.," Cancer, 2002, vol. 9 4 (5), pp. 1593-1611.

Hermanson, Bioconjugate Techniques, Academic Press 1996, Table of Contents.

Hermanson G.T., "Antibody Modification and Conjugation," in: Bioconjugate Techniques, 1996, Chapter 10, Academic Press, pp. 456-493.

Hills D., et al., "Specific Targeting of a Mutant, Activated FGF Receptor Found in Glioblastoma Using a Monoclonal Antibody," International Journal of Cancer, 1995, vol. 63 (4), pp. 537-543.

Hinman L.M., et al., "Preparation and Characterization of Monoclonal Antibody Conjugates of the Calicheamicins: a Novel and Potent Family of Antitumor Antibiotics," Cancer Research, 1993, vol. 53 (14), pp. 3336-3342.

Hoang T., et al., "PD-144 Tumor Response Augmentation with Combination Cetuximab (Erbitux(R)) and Bevacizumab (Avastin(R))," Lung Cancer, 2005, vol. 49, pp. S108-S109.

Hollander I., et al., "Selection of Reaction Additives Used in the Preparation of Monomeric Antibody-Calicheamicin Conjugates," Bioconjugate Chemistry, 2008, vol. 19 (1), pp. 358-361.

Holliger P., et al., ""Diabodies": Small Bivalent and Bispecific Antibody Fragments," Proceedings of the National Academy of Sciences, 1993, vol. 90 (14), pp. 6444-6448.

Holm P., et al., "Functional Mapping and Single Chain Construction of the Anti-Cytokeratin 8 Monoclonal Antibody TS1," Molecular Immunology, 2007, vol. 44(6), pp. 1075-1084.

Howard 3rd1 M.A., et al., "Intracerebral Drug Delivery in Rats with Lesion-Induced Memory Deficits," Journal of Neurosurgery, 1989, vol. 71 (1), pp. 105-112.

Huang B., et al., "Brd4 Coactivates Transcriptional Activation of NF-kappaB via Specific Binding to Acetylated RelA," Molecular and Cellular Biology, 2009, vol. 29 (5), pp. 1375-1387.

Hubbell H.R., et al., "Cyclic AMP Mediates the Direct Antiproliferative Action of Mismatched Double-stranded RNA," Proceedings of the National Academy of Sciences of the United States of America, Feb. 1991, vol. 88 (3), pp. 906-910.

Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.

International Search Report and Written Opinion for Application No. PCT/CN2014/000258, dated May 28, 2014, 17 pages.

International Search Report and Written Opinion for Application No. PCT/US2015/064686, dated Apr. 4, 2016, 9 pages.

International Search Report and Written Opinion for Application No. PCT/US2015/064693, dated May 10, 2016, 22 pages.

International Search Report and Written Opinion for Application No. PCT/US2015/064706, dated May 27, 2016, 19 pages.

International Search Report and Written Opinion for Application No. PCT/US2017/036288, dated Sep. 7, 2017, 12 pages.

International Search Report and Written Opinion for Application No. PCT/US2017/036368, dated Aug. 22, 2017, 14 pages.

International Search Report and Written Opinion for Application No. PCT/US2017/036399, dated Sep. 7, 2017, 12 pages.

International Search Report and Written Opinion for Application No. PCT/US2017/036428, dated Oct. 4, 2017, 23 pages.

International Search Report and Written Opinion for Application No. PCT/US2017/036445, dated Nov. 21, 2017, 33 pages.

International Search Report and Written Opinion for Application No. PCT/US2017/036449, dated Oct. 2, 2017, 24 pages.

International Search Report and Written Opinion for Application No. PCT/US2017/036639, dated Nov. 15, 2017, 22 pages.

International Search Report and Written Opinion for Application No. PCT/US2017/036645, dated Dec. 21, 2017, 22 pages.

International Search Report and Written Opinion for Application No. PCT/US2017/036650, dated Dec. 11, 2017, 23 pages.

International Search Report and Written Opinion for International Application No. PCT/US2015/021849, dated Jul. 13, 2015.

Itoh K., et al., "Phage Display Cloning and Characterization of Monoclonal Antibody Genes and Recombinant Fab Fragment Against the Cd98 Oncoprotein," Japanese Journal of Cancer Research, Dec. 2001, vol. 92 (12), pp. 1313-1321.

Janeway C.A., et al., "The Immune System in Health and Disease" in: Immunobiology, 5th Edition., Garland Science, 2001, pp. 94-105.

Jang M.K., et al., "The Bromodomain Protein Brd4 is a Positive Regulatory Component of P-TEFb and Stimulates RNA Polymerase II-dependent Transcription," Molecular Cell, 2005, vol. 19(4), pp. 523-534.

Jefferis R., "Glycosylation of Recombinant Antibody Therapeutics," Biotechnology Program, 2005, vol. 21 (1), pp. 11-16.

Jeffrey S.C., et al., "Development and Properties of Beta-Glucuronide Linkers for Monoclonal Antibody-Drug Conjugates," Bioconjugate Chemistry, 2006, vol. 17 (3), pp. 831-840.

Jeffrey S.C et al., "Expanded Utility of the β-Glucuronide Linker: ADCs That Deliver Phenolic Cytotoxic Agents." ACS Medical Chemistry Letters, 2010, vol. 1(6), pp. 277-280.

Jeffrey S.C., et al., "Minor Groove Binder Antibody Conjugates Employing a Water Soluble Beta-Glucuronide Linker," Bioorganic & Medicinal Chemistry Letters, 2007, vol. 17 (8), pp. 2278-2280.

Jespers L.S., et al., "Guiding the Selection of Human Antibodies from Phage Display Repertoires to a Single Epitope of an Antigen," Bio/Technology, 1994, vol. 12 (9), pp. 899-903.

Jiang B., et al., "A Novel Peptide Isolated from a Phage Display Peptide Library with TrastuzumAb can Mimic Antigen Epitope of HER-2," The Journal of Biological Chemistry, 2005, vol. 280 (6), pp. 4656-4662.

Jiang X., et al., "Synthesis and Complete Stereochemical Assignment of Psymberin/Irciniastatin A," Journal of the American Chemical Society, 2005, vol. 127 (32), pp. 11254-11255.

Johns et al., "Annual Branch Report 1998 (Pre-clinical Evaluation of Antibodies Directed to the De2-7 Epidermal Growth Factor Receptors)," Ludwig Institute for Cancer Research, 2000, pp. 118-119.

Johns T.G., et al., "Identification of the Epitope for the Epidermal Growth Factor Receptor-Specific Monoclonal Antibody 806 Reveals That it Preferentially Recognizes an Untethered Form of the Receptor," Journal of Biological Chemistry, 2004, vol. 279 (29), pp. 30375-30384.

Johns T.G., et al., "Novel Monoclonal Antibody Specific for the de2-7 Epidermal Growth Factor Receptor (EGFR) that also Recognizes the EGFR Expressed in Cells Containing Amplification of the EGFR Gene," International Journal of Cancer, 2002, vol. 98 (3), pp. 398-408.

Johns T.G., et al., "The Antitumor Monoclonal Antibody 806 Recognizes a High-Mannose form of the EGF Receptor that Reaches the Cell Surface when Cells Over-Express the Receptor," FASEB Journal, 2005, vol. 19 (7), pp. 780-782.

Johnson D.A., et al., "Anti-tumor Activity of CC49-doxorubicin Immunoconjugates," Anticancer Research Jul. 1995, vol. 15 (4), pp. 1387-1393.

Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8, Issue (1-2), pp. 125-131.

Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.

Joliot A., et al., "Antennapedia Homeobox Peptide Regulates Neural Morphogenesis," Proceedings of the National Academy of Sciences, 1991, vol. 88 (5), pp. 1864-1868.

(56) References Cited

OTHER PUBLICATIONS

Jones P.T., et al., "Replacing the Complementarity-Determining Regions in a Human Antibody with those from a Mouse," Nature, 1986, vol. 321 (6069), pp. 522-525.
Jonsson U., et al., "Introducing a Biosensor Based Technology for Real-Time Biospecific Interaction Analysis," Annals of Clinical Biology, 1993, vol. 51 (1), pp. 19-26.
Jonsson U., et al., "Real-Time Biospecific Interaction Analysis Using Surface Plasmon Resonance and a Sensor Chip Technology," Biotechniques, 1991, vol. 11 (5), pp. 620-627.
Jordan V. C., "Tamoxifen: a Most Unlikely Pioneering Medicine," Nature Reviews Drug Discovery, 2003, vol. 2 (3), pp. 205-213.
Jung Y.D., et al., "Effects of Combination Anti-Vascular Endothelial Growth Factor Receptor and Anti-Epidermal Growth Factor Receptor Therapies on the Growth of Gastric Cancer in a Nude Mouse Model," European Journal of Cancer, 2002, vol. 38 (8), pp. 1133-1140.
Jungbluth A.A., et al., "A Monoclonal Antibody Recognizing Human Cancers with Amplification/Overexpression of the Human Epidermal Growth Factor Receptor," Proceedings of the National Academy of Sciences, 2003, vol. 100 (2), pp. 639-644.
Junutula J.R., et al., "Site-specific Conjugation of a Cytotoxic Drug to an Antibody Improves the Therapeutic Index," Nature Biotechnology, 2008, vol. 26 (8), pp. 925-932.
Kabat E.A., et al., "Accession No. PS91-192898, Sequences of Proteins of Immunological Interest," National Institutes of Health Publication No. 91-3242, 5th Edition, 1991, pp. 647-669.
Kabat E.A., et al., "Attempts to Locate Complementarity-Determining Residues in the variable Positions of Light and Heavy Chains," Annals New York Academy of Sciences, 1971, vol. 190, pp. 382-391.
Kabat E.A., et al., in: Sequence of Proteins of Immunological Interest, 4th Edition, 1987, Table of Contents.
Kabat., "Sequences of Proteins of Immunological Interest," 1983, Table of Contents.
Kabat., et al., "Sequences of Proteins of Immunological Interest," National Institutes of Health, Bethesda, Md. 1987.
Kaira K., et al., "CD98 Expression is Associated with Poor Prognosis in Resected Non-small-cell Lung Cancer with Lymph Node Metastases," Annals of Surgical Oncology, Dec. 2009, vol. 16(12), pp. 3473-3481.
Kaira K., et al., "I-type Amino Acid Transporter 1 and CD98 Expression in Primary and Metastatic Sites of Human Neoplasms," Cancer Science, Dec. 2008, vol. 99 (12), pp. 2380-2386.
Kaira K., et al., "Prognostic Significance of L-type Amino Acid Transporter 1 (Lat1) and 4F2 Heavy Chain (CD98) Expression in Stage I Pulmonary Adenocarcinoma," Lung Cancer, Oct. 2009, vol. 66 (1), pp. 120-126.
Kalia J., et al., "Catalysis of Imido Group Hydrolysis in a Maleimide Conjugate," Bioorganic & Medicinal Chemistry Letters, Nov. 2007, vol. 17 (22), pp. 6286-6289.
Kamala T., "Hock Immunization: A Humane Alternative to Mouse Footpad Injections," Journal of Immunological Methods, Dec. 2007, vol. 328 (1-2), pp. 204-214.
Kamijo S., et al., "Photochemically Induced Radical Transformation of C(Sp3)-h Bonds to C(Sp3)-cn Bonds," Organic Letters, 2011, vol. 13 (21), pp. 5928-5931.
Kaneko T., et al., "New Hydrazone Derivatives of Adriamycin and their Immunoconjugates—a Correlation Between Acid Stability and Cytotoxicity," Bioconjugate Chemistry, May-Jun. 1991, vol. 2(3), pp. 133-141.
Kaufman R.J., et al., "Amplification and Expression of Sequences Cotransfected with a Modular Dihydrofolate Reductase Complementary DNA Gene," Journal of Molecular Biology, 1982, vol. 159(4), pp. 601-621.
Kennedy K.A., et al., "pH Dependence of Mitomycin C-induced Cross-linking Activity in EMT6 Tumor Cells," Cancer Research, Aug. 1985, vol. 45 (8), pp. 3541-3547.
Khalil M. et al., "Molecular SPECT Imaging: An Overview," International Journal of Molecular Imaging, vol. 2011, Article ID 796025, pp. 1-15.
King H.D., et al., "Facile Synthesis of Maleimide Bifunctional Linkers," Tetrahedron Letters, Mar. 2002, vol. 43 (11), pp. 1987-1990.
King H.D., et al., "Monoclonal Antibody Conjugates of Doxorubicin Prepared with Branched Peptide Linkers: Inhibition of Aggregation by Methoxytriethyleneglycol Chains," Journal of Medicinal Chemistry, 2002, vol. 45 (19), pp. 4336-4343.
Kingsbury W.D., et al., "A Novel Peptide Delivery System Involving Peptidase Activated Prodrugs as Antimicrobial Agents. Synthesis and Biological Activity of Peptidyl Derivatives of 5-fluorouracil," Journal of Medicinal Chemistry, Nov. 1984, vol. 27 (11), pp. 1447-1451.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kipriyanov S.M., et al., "Recombinant Single-Chain Fv Fragments Carrying C-Terminal Cysteine Residues: Production of Bivalent and Biotinylated Miniantibodies," Molecular Immunology, 1994, vol. 31 (14), pp. 1047-1058.
Kirkin V., et al., "The Role of Bcl-2 Family Members in Tumorigenesis," Biochimica et Biophysica Acta, 2004, vol. 1644 (2-3), pp. 229-249.
Kitson S.L., et al., "Antibody-Drug Conjugates (ADCs)-Biotherapeutic Bullets," Chemistry Today, 2013, vol. 31 (4), pp. 30-36.
Klussman K. et al., "Secondary mAb--vcMMAE conjugates are highly sensitive reporters of antibody internalization via the lysosome pathway," Bioconjugate Chemistry, 2004, vol. 15 (4), pp. 765-773.
Koenig S., et al., "Targeting B7-H3 in Cancer," Medicographia, 2014, vol. 36 (3), pp. 285-292.
Kohler G., et al., "Continuous Cultures of Fused Cells Secreting Antibody of Predefined Specificity," Nature, Aug. 1975, vol. 256 (5517), pp. 495-497.
Kontermann R., et al., eds., Antibody Engineering, Springer-Verlag Berlin Heidelberg, New York, 2001, (ISBN 3-540-41354-5),Table of Contents.
Kriegler M., Gene Transfer and Expression: A Laboratory Manual, Stockton Press, 1990, Table of Contents.
Kuan C.T., et al., "125I-Labeled Anti-Epidermal Growth Factor Receptor-Yin Single-Chain Fv Exhibits Specific And High-Level Targeting of Glioma Xenografts," Clinical Cancer Research, 1999, vol. 5(6), pp. 1539-1549.
Kuan C.T., et al., "EGF Mutant Receptor vIII as a Molecular Target in Cancer Therapy," Endocrine-Related Cancer, 2001, vol. 8 (2), pp. 83-96.
Kuan C.T., et al., "Increased Binding Affinity Enhances Targeting of Glioma Xenografts by EGFRvIII-Specific scFv," International Journal of Cancer, 2000, vol. 88 (6), pp. 962-969.
Kung Sutherland M.S., et al., "SGN-CD33A: A Novel CD33-Targeting Antibody-Drug Conjugate Using a Pyrrolobenzodiazepine Dimer is Active in Models of Drug-Resistant Aml," Blood, 2013, vol. 122 (8), pp. 1455-1463.
Kupchan S.M., et al., "Maytansine, a Novel Antileukemic Ansa Macrolide From Maytenus Ovatus," Journal of the American Chemical Society, Feb. 1972, vol. 94 (4), pp. 1354-1356.
Kupchan S.M., et al., "Structural Requirements for Antileukemic Activity among the Naturally Occurring and Semisynthetic Maytansinoids," Journal of Medicinal Chemistry, Jan. 1978, vol. 21 (1), pp. 31-37.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Langer, et al., eds., International Journal of Biological Macromolecules, 1983, vol. 23, pp. 61-127.
Langer R., et al., "Chemical and Physical Structure of Polymers as Carriers for Controlled Release of Bioactive Agents: A Review," Journal of Macromolecular Science—Reviews in Macromolecular Chemistry & Physics, 1983, vol. C23 (1), pp. 61-126.

(56) References Cited

OTHER PUBLICATIONS

Langer R., "New Methods of Drug Delivery," Science, 1990, vol. 249 (4976), pp. 1527-1533.
Larrick J.W., et al., "Therapeutic Human Antibodies Derived from PCR Amplification of B-Cell Variable Regions," Immunological Reviews, 1992, vol. 130, pp. 69-85.
Lau A., et al., "Conjugation of Doxorubicin to Monoclonal Anticarcinoembryonic Antigen Antibody via Novel Thiol-directed Cross-linking Reagents," Bioorganic & Medicinal Chemistry, Oct. 1995, vol. 3 (10), pp. 1299-1304.
Lau A., et al., "Novel Doxorubicin-monoclonal Anticarcinoembryonic Antigen Antibody Immunoconjugate Activity in Vitro," Bioorganic & Medicinal Chemistry, Oct. 1995, vol. 3 (10), pp. 1305-1312.
Laurent Ducry., "Antibody-Drug Conjugates," Springer Science & Business Media, LLC, 2013.
Lax L., et al., "Noncontiguous Regions in the Extracellular Domain of EGF Receptor Define Ligand-Binding Specificity," Cell Regulation, 1991, vol. 2 (5), pp. 337-345.
Lebel H., et al., "Boc-protected Amines via a Mild and Efficient One-pot Curtius Rearrangement," Organic Letters, 2005, vol. 7 (19), pp. 4107-4110.
Lee S., et al., "Cytokines in Cancer Immunotherapy," Cancers, Oct. 2011, vol. 3 (4), pp. 3856-3893.
Leroy G., et al., "The Double Bromodomain Proteins Brd2 and Brd3 Couple Histone Acetylation to Transcription," Molecular Cell, 2008, vol. 30 (1), pp. 51-60.
Lessene G., et al., "Structure-guided Design of a Selective Bcl-x(L) Inhibitor," Nature Chemical Biology, 2013, vol. 9 (6), pp. 390-397.
Leverson J.D., et al., "Exploiting Selective BCL-2 Family Inhibitors to Dissect Cell Survival Dependencies and Define Improved Strategies for Cancer Therapy," Science Translational Medicine, 2015, vol. 7 (279), 279ra40, pp. 1-12.
Levy H.B., et al., "Inhibition of Tumor Growth by Polyinosinic-polycytidylic Acid," Proceedings of the National Academy of Sciences of the United States of America, Feb. 1969, vol. 62 (2), pp. 357-361.
Levy R.D., et al., "Inhibition of Calcification of Bioprosthetic Heart Valves by Local Controlled-Release Diphosphonate," Science, 1985, vol. 228 (4696), pp. 190-192.
Li S., et al., "Structural Basis for Inhibition of the Epidermal Growth Factor Receptor by CetuximAb," Cancer Cell, 2005, vol. 7 (4), pp. 301-311.
Lindsten T., et al., "Regulation of 4F2 Heavy-chain Gene Expression During Normal Human T-cell Activation can be Mediated by Multiple Distinct Molecular Mechanisms," Molecular and Cellular Biology, Sep. 1988, vol. 8 (9), pp. 3820-3826.
Liu X.Y., et al., "Engineering Therapeutic Monoclonal Antibodies," Immunological Reviews, 2008, vol. 222, pp. 9-27.
Liu Y.D., et al., "N-terminal Glutamate to Pyroglutamate Conversion in Vivo for Human IgG2 Antibodies," The Journal of Biological Chemistry, Apr. 2011, vol. 286 (13), pp. 11211-11217.
Lode H.N., et al., "Targeted Therapy with a Novel Enediyene Antibiotic Calicheamicin Theta(I)1 Effectively Suppresses Growth and Dissemination of Liver Metastases in a Syngeneic Model of Murine Neuroblastoma," Cancer Research, 1998, vol. 58 (14), pp. 2925-2928.
Loo D., et al., "Abstract 1201: Anti-B7-H3 Antibody-Drug Conjugates as Potential Therapeutics for Solid Cancer," Cancer Research, Apr. 20, 2016, 4 pages.
Loo D., et al., "Development of an Fc-enhanced Anti-B7-H3 Monoclonal Antibody with Potent Antitumor Activity," Clinical Cancer Research, Jul. 15, 2012, vol. 18 (14), pp. 3834-3845.
Loos M., et al., "Expression of the Costimulatory Molecule B7-H3 is Associated with Prolonged Survival in Human Pancreatic Cancer," BMC Cancer, Dec. 2009, vol. 9, p. 463.
Lund J., et al., "Human Fc Gamma RI and Fc Gamma RII Interact with Distinct but Overlapping Sites on Human IgG," Journal of Immunology, 1991, vol. 147 (8), pp. 2657-2662.
Luwor R.B., et al., "Monoclonal Antibody 806 Inhibits the Growth of Tumor Xenografts Expressing Either the de2-7 or Amplified Epidermal Growth Factor Receptor (EGFR) but not Wild-Type EGFR," Cancer Research, 2001, vol. 61 (14), pp. 5355-5361.
Lyon R.P., et al., "Self-Hydrolyzing Maleimides Improve the Stability and Pharmacological Properties of Antibody-Drug Conjugates," Nature Biotechnology, 2014, vol. 32 (10), pp. 1059-1062.
MacCallum R.M., et al., "Antibody-antigen Interactions: Contact Analysis and Binding Site Topography," Journal of Molecular Biology, 1996, vol. 262 (5), pp. 732-745.
Macrogenics, Corporate Fact Sheet, Jan. 30, 2018, 2 pages.
MacroGenics., "MacroGenics Presents Data from Five Preclinical Programs at AACR Annual Meeting 2016," Rockville Maryland, Apr. 19, 2016, pp. 1-3. Available at https://www.globenewswire.com/news-release/2016/04/19/830245/0/en/MacroGenics-Presents-Data-from-Five-Preclinical-Programs-at-AACR-Annual-Meeting-2016.html.
Mariuzza R.A., et al., "The Structural Basis of Antigen-Antibody Recognition," Annual Review of Biophysics and Biophysical Chemistry, 1987, vol. 16, pp. 139-159.
Marks J.D., et al., "By-Passing Immunization: Building High Affinity Human Antibodies by Chain Shuffling," Biotechnology, 1992, vol. 10 (7), pp. 779-783.
Mason K.D., et al., "Programmed Anuclear Cell Death Delimits Platelet Life Span," Cell, 2007, vol. 128(6), pp. 1173-1186.
Matzuk M.M., et al., "Small-molecule Inhibition of BRDT for Male Contraception," Cell, 2012, vol. 150(4), pp. 673-684.
Medical Applications of Controlled Release, Langer and Wise (eds.), CRC Pres., Boca Raton, Fla. (1974).
Mertz J.A., et al., "Targeting MYC Dependence in Cancer by Inhibiting BET Bromodomains," Proceedings of the National Academy of Sciences, 2011, vol. 108 (40), pp. 16669-16674.
Mishima K., et al., "Growth Suppression of Intracranial Xenografted Glioblastomas Overexpressing Mutant Epidermal Growth Factor Receptors by Systemic Administration of Monoclonal Antibody (mAb) 806, A Novel Monoclonal Antibody Directed to the Receptor," Cancer Research, 2001, vol. 61 (14), pp. 5349-5354.
Miyaura N., et al., "Palladium-Catalyzed Cross-Coupling Reactions of Organoboron Compounds," Chemical Reviews, 1995, vol. 95 (7), pp. 2457-2483.
Modjtahedi H., et al., "Antitumor Activity of Combinations of Antibodies Directed Against Different Epitopes on the Extracellular Domain of the Human EGF Receptor," Cell Biophysics, 1993, vol. 22 (1-3), pp. 129-146.
Modjtahedi H., et al., "Phase I Trial and Tumour Localisation of the Anti-EGFR Monoclonal Antibody ICR62 in Head and Neck or Lung Cancer," British Journal of Cancer, 1996, vol. 73 (2), pp. 228-235.
Morgan R.A., et al., "Human Gene Therapy," Annual Review of Biochemistry, 1993, vol. 62, 191-217.
Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.
Morrison S.L., "Transfectomas Provide Novel Chimeric Antibodies," Science, 1985, vol. 229 (4719), pp. 1202-1207.
Moscatello D.K., et al., "Frequent Expression of a Mutant Epidermal Growth Factor Receptor in Multiple Human Tumors," Cancer Research, Dec. 1995, vol. 55 (23), pp. 5536-5539.
Mullard A., "Pioneering Apoptosis-targeted Cancer Drug Poised for FDA Approval," Nature Reviews Drug Discovery, Mar. 2016, vol. 15 (3), pp. 147-149.
Mulligan R.C., "The Basic Science of Gene Therapy," Science, May 1993, vol. 260 (5110), pp. 926-932.
Nagamura S., et al., "Antitumor Antibiotics: Duocarmycins,"Chemistry of Heterocyclic Compounds, Dec. 1998, vol. 34 (12), pp. 1386-1405.
Nagane M., et al., "A Common Mutant Epidermal Growth Factor Receptor Confers Enhanced Tumorigenicity on Human Glioblastoma Cells by Increasing Proliferation and Reducing Apoptosis," Cancer Research, 1996, vol. 56 (21), pp. 5079-5086.

(56) References Cited

OTHER PUBLICATIONS

Nagase-Zembutsu A., et al., "Development of DS-5573a: A Novel Afucosylated mAb Directed at B7-H3 With Potent Antitumor Activity," Cancer Science, May 2016, vol. 107 (5), pp. 674-681.
Naumov G.N., et al., "Combined Vascular Endothelial Growth Factor Receptor and Epidermal Growth Factor Receptor (EGFR) Blockade Inhibits Tumor Growth in Xenograft Models of EGFR Inhibitor Resistance," Clinical Cancer Research, 2009, vol. 15 (10), pp. 3484-3494.
Neuberger M.S., et al., "Recombinant Antibodies Possessing Novel Effector Functions," Nature, 1984, vol. 312 (5995), pp. 604-608.
Neville D.M., et al., "Enhancement of Immunotoxin Efficacy by Acid-cleavable Cross-linking Agents Utilizing Diphtheria Toxin and Toxin Mutants," Journal of Biological Chemistry, Sep. 1989, vol. 264 (25), pp. 14653-14661.
Nicodeme E., et al., "Suppression of Inflammation by a Synthetic Histone Mimic," Nature, 2010, vol. 468 (7327), pp. 1119-1123.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Nishikawa R., et al., "A Mutant Epidermal Growth Factor Receptor Common in Human Glioma Confers Enhanced Tumorigenicity," Proceedings of the National Academy of Sciences, 1994, vol. 91 (16), pp. 7727-7731.
Nolting B., et al., "Linker Technologies for Antibody-Drug Conjugates," Methods in Molecular Biology (Clifton, N.J.), 2013, vol. 1045, pp. 71-100.
Nygren M.K., et al., "B7-H3 and its Relevance in Cancer; Immunological and Non-immunological Perspectives," Frontiers in Bioscience, Jun. 2011, vol. 3, pp. 989-993.
Ogitani Y. et al., "Wide application of a novel topoisomerase I inhibitor-based drug conjugation technology." Bioorganic & Medicinal Chemistry Letters, 2016, vol. 26, pp. 5069-5072.
Oi V.T., et al., "Chimeric Antibodies," BioTechniques, 1986, vol. 4 (3), pp. 214-221.
Olapade-Olaopa E.O., et al., "Evidence for the Differential Expression of a Variant EGF Receptor Protein in Human Prostate Cancer," British Journal of Cancer, 2000, vol. 82 (1), pp. 186-194.
Olson J., et al., "Customization of a Commercially Available Prep Scale SFC System to Provide Enhanced Capabilities," Jala, 2002, vol. 7 (4), pp. 69-74.
Order S.E., "Analysis, Results, and Future Prospective of the Therapeutic Use of Radiolabeled Antibody in Cancer Therapy," in: Monoclonal Antibodies for Cancer Detection and Therapy, Baldwin., et al., Eds., Academic Press, 1985.
Padlan E.A., "A Possible Procedure for Reducing the Immunogenicity of Antibody Variable Domains While Preserving Their Ligand-Binding Properties," Molecular Immunology, 1991, vol. 28 (4-5), pp. 489-498.
Padlan E.A., et al., "Identification of Specificity-determining Residues in Antibodies," FASEB Journal, 1995, vol. 9 (1), pp. 133-139.
Panousis C., et al., "Engineering and Characterisation of Chimeric Monoclonal Antibody 806 (ch806) for Targeted Immunotherapy of Tumours Expressing de2-7 EGFR or Amplified EGFR," British Journal of Cancer, 2005, vol. 92 (6), pp. 1069-1077.
Park D., et al., "Novel Small-molecule Inhibitors of BCL-XL to Treat Lung Cancer," Cancer Research, 2013, vol. 73 (17), pp. 5485-5496.
Parmacek M.S., et al., "Structure, Expression and Regulation of the Murine 4F2 Heavy Chain," Nucleic acids research, Mar. 1989, vol. 17 (5), pp. 1915-1931.
Pauff S.M., et al., "A Trifluoroacetic Acid-labile Sulfonate Protecting Group and its use in the Synthesis of a Near-IR Fluorophore," The Journal of Organic Chemistry, Jan. 2013, vol. 78 (2), pp. 711-716.
Perera R.M., et al., "Internalization, Intracellular Trafficking, and Biodistribution of Monoclonal Antibody 806: A Novel Anti-Epidermal Growth Factor Receptor Antibody," Neoplasia, 2007, vol. 9(12), pp. 1099-1110.
Perez.H.L et al., "Antibody-Drug Conjugates: Current Status and Future Directions," Journal of Drug Discovery Today, Jul. 2014, vol. 19 (7), pp. 869-881.
Peters C., et al., "Antibody-drug Conjugates as Novel Anti-cancer Chemotherapeutics," Bioscience Reports, 2015, vol. 35(4), e00225.
Pettit G.R., et al., "Structure of an Antineoplastic Agent from *Streptomyces griseoluteus*," Journal of the American Chemical Society, Oct. 1976, vol. 98 (21), pp. 6742-6743.
Pettit G.R., "The Dolastatins," Progress in the Chemistry of Organic Natural Products, 1997, vol. 70, pp. 1-79.
Picarda E., et al., "Molecular Pathways: Targeting B7-H3 (CD276) for Human Cancer Immunotherapy," Clinical Cancer Research, Jul. 15, 2016, vol. 22 (14), pp. 3425-3431.
Poljak R.J., "Production and Structure of Diabodies," Structure, 1994, vol. 2 (12), pp. 1121-1123.
Powell., et al., "Additional New Maytansinoids from Trewia nudiflora: 10-Epitrewiasine and Nortrewiasine," Journal of Natural Products, 1983, vol. 46 (5), pp. 660-666.
Prasad D.V., et al., "Murine B7-H3 is a Negative Regulator of T Cells," Journal of Immunology, Aug. 2004, vol. 173 (4), pp. 2500-2506.
Prescott D. M., "Methods in Cell Biology", vol. XIV, Academic Press, New York, N.Y. (1976), p. 33-68.
Press O.W., et al., "Ricin A-Chain Containing Immunotoxins Directed Against Different Epitopes on the CD2 Molecule Differ in Their Ability to Kill Normal and Malignant T Cells," The Journal of Immunology, 1988, vol. 141, pp. 4410-4417.
Presta L.G., "Engineering of Therapeutic Antibodies to Minimize Immunogenicity and Optimize Function," Advanced Drug Delivery Review, 2006, vol. 58 (5-6), pp. 640-656.
Presta L.G., et al., "Humanization of an Antibody Directed Against IgE," Journal of Immunology, 1993, vol. 151 (5), pp. 2623-2632.
Presta L.G., "Molecular Engineering and Design of Therapeutic Antibodies," Current Opinion in Immunology, 2008, vol. 20(4), pp. 460-470.
Reck M., et al., "Advances in Anti-VEGF and Anti-EGFR Therapy for Advanced Non-small Cell Lung Cancer," Lung Cancer, 2009, vol. 63 (1), pp. 1-9.
Reers M., et al., "J-aggregate Formation of a Carbocyanine as a Quantitative Fluorescent Indicator of Membrane Potential," Biochemistry, May 1991, vol. 30 (18), pp. 4480-4486.
Reist C.J., et al., "Tumor-Specific Anti-Epidermal Growth Factor Receptor Variant III Monoclonal Antibodies: Use of the Tyramine-Cellobiose Radioiodination Method Enhances Cellular Retention and Uptake in Tumor Xenografts," Cancer Research, 1995, vol. 55 (19), pp. 4375-4382.
Reiter J.L, et al., "Comparative Genomic Sequence Analysis and Isolation of Human and Mouse Alternative EGFR Transcripts Encoding Truncated Receptor Isoforms," Genomics, 2001, vol. 71, pp. 1-20.
Remillard S., et al., "Antimitotic Activity of the Potent Tumor Inhibitor Maytansine," Science, 1975, vol. 189 (4207), pp. 1002-1005.
Riechmann L., et al., "Single Domain Antibodies: Comparison of Camel Vh and Camelised Human Vh Domains," Journal of Immunological Methods, 1999, vol. 231 (1-2), pp. 25-38.
Riechmann L., et al., "Reshaping Human Antibodies for Therapy," Nature, 1988, vol. 332 (6162), pp. 323-327.
Riemer A.B., et al., "Matching of TrastuzumAb (Herceptin) Epitope Mimics Onto the Surface of Her-2/neu—A New Method of Epitope Definition," Molecular Immunology, 2005, vol. 42, pp. 1121-1124.
Roberts D.D., et al., "Solvolysis Reactions: Relative Abilities of Cyclopentyl/Phenyl Groups to Stabilize an Electron-Deficient Carbon," The Journal of Organic Chemistry, 1994, vol. 59, pp. 6464-6469.
Robinson C., "Gene Therapy—Proceeding from Laboratory to Clinic," Trends in Biotechnology, 1993, vol. 11 (5), pp. 155-215.
Robinson J.R., "Sustained and Controlled Release Drug Delivery Systems," Marcel Dekker, Inc., 1978.

(56) References Cited

OTHER PUBLICATIONS

Robinson M.J., "Coating of Pharmaceutical Dosage Forms," Remington's Pharmaceutical Sciences, 1980, pp. 1585-1593, A. Osol, ed., Mack Publishing Co., Easton, Pa., (16th edition).
Rodrigues M.L., et al., "Synthesis and Beta-lactamase-mediated Activation of a Cephalosporin-Taxol Prodrug," Chemistry Biology, Apr. 1995, vol. 2 (4), pp. 223-227.
Roguska M.A., et al., "Humanization of Murine Monoclonal Antibodies through Variable Domain Resurfacing," Proceedings of the National Academy of Sciences of the United States America, Feb. 1994, vol. 91 (3), pp. 969-973.
Roth T.J., et al., "B7-H3 Ligand Expression by Prostate Cancer: a Novel Marker of Prognosis and Potential Target for Therapy," Cancer Research, Aug. 2007, vol. 67 (16), pp. 7893-7900.
Rudikoff S., et al., "Single Amino Acid Substitution Altering Antigen-binding Specificity," Proceedings of the National Academy of Sciences of the United States of America,1982, vol. 79 (6), pp. 1979-1983.
Ruvkun G., "Molecular Biology. Glimpses of a Tiny RNA World," Science, Oct. 2001, vol. 294 (5543), pp. 797-799.
Sakahara H., et al., "Effect of DTPA Conjugation on the Antigen Binding Activity and Biodistribution of Monoclonal Antibodies Against Alpha-Fetoprotein," Journal of Nuclear Medicine, 1985, vol. 26 (7), pp. 750-755.
Sakai K., et al., "Antitumor Principles in Mosses: the First Isolation and Identification of Maytansinoids, Including a Novel 15-methoxyansamitocin P-3," Journal of Natural Products, Sep.-Oct. 1988, vol. 51 (5), pp. 845-850.
Sampson J.H., et al., "Unarmed, Tumor-Specific Monoclonal Antibody Effectively Treats Brain Tumors," Proceedings of the National Academy of Sciences, 2000, vol. 97 (13), pp. 7503-7508.
Saudek C.D., et al., "A Preliminary Trial of the Programmable Implantable Medication System for Insulin Delivery," The New England Journal of Medicine, 1989, vol. 321 (9), pp. 574-579.
Schwechheimer K., et al., "EGFR Gene Amplification-Rearrangement in Human Glioblastomas," International Journal of Cancer, 1995, vol. 62 (2), pp. 145-148.
Scott A.M., et al., "A Phase I Clinical Trial with Monoclonal Antibody Ch806 Targeting Transitional State and Mutant Epidermal Growth Factor Receptors," Proceedings of the National Academy of Sciences, 2007, vol. 104 (10), pp. 4071-4076.
Sefton M.V., et al., "Implantable Pumps," Critical Reviews in Biomedical Engineering, 1987, vol. 14(3), pp. 201-240.
Sellei C., et al., "Clinical and Pharmacologic Experience with Dibromodulcitol (NSC-104800), a New Antitumor Agent," Cancer Chemotherapy Reports, Dec. 1969, vol. 53 (6), pp. 377-384.
Shamis M., et al., "Bioactivation of Self-Immolative Dendritic Prodrugs by Catalytic Antibody 38C2," Journal of the American Chemical Society, 2004, vol. 126 (6), pp. 1726-1731.
Shields R.L., et al., "Lack of Fucose on Human IgG1 N-Linked Oligosaccharide Improves Binding to Human FcγRIII and Antibody-Dependent Cellular Toxicity," The Journal of Biological Chemistry, Jul. 2002, vol. 277 (30), pp. 26733-26740.
Sims M.J., et al., "A Humanized CD18 Antibody can Block Function without Cell Destruction," Journal of Immunology, 1993, vol. 151 (4), pp. 2296-2308.
Sivasubramanian A., et al., "Structural Model of the mAb 806-EGFR Complex Using Computational Docking Followed by Computational and Experimental Mutagenesis," Structure, 2006, vol. 14, pp. 401-414.
Smiley S.T., et al., "Intracellular Heterogeneity in Mitochondrial Membrane Potentials Revealed by a J-aggregate-forming Lipophilic Cation JC-1," Proceedings of the National Academy of Sciences of the United States of America, May 1991, vol. 88 (9), pp. 3671-3675.
Smolen V.F., et al., "Controlled Drug Bioavailability: Drug Product Design and Performance," John Wiley & Sons, New York, 1984, vol. 1, Table of Contents.
Song Y.K., et al., "Antibody Mediated Lung Targeting of Long-Circulating Emulsions," PDA Journal of Pharmaceutical Science & Technology, Nov.-Dec. 1996, vol. 50 (6), pp. 372-377.

Stancoviski I., et al., "Mechanistic Aspects of the Opposing Effects of Monoclonal Antibodies to the ErbB2 Receptor on Tumor Growth," Proceedings of the National Academy of Sciences, 1991, vol. 88, pp. 8691-8695.
Steinberger P., et al., "Molecular Characterization of Human 4Ig-B7-H3, a Member of the B7 Family with Four Ig-like Domains," Journal of Immunology, Feb. 2004, vol. 172 (4), pp. 2352-2359.
Stewart, J.M., et al., Solid Phase Peptide Synthesis, 2nd Edition, The Pierce Chemical Co., Rockford, III, 1984.
Storm D.R., et al., "Effect of Small Changes in Orientation on Reaction Rate," Journal of the American Chemical Society, Aug. 1972, vol. 94 (16), pp. 5815-5825.
Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.
Sugawa N., et al., "Identical Splicing of Aberrant Epidermal Growth Factor Receptor Transcripts from Amplified Rearranged Genes in Human Glioblastomas," Proceedings of the National Academy of Sciences USA, 1990, vol. 87, pp. 8602-8606.
Sugimura K., "Japanese Review Article Human Antibody Engineering," Bio-Ventures, 2002, vol. 2 (4), pp. 30-33.
Suh W.K., et al., "The B7 Family Member B7-H3 Preferentially Down-regulates T Helper Type 1-mediated Immune Responses," Nature Immunology, Sep. 2003, vol. 4 (9), pp. 899-906.
Sun C., et al., "Enabling Scfvs as Multi-Drug Carriers: a Dendritic Approach," Bioorganic & Medicinal Chemistry, 2003, vol. 11 (8), pp. 1761-1768.
Sun C., et al., "Syntheses of Dendritic Linkers Containing Chlorambucil Residues for the Preparation of Antibody-Multidrug Immunoconjugates," Bioorganic & Medicinal Chemistry Letters, 2002, vol. 12 (16), pp. 2213-2215.
Sun Y., et al., "B7-H3 and B7-H4 Expression in Non-small-cell Lung Cancer," Lung Cancer, Aug. 2006, vol. 53 (2), pp. 143-151.
Supplementary European search report for Application No. EP14762617, dated Sep. 20, 2016, 8 pages.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suwanborirux K., et al., "Ansamitocin P-3, a Maytansinoid, From Claopodium Crispifolium and Anomodon Attenuatus or Associated Actinomycetes," Experientia, Jan. 1990, vol. 46 (1), pp. 117-120.
Suzuki A., et al., "Recent Advances in the Cross-Coupling Reactions of Organoboron Derivatives with Organic Electrophiles, 1995-1998," Journal of Organometallic Chemistry, 1999, vol. 576 (1-2), pp. 147-168.
Takeda S., et al., "Construction of Chimaeric Processed Immunoglobulin Genes Containing Mouse Variable and Human Constant Region Sequences," Nature, 1985, vol. 314 (6010), pp. 452-454.
Tao Z.F., et al., "Discovery of a Potent and Selective Bcl-xl Inhibitor With in Vivo Activity," ACS Medicinal Chemistry Letters, 2014, vol. 5 (10), pp. 1088-1093.
Teixeira S., et al., "Post-transcriptional Regulation of the Transferrin Receptor and 4F2 Antigen Heavy Chain mRNA During Growth Activation of Spleen Cells," European Journal of Biochemistry, Dec. 1991, vol. 202 (3), pp. 819-826.
Thorpe P.E., et al., "New Coupling Agents for the Synthesis of Immunotoxins Containing a Hindered Disulfide Bond with Improved Stability in Vivo," Cancer Research, Nov. 1987, vol. 47 (22), pp. 5924-5931.
Thorpe P.E., et al., "The Preparation and Cytotoxic Properties of Antibody-toxin Conjugates," Immunological Reviews, 1982, vol. 62, pp. 119-158.
Thorpe P.E. et al., "Antibody Carriers of Cytotoxic Agents in Cancer Therapy: A Review," in: Monoclonal Antibodies '84: Biological and Clinical Applications, 1985, pp. 474-512.
Tian F., et al., "A General Approach to Site-specific Antibody Drug Conjugates," Proceedings of the National Academy of Sciences of the United States of America, 2014, vol. 111 (5), pp. 1766-1771.

(56) References Cited

OTHER PUBLICATIONS

Toki B.E.., et al., "Protease-Mediated Fragmentation of p-Amidobenzyl Ethers: a New Strategy for the Activation of Anticancer Prodrugs," The Journal of Organic Chemistry, Mar. 2002, vol. 67(6), pp. 1866-1872.

Tolstoshev P., "Gene Therapy, Concepts, Current Trials and Future Directions," Annual Review of Pharmacology and Toxicology, 1993, vol. 32, pp. 573-596.

Tsao and Herbst "Factors That Determine Response to EGFR Inhibitors," Signal: The Journal of EGFR-targeted cancer therapy, 2003, vol. 4(4), pp. 4-9.

Tumey L.N., et al., "Mild Method for Succinimide Hydrolysis on ADSs: Impact on ADC Potency, Stability, Exposure, and Efficacy," Bioconjugate Chemistry, Oct. 2014, vol. 25 (10), pp. 1871-1880.

Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.

UniProtKB/Swiss-Prot Accession No. P00533.2, EGFr_Human, Sep. 29, 2021, Retrieved from internet URL: [https://www.ncbi.nlm.nih.gov/protein/2811086/], 43 pages.

Urlaub G., "Isolation of Chinese Hamster Cell Mutants Deficient in Dihydrofolate Reductase Activity," Proceedings of the National Academy of Sciences of the United States of America, 1980, vol. 77(7), pp. 4216-4220.

Vanantwerp J.J., et al., "Fine Affinity Discrimination by Yeast Surface Display and Flow Cytometry," Biotechnology Progress, 2000, vol. 16 (1), pp. 31-37.

Verhoeyen M., et al., "Reshaping Human Antibodies: Grafting an Antilysozyme Activity," Science, 1988, vol. 239 (4847), pp. 1534-1536.

Wahl R.L., et al., "Improved Radioimaging and Tumor Localization with Monoclonal F(Ab')2," Journal of Nuclear Medicine : Official Publication, Society of Nuclear Medicine, 1983, vol. 24 (4), pp. 316-325.

Walker J.R., et al., "Synthesis and Preliminary Chemotherapeutic Evaluation of the Fully C-linked Glucuronide of N-(4-hydroxyphenyl)retinamide," Bioorganic & Medicinal Chemistry, May 2006, vol. 14 (9), pp. 3038-3048.

Walker M.A., et al., "Monoclonal Antibody Mediated Intracellular Targeting of Tallysomycin S(10B)," Bioorganic & Medicinal Chemistry Letters, 2004, vol. 14 (16), pp. 4323-4327.

Walker M.A., et al., "Synthesis of an Immunoconjugate of Camptothecin," Bioorganic & Medicinal Chemistry Letters, 2002, vol. 12 (2), pp. 217-219.

Wallick S.C., et al., "Glycosylation of a VH Residue of a Monoclonal Antibody against Alpha (1—6) Dextran Increases its Affinity for Antigen," Journal of Experimental Medicine, 1988, vol. 168 (3), pp. 1099-1109.

Wang L., et al., "B7-H3 Promotes Acute and Chronic Allograft Rejection," European Journal of Immunology, Feb. 2005, vol. 35 (2), pp. 428-438.

Wang, Z. X., "An Exact Mathematical Expression for Describing Competitive Binding of Two Different Ligands to a Protein Molecule," FEBS Letters, 1995, vol. 360 (2), pp. 111-114.

Wani N.C., et al., "Plant Antitumor Agents: Colubrinol Acetate and Colubrinol, Antileukemic ansa Macrolides from Colubrina Texensis," Journal of the Chemical Society, Chemical Communications, 1973, vol. 390, pp. 1973.

Ward E.S., et al., "Binding Activities of a Repertoire of Single Immunoglobulin Variable Domains Secreted from *Escherichia coli*," Nature, 1989, vol. 341 (6242), pp. 544-546.

Wawrzynczak et al., "Antibody Conjugates in Radioimaging and Therapy of Cancer": in Immunoconjugates, Vogel C.W. ed., Oxford Univ. Press, 1987, 5 pages.

Wikstrand C.J., et al., "Cell Surface Localization and Density of the Tumor-Associated Variant of the Epidermal Growth Factor Receptor, EGFRvIII," Cancer Research, 1997, vol. 57, pp. 4130-4140.

Wikstrand C.J., et al., "Monoclonal Antibodies against EGFRvIII are Tumor Specific and React with Breast and Lung Carcinomas and Malignant Gliomas," Cancer Research, 1995, vol. 55 (14), pp. 3140-3148.

Wikstrand C.J., et al., "The Class III Variant of the Epidermal Growth Factor Receptor (EGFRvIII): Characterization and Utilization as an Immunotherapeutic Target," Journal of Neurovirology, 1998, vol. 4 (2), pp. 148-158.

Winnaker E.L., "From Genes to Clones: Introduction to Gene Technology," VCH Publishers, 1987, Table of Contents.

Wolfson W., et al., "Amber Codon Flashing Ambrx Augments Proteins with Unnatural Amino Acids," Chemistry & Biology, 2006, vol. 13 (10), pp. 1011-1012.

Wong A.J., et al., "Structural Alterations of the Epidermal Growth Factor Receptor Gene in Human Gliomas," Proceedings of the National Academy of Sciences USA, 1992, vol. 89, pp. 2965-2969.

Woodward J.R. Basic biotechnology; Edited by P Prave. U Faust, W Sittig and D A Sukatsch, VCH Verlagsgesellschaft, Weinheim, W Germany. 1987, pp. 344. ISBN 3-527-26678-X.

Wright A., et al., "Antibody Variable Region Glycosylation: Position Effects on Antigen Binding and Carbohydrate Structure," The EMBO Journal, 1991, vol. 10 (10), pp. 2717-2723.

Wu C.P., et al., "Relationship Between Co-stimulatory Molecule B7-H3 Expression and Gastric Carcinoma Histology and Prognosis," World Journal of Gastroenterology, Jan. 2006, vol. 12 (3), pp. 457-459.

Wu G.Y., et al., "Delivery Systems for Gene Therapy," Biotherapy, 1991, vol. 3 (1), pp. 87-95.

Wu G.Y., et al., "Receptor-mediated in Vitro Gene Transformation by a Soluble DNA Carrier System," Journal of Biological Chemistry, 1987, vol. 262 (10), pp. 4429-4432.

Wu H., et al., "Humanization of a Murine Monoclonal Antibody by Simultaneous Optimization of Framework and CDR Residues," Journal of Molecular Biology, 1999, vol. 294 (1), pp. 151-162.

Xu F., et al., "Antibody-Induced Growth Inhibition is Mediated through Immunochemically and Functionally Distinct Epitopes on the Extracellular Domain of the c-ErbB-2 (HER-2/neu) Gene Product p185," International Journal of Cancer, 1993, vol. 53, pp. 401-408.

Yamamoto Y., et al., "Radical Reaction Initiated and Stereocontrolled by Zinc Chloride," Heterocycles, 1998, vol. 47 (2), pp. 765-780.

Yamato I., et al., "Clinical Importance of B7-H3 Expression in Human Pancreatic Cancer," British Journal of Cancer, Nov. 2009, vol. 101 (10), pp. 1709-1716.

Yamazaki H., et al., "A Deletion Mutation within the Ligand Binding Domain is Responsible for Activation of Epidermal Growth Factor Receptor Gene in Human Brain Tumors," Japanese Journal of Cancer, 1990, vol. 81, pp. 773-779.

Yamazaki H., et al., "Amplification of the Structurally and Functionally Altered Epidermal Growth Factor Receptor Gene (c-erbB) in Human Brain Tumors," Molecular and Cellular Biology, 1988, vol. 8 (4), pp. 1816-1820.

Yanagida O., et al., "Human L-type Amino Acid Transporter 1 (LAT1): Characterization of Function and Expression in Tumor Cell Lines," Biochimica et Biophysica Acta, Oct. 2001, vol. 1514 (2), pp. 291-302.

Yang M., et al., "Direct Lactonization of 2-arylacetic Acids Through Pd(II)-catalyzed C-h Activation/c-o Formation," Organic Letters, 2013, vol. 15 (3), pp. 690-693.

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zamore P.D., "Ancient Pathways Programmed by Small RNAs," Science, May 2002, vol. 296 (5571), pp. 1265-1269.

Zeleznick L.D., et al., "Treatment of Leukemic (L-1210) Mice with Double-stranded Polyribonucleotides," Proceedings of the Society for Experimental Biology and Medicine, Jan. 1969, vol. 130 (1), pp. 126-128.

Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.

(56) References Cited

OTHER PUBLICATIONS

Zhang J.Y., et al., "Apoptosis-based Anticancer Drugs," Nature Reviews. Drug Discovery, Feb. 2002, vol. 1 (2), pp. 101-102.
Zhao R.Y., et al., "Synthesis and Evaluation of Hydrophilic Linkers for Antibody-Maytansinoid Conjugates," Journal of Medicinal Chemistry, 2011, vol. 54 (10), pp. 3606-3623.
Zuber J., et al., "RNAi Screen Identifies Brd4 as a Therapeutic Target in Acute Myeloid Leukaemia," Nature, 2011, vol. 478 (7370), pp. 524-528.
International Search Report and Written Opinion for Application No. PCT/US2022/13121, dated May 9, 2022, 13 pages.

* cited by examiner

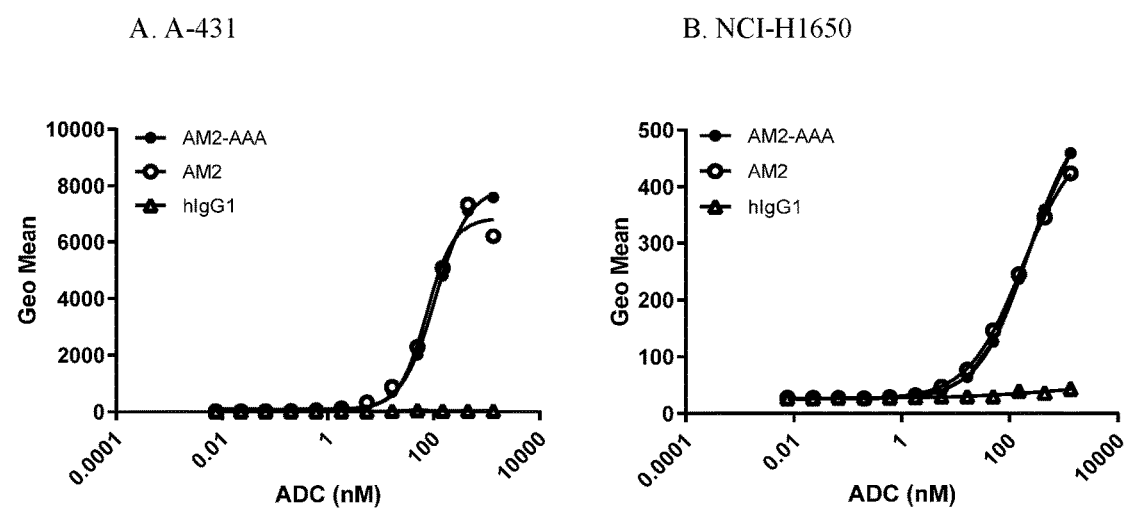
Figure 1: Binding of AM2-AAA, AM2 and MSL109 hIgG1, to A-431 and NCI-H1650 as assessed by FACS.

A. 431
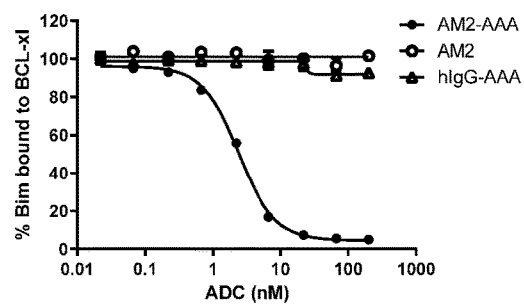
B. NCI-H1650
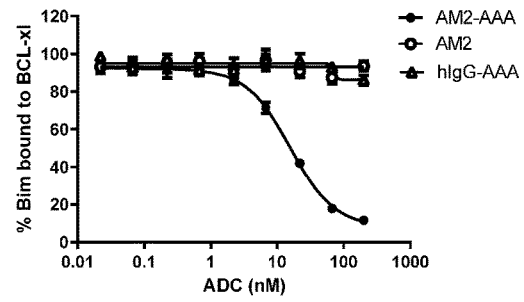
C. A431
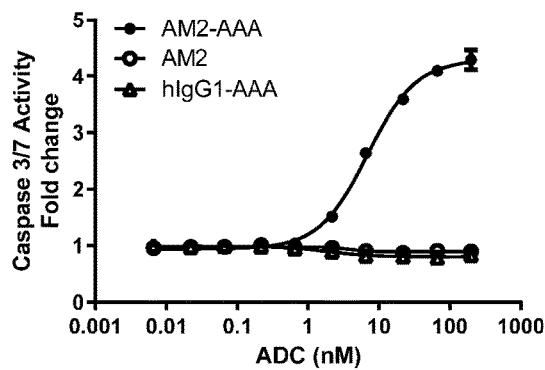
Figure 2: Disruption of Bcl-xL-BIM complexes in (A) A-431 and (B) NCI-H1650 cells following treatment with AM2-AAA, MSL109 hIgG-AAA or AM2. AM2-AAA disrupts BIM-Bcl-xL complexes and promotes caspase activation (C).

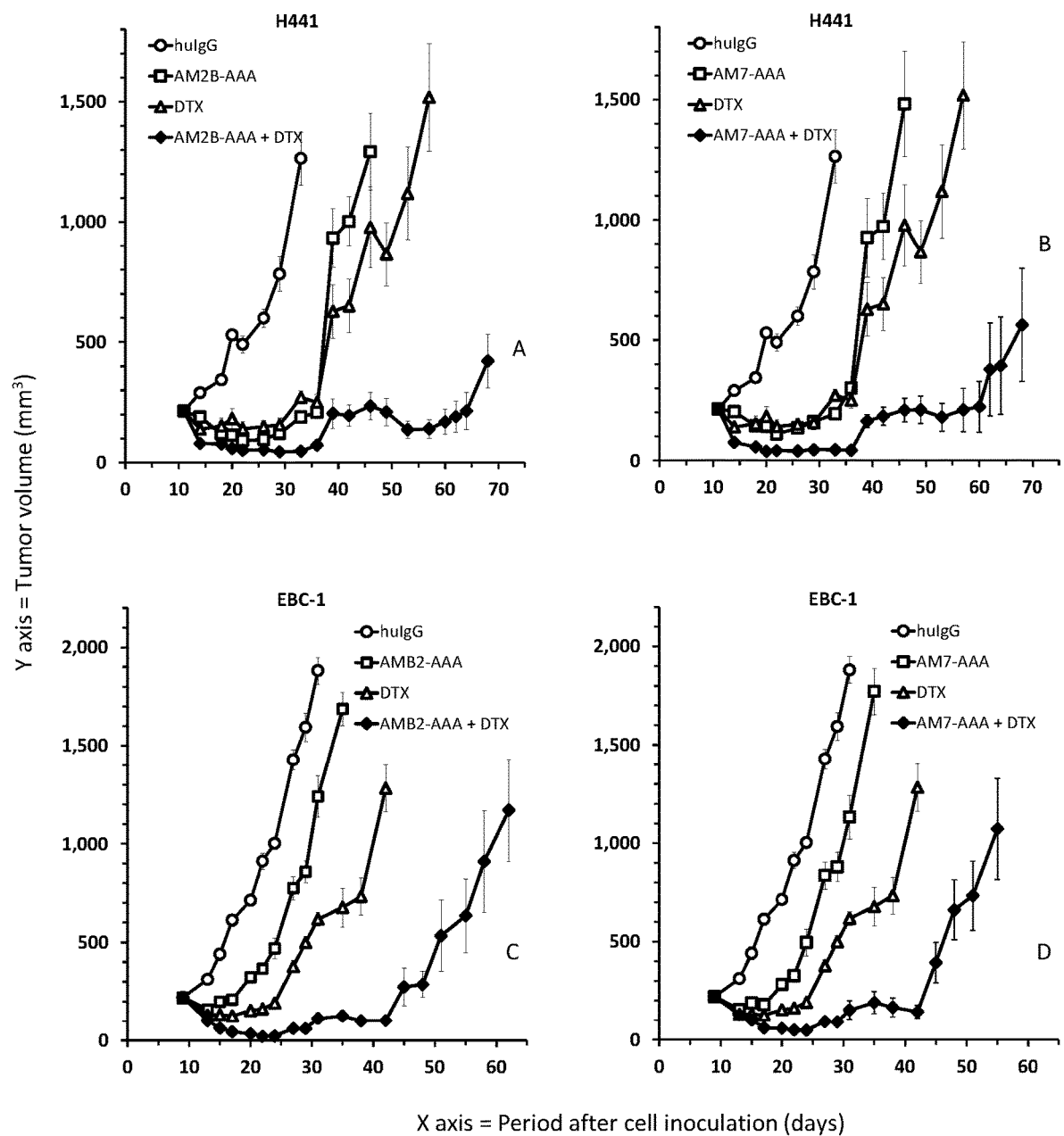
Figure 3: Inhibition of EBC-1 and H441 xenograft growth after treatment with AM2B-AAA, AM7-AAA, DTX and combinations of DTX with AM2B-AAA or AM7-AAA.

SEQUENCE LISTING

<160> NUMBER OF SEQ ID NOS: 32

<210> SEQ ID NO 1
<211> LENGTH: 446
<212> TYPE: PRT
<213> ORGANISM: Artificial
<220> FEATURE:
<223> OTHER INFORMATION: Synthetic Polypeptide

<400> SEQUENCE: 1

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Asn Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Lys Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Trp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 2
<211> LENGTH: 11
<212> TYPE: PRT
<213> ORGANISM: Artificial
<220> FEATURE:
<223> OTHER INFORMATION: Synthetic Polypeptide

<400> SEQUENCE: 2

Gly Tyr Ser Ile Ser Asn Asp Phe Ala Trp Asn
1               5                   10

<210> SEQ ID NO 3
<211> LENGTH: 16
<212> TYPE: PRT
<213> ORGANISM: Artificial
<220> FEATURE:
<223> OTHER INFORMATION: Synthetic Polypeptide

<400> SEQUENCE: 3

Tyr Ile Ser Tyr Lys Gly Asn Thr Arg Tyr Gln Pro Ser Leu Lys Ser
1               5                   10                  15

<210> SEQ ID NO 4
<211> LENGTH: 7
<212> TYPE: PRT
<213> ORGANISM: Artificial
<220> FEATURE:
<223> OTHER INFORMATION: Synthetic Polypeptide

<400> SEQUENCE: 4

Ala Ser Arg Gly Phe Pro Trp
1               5
```

```
<210> SEQ ID NO 5
<211> LENGTH: 214
<212> TYPE: PRT
<213> ORGANISM: Artificial
<220> FEATURE:
<223> OTHER INFORMATION: Synthetic Polypeptide

<400> SEQUENCE: 5

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210

<210> SEQ ID NO 6
<211> LENGTH: 11
<212> TYPE: PRT
<213> ORGANISM: Artificial
<220> FEATURE:
<223> OTHER INFORMATION: Synthetic Polypeptide

<400> SEQUENCE: 6

His Ser Ser Gln Asp Ile Asn Ser Asn Ile Gly
1               5                   10

<210> SEQ ID NO 7
<211> LENGTH: 7
<212> TYPE: PRT
<213> ORGANISM: Artificial
<220> FEATURE:
<223> OTHER INFORMATION: Synthetic Polypeptide

<400> SEQUENCE: 7

His Gly Thr Asn Leu Asp Asp
1               5
```

```
<210> SEQ ID NO 8
<211> LENGTH: 9
<212> TYPE: PRT
<213> ORGANISM: Artificial
<220> FEATURE:
<223> OTHER INFORMATION: Synthetic Polypeptide

<400> SEQUENCE: 8

Val Gln Tyr Ala Gln Phe Pro Trp Thr
1               5

<210> SEQ ID NO 9
<211> LENGTH: 446
<212> TYPE: PRT
<213> ORGANISM: Artificial
<220> FEATURE:
<223> OTHER INFORMATION: Synthetic Polypeptide

<400> SEQUENCE: 9

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Asn Asp
                20                  25                  30

Phe Ala Trp Asn Trp Ile Arg Gln Leu Pro Lys Gly Leu Glu Trp
            35                  40                  45

Met Gly Tyr Ile Ser Tyr Lys Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Leu Pro Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 10
<211> LENGTH: 7
<212> TYPE: PRT
<213> ORGANISM: Artificial
<220> FEATURE:
<223> OTHER INFORMATION: Synthetic Polypeptide

<400> SEQUENCE: 10

Ala Ser Arg Gly Leu Pro Tyr
1               5

<210> SEQ ID NO 11
<211> LENGTH: 214
<212> TYPE: PRT
<213> ORGANISM: Artificial
<220> FEATURE:
<223> OTHER INFORMATION: Synthetic Polypeptide

<400> SEQUENCE: 11

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Ile Gly Trp Leu Gln Gln Lys Pro Gly Lys Ser Phe Lys Gly Leu Ile
        35                  40                  45

Tyr His Gly Ala Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Glu Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Ala
    210

<210> SEQ ID NO 12
<211> LENGTH: 11
<212> TYPE: PRT
<213> ORGANISM: Artificial
<220> FEATURE:
<223> OTHER INFORMATION: Synthetic Polypeptide

<400> SEQUENCE: 12

His Ser Ser Gln Asp Ile Thr Tyr Asn Ile Gly
1               5                   10

<210> SEQ ID NO 13
<211> LENGTH: 7
<212> TYPE: PRT
<213> ORGANISM: Artificial
<220> FEATURE:
<223> OTHER INFORMATION: Synthetic Polypeptide

<400> SEQUENCE: 13

His Gly Ala Asn Leu Asp Asp
1               5

<210> SEQ ID NO 14
<211> LENGTH: 9
<212> TYPE: PRT
<213> ORGANISM: Artificial
<220> FEATURE:
<223> OTHER INFORMATION: Synthetic Polypeptide

<400> SEQUENCE: 14

Val Gln Tyr Asp Glu Phe Pro Trp Thr
1               5

<210> SEQ ID NO 15
<211> LENGTH: 1210
<212> TYPE: PRT
<213> ORGANISM: Artificial
<220> FEATURE:
<223> OTHER INFORMATION: Synthetic Polypeptide

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95
```

```
Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510
```

```
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
```

Lys Gly Glu Arg Leu Pro Gln Pro Pro Ile Cys Thr Ile Asp Val Tyr
          930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
              965                 970                 975

Arg Tyr Leu Val Ile Gln Gly Asp Glu Arg Met His Leu Pro Ser Pro
              980                 985                 990

Thr Asp Ser Asn Phe Tyr Arg Ala Leu Met Asp Glu Glu Asp Met Asp
          995                 1000                1005

Asp Val Val Asp Ala Asp Glu Tyr Leu Ile Pro Gln Gln Gly Phe
      1010                1015                1020

Phe Ser Ser Pro Ser Thr Ser Arg Thr Pro Leu Leu Ser Ser Leu
      1025                1030                1035

Ser Ala Thr Ser Asn Asn Ser Thr Val Ala Cys Ile Asp Arg Asn
      1040                1045                1050

Gly Leu Gln Ser Cys Pro Ile Lys Glu Asp Ser Phe Leu Gln Arg
      1055                1060                1065

Tyr Ser Ser Asp Pro Thr Gly Ala Leu Thr Glu Asp Ser Ile Asp
      1070                1075                1080

Asp Thr Phe Leu Pro Val Pro Glu Tyr Ile Asn Gln Ser Val Pro
      1085                1090                1095

Lys Arg Pro Ala Gly Ser Val Gln Asn Pro Val Tyr His Asn Gln
      1100                1105                1110

Pro Leu Asn Pro Ala Pro Ser Arg Asp Pro His Tyr Gln Asp Pro
      1115                1120                1125

His Ser Thr Ala Val Gly Asn Pro Glu Tyr Leu Asn Thr Val Gln
      1130                1135                1140

Pro Thr Cys Val Asn Ser Thr Phe Asp Ser Pro Ala His Trp Ala
      1145                1150                1155

Gln Lys Gly Ser His Gln Ile Ser Leu Asp Asn Pro Asp Tyr Gln
      1160                1165                1170

Gln Asp Phe Phe Pro Lys Glu Ala Lys Pro Asn Gly Ile Phe Lys
      1175                1180                1185

Gly Ser Thr Ala Glu Asn Ala Glu Tyr Leu Arg Val Ala Pro Gln
      1190                1195                1200

Ser Ser Glu Phe Ile Gly Ala
      1205                1210

<210> SEQ ID NO 16
<211> LENGTH: 525
<212> TYPE: PRT
<213> ORGANISM: Artificial
<220> FEATURE:
<223> OTHER INFORMATION: Synthetic Polypeptide

<400> SEQUENCE: 16

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480
```

```
Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser
        515                 520                 525

<210> SEQ ID NO 17
<211> LENGTH: 645
<212> TYPE: PRT
<213> ORGANISM: Artificial
<220> FEATURE:
<223> OTHER INFORMATION: Synthetic Polypeptide

<400> SEQUENCE: 17

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320
```

```
Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser
            645

<210> SEQ ID NO 18
<211> LENGTH: 943
<212> TYPE: PRT
<213> ORGANISM: Artificial
<220> FEATURE:
<223> OTHER INFORMATION: Synthetic Polypeptide

<400> SEQUENCE: 18

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30
```

Val Val Thr Asp His Gly Ser Cys Val Arg Ala Cys Gly Ala Asp Ser
                35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
            115                 120                 125

Lys Thr Val Lys Glu Ile Thr Gly Phe Leu Leu Ile Gln Ala Trp Pro
130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
            195                 200                 205

Asn Trp Lys Lys Leu Phe Gly Thr Ser Gly Gln Lys Thr Lys Ile Ile
            210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
                260                 265                 270

Asn Leu Leu Glu Gly Glu Pro Arg Glu Phe Val Glu Asn Ser Glu Cys
            275                 280                 285

Ile Gln Cys His Pro Glu Cys Leu Pro Gln Ala Met Asn Ile Thr Cys
            290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
            355                 360                 365

Cys Pro Thr Asn Gly Pro Lys Ile Pro Ser Ile Ala Thr Gly Met Val
            370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
            435                 440                 445

```
Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
    610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
    690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
    770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860
```

```
Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
            885                 890                 895

Gln Ile Ser Leu Asp Asn Pro Asp Tyr Gln Gln Asp Phe Phe Pro Lys
        900                 905                 910

Glu Ala Lys Pro Asn Gly Ile Phe Lys Gly Ser Thr Ala Glu Asn Ala
    915                 920                 925

Glu Tyr Leu Arg Val Ala Pro Gln Ser Ser Glu Phe Ile Gly Ala
930                 935                 940

<210> SEQ ID NO 19
<211> LENGTH: 350
<212> TYPE: PRT
<213> ORGANISM: Artificial
<220> FEATURE:
<223> OTHER INFORMATION: Synthetic Polypeptide

<400> SEQUENCE: 19

Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
        35                  40                  45

Ile Gly Ile Gly Glu Phe Lys Asp Ser Leu Ser Ile Asn Ala Thr Asn
    50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
        115                 120                 125

Phe Glu Asn Leu Glu Ile Ile Arg Gly Arg Thr Lys Gln His Gly Gln
    130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205

Lys Ala Thr Gly Gln Val Cys His Ala Leu Cys Ser Pro Glu Gly Cys
    210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
                245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
        275                 280                 285
```

```
Ile Gln Cys Ala His Tyr Ile Asp Gly Pro His Cys Val Lys Thr Cys
    290                 295                 300
Pro Ala Gly Val Met Gly Glu Asn Asn Thr Leu Val Trp Lys Tyr Ala
305                 310                 315                 320
Asp Ala Gly His Val Cys His Leu Cys His Pro Asn Cys Thr Tyr Gly
                325                 330                 335
Cys Thr Gly Pro Gly Leu Glu Gly Cys Pro Thr Asn Gly Pro
                340                 345                 350

<210> SEQ ID NO 20
<211> LENGTH: 16
<212> TYPE: PRT
<213> ORGANISM: Artificial
<220> FEATURE:
<223> OTHER INFORMATION: Synthetic Polypeptide

<400> SEQUENCE: 20

Cys Gly Ala Asp Ser Tyr Glu Met Glu Glu Asp Gly Val Arg Lys Cys
1               5                   10                  15

<210> SEQ ID NO 21
<211> LENGTH: 446
<212> TYPE: PRT
<213> ORGANISM: Artificial
<220> FEATURE:
<223> OTHER INFORMATION: Synthetic Polypeptide

<400> SEQUENCE: 21

Glu Val Gln Leu Gln Glu Ser Gly Pro Gly Leu Val Lys Pro Ser Gln
1               5                   10                  15
Thr Leu Ser Leu Thr Cys Thr Val Ser Gly Tyr Ser Ile Ser Asn Asp
                20                  25                  30
Phe Ala Trp Asn Trp Ile Arg Gln Pro Pro Gly Lys Gly Leu Glu Trp
            35                  40                  45
Met Gly Tyr Ile Ser Tyr Lys Gly Asn Thr Arg Tyr Gln Pro Ser Leu
    50                  55                  60
Lys Ser Arg Ile Thr Ile Ser Arg Asp Thr Ser Lys Asn Gln Phe Phe
65                  70                  75                  80
Leu Lys Leu Asn Ser Val Thr Ala Ala Asp Thr Ala Thr Tyr Tyr Cys
                85                  90                  95
Val Thr Ala Ser Arg Gly Phe Pro Trp Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 22
<211> LENGTH: 116
<212> TYPE: PRT
<213> ORGANISM: Artificial
<220> FEATURE:
<223> OTHER INFORMATION: Synthetic Polypeptide

<400> SEQUENCE: 22

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Asn Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Lys Gly Asn Thr Arg Tyr Gln Pro Ser Leu
    50                  55                  60

Lys Ser Arg Ile Thr Ile Ser Arg Asp Thr Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Trp Trp Gly Gln Gly Thr Leu Val
            100                 105                 110

Thr Val Ser Ser
        115

<210> SEQ ID NO 23
<211> LENGTH: 107
<212> TYPE: PRT
<213> ORGANISM: Artificial
```

<220> FEATURE:
<223> OTHER INFORMATION: Synthetic Polypeptide

<400> SEQUENCE: 23

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 24
<211> LENGTH: 214
<212> TYPE: PRT
<213> ORGANISM: Artificial
<220> FEATURE:
<223> OTHER INFORMATION: Synthetic Polypeptide

<400> SEQUENCE: 24

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 19
<212> TYPE: PRT
<213> ORGANISM: Artificial
<220> FEATURE:
<223> OTHER INFORMATION: Synthetic Polypeptide

<400> SEQUENCE: 25

Met Glu Phe Gly Leu Ser Trp Leu Phe Leu Val Ala Ile Leu Lys Gly
1               5                   10                  15

Val Gln Cys

<210> SEQ ID NO 26
<211> LENGTH: 22
<212> TYPE: PRT
<213> ORGANISM: Artificial
<220> FEATURE:
<223> OTHER INFORMATION: Synthetic Polypeptide

<400> SEQUENCE: 26

Met Asp Met Arg Val Pro Ala Gln Leu Leu Gly Leu Leu Leu Leu Trp
1               5                   10                  15

Phe Pro Gly Ser Arg Cys
            20

<210> SEQ ID NO 27
<211> LENGTH: 673
<212> TYPE: PRT
<213> ORGANISM: Artificial
<220> FEATURE:
<223> OTHER INFORMATION: Synthetic Polypeptide

<400> SEQUENCE: 27

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

```
Lys Leu Thr Lys Ile Ile Cys Ala Gln Gln Cys Ser Gly Arg Cys Arg
    210             215                 220

Gly Lys Ser Pro Ser Asp Cys Cys His Asn Gln Cys Ala Ala Gly Cys
225             230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260             265             270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290             295                 300

Gly Ser Cys Val Arg Ala Cys Gly Ala Asp Ser Tyr Glu Met Glu Glu
305             310              315                 320

Asp Gly Val Arg Lys Cys Lys Lys Cys Glu Gly Pro Cys Arg Lys Val
                325             330                 335

Cys Asn Gly Ile Gly Ile Gly Glu Phe Lys Asp Ser Leu Ser Ile Asn
            340             345                 350

Ala Thr Asn Ile Lys His Phe Lys Asn Cys Thr Ser Ile Ser Gly Asp
            355             360                 365

Leu His Ile Leu Pro Val Ala Phe Arg Gly Asp Ser Phe Thr His Thr
    370             375                 380

Pro Pro Leu Asp Pro Gln Glu Leu Asp Ile Leu Lys Thr Val Lys Glu
385             390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620
```

```
Thr Tyr Gly Cys Thr Gly Pro Gly Leu Glu Gly Cys Pro Thr Asn Gly
625                 630                 635                 640

Pro Lys Ile Pro Ser Leu Glu Ser Arg Gly Pro Phe Glu Gln Lys Leu
            645                 650                 655

Ile Ser Glu Glu Asp Leu Asn Met His Thr Gly His His His His His
            660                 665                 670

His
```

<210> SEQ ID NO 28
<211> LENGTH: 553
<212> TYPE: PRT
<213> ORGANISM: Artificial
<220> FEATURE:
<223> OTHER INFORMATION: Synthetic Polypeptide
<400> SEQUENCE: 28

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300
```

Gly Ser Cys Val Arg Ala Cys Gly Ala Asp Ser Tyr Glu Met Glu
305                 310                 315                 320

Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Leu Glu Ser
            515                 520                 525

Arg Gly Pro Phe Glu Gln Lys Leu Ile Ser Glu Glu Asp Leu Asn Met
            530                 535                 540

His Thr Gly His His His His His His
545                 550

<210> SEQ ID NO 29
<211> LENGTH: 460
<212> TYPE: PRT
<213> ORGANISM: Artificial
<220> FEATURE:
<223> OTHER INFORMATION: Synthetic Polypeptide

<400> SEQUENCE: 29

Glu Glu Gln Val Leu Glu Ser Gly Gly Gly Leu Val Lys Pro Gly Gly
1               5                   10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
        35                  40                  45

Ser Ser Ile Asn Ser Asp Ser Thr Tyr Lys Tyr Ala Asp Ser Val
    50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Ala Phe Ser Ser Gly Ser Leu Ser Asp
            100                 105                 110

```
Tyr Tyr Tyr Gly Leu Asp Val Trp Gly Gln Gly Thr Thr Val Ile Val
            115                 120                 125

Ser Ser Ala Ser Thr Lys Gly Pro Ser Val Phe Pro Leu Ala Pro Ser
130             135                 140

Ser Lys Ser Thr Ser Gly Gly Thr Ala Ala Leu Gly Cys Leu Val Lys
145             150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
            210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 30
<211> LENGTH: 219
<212> TYPE: PRT
<213> ORGANISM: Artificial
<220> FEATURE:
<223> OTHER INFORMATION: Synthetic Polypeptide

<400> SEQUENCE: 30

Asp Ile Val Met Thr Gln Ser Pro Leu Ser Leu Ser Val Thr Pro Gly
1               5                   10                  15
```

```
Glu Pro Ala Ser Ile Ser Cys Arg Ser Ser Gln Ser Leu Leu His Thr
                20                  25                  30

Asn Gly Tyr Asn Tyr Leu Asp Trp Tyr Val Gln Lys Pro Gly Gln Ser
            35                  40                  45

Pro Gln Leu Leu Ile Tyr Leu Ala Ser Asn Arg Ala Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Thr Glu Asp Val Gly Val Tyr Tyr Cys Met Gln Ala
                85                  90                  95

Leu Gln Ile Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 31
<211> LENGTH: 406
<212> TYPE: PRT
<213> ORGANISM: Artificial
<220> FEATURE:
<223> OTHER INFORMATION: Synthetic Polypeptide

<400> SEQUENCE: 31

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
            35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
 65                 70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160
```

```
Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Leu Glu Ser Arg Gly Pro
    370                 375                 380

Phe Glu Gln Lys Leu Ile Ser Glu Glu Asp Leu Asn Met His Thr Gly
385                 390                 395                 400

His His His His His His
                405

<210> SEQ ID NO 32
<211> LENGTH: 24
<212> TYPE: PRT
<213> ORGANISM: Artificial
<220> FEATURE:
<223> OTHER INFORMATION: Synthetic Polypeptide

<400> SEQUENCE: 32

Met Arg Pro Ser Gly Thr Ala Gly Ala Ala Leu Leu Ala Leu Leu Ala
1               5                   10                  15

Ala Leu Cys Pro Ala Ser Arg Ala
            20
```

ANTI-EGFR ANTIBODY-DRUG CONJUGATES

RELATED APPLICATIONS

This application claims the benefit of priority to U.S. Provisional Patent Application Ser. No. 63/139,766, filed Jan. 20, 2021.

SEQUENCE LISTING

The instant application contains a Sequence Listing which has been submitted electronically in ASCII format and is hereby incorporated by reference in its entirety. Said ASCII copy, created on Oct. 12, 2022, is named ABV12608USO1_SequenceListing_ST25.txt and is 74,973 bytes in size.

FIELD OF THE INVENTION

The present application pertains to novel anti-Epidermal Growth Factor Receptor (EGFR) antibody drug conjugates (ADCs) which inhibit Bcl-xL, including compositions and methods using such ADCs, and methods for making such ADCs.

BACKGROUND

The human epidermal growth factor receptor (also known as HER-1 or Erb-B 1 and referred to herein as "EGFR") is a 170 kDa transmembrane receptor encoded by the c-erbB protooncogene. (Modjtahedi et al., Br. J. Cancer 73:228-235 (1996); Herbst and Shin, Cancer 94:1593-1611 (2002)). SwissProt database entry P00533 provides the sequence of human EGFR.

Ligand binding by EGFR triggers receptor homo- and/or heterodimerization and autophosphorylation of key cytoplasmic residues and MUC 1. Phosphorylated EGFR activates complex downstream signaling cascades. Overexpression of EGFR has been reported in numerous human malignant conditions and associated with poor prognosis with patients. (Herbst and Shin, Cancer 94:1593-1611 (2002); and Modjtahedi et al., Br. J. Cancer 73:228-235 (1996)).

Antibody drug conjugates represent a class of therapeutics comprising an antibody conjugated to a cytotoxic drug via a chemical linker. Designing ADCs against EGFR has been challenging, because of cutaneous EGFR expression and the known skin toxicity of EGFR-directed antibodies. Anti-EGFR antibodies and antibody-drug conjugates are also described in U.S. Pat. No. 9,493,568 and U.S. Patent Application Publication No. 2019/0343961, which are incorporated by reference herein in their entireties. A first generation of EGFR ADCs was depatuxizumab mafodotin, which uses the maleimidocaproyl linker and microtubule cytotoxin monomethyl auristatin F (MMAF). However, patients receiving depatux-m have experienced frequent ocular side effects (e.g., dry eyes, blurry vision, eye pain, photophobia, keratitis, corneal deposits, and watery eyes).

Given the ocular toxicity of depatux-m, a second-generation ADC targeting EGFR, losatuxizumab vedotin, was conjugated to a different toxin. The antibody component of this ADC, losatuxizumab, was affinity matured so that it had a higher affinity for EGFR (both wild-type and mutant) compared with depatux-m. However, the relatively high frequency of infusion reactions necessitated the early closure of the losatuxizumab vedotin phase 1 trial. See Cleary et al., Investigational New Drugs 38, 1483-1494 (2020).

Accordingly, there is a need for the development of new anti-EGFR ADCs, and in particular EGFR ADCs that can selectively deliver Bcl-xL to target cancer cells (e.g., EGFRvIII expressing cells), represents a significant discovery.

SUMMARY

One aspect pertains to an anti-human epidermal growth factor receptor (hEGFR) antibody drug conjugate comprising the structure of Formula (I) conjugated to an antibody Ab:

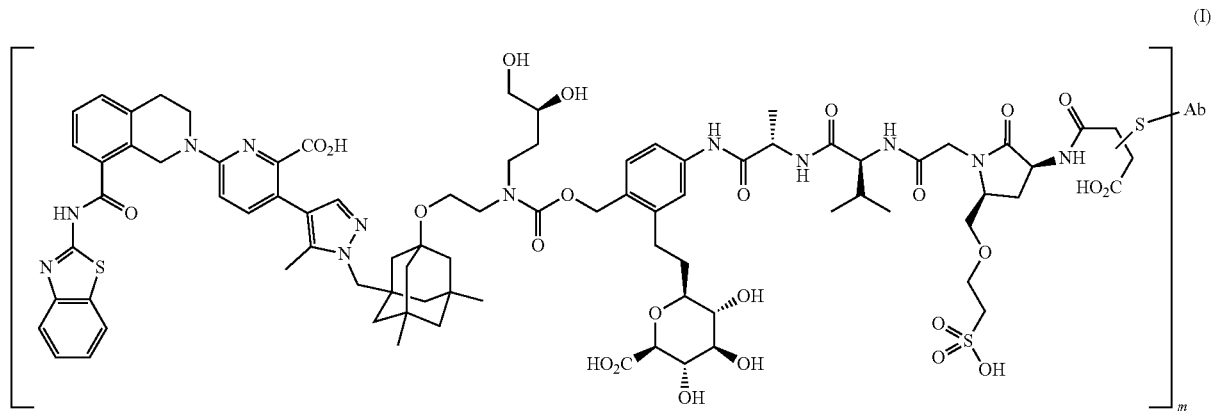

(I)

wherein Ab is an IgG1 anti-hEGFR antibody comprising a heavy chain comprising the amino acid sequence set forth as SEQ ID NO: 1 and a light chain comprising the amino acid sequence set forth as SEQ ID NO: 5; and wherein m is 2. In embodiments, the structure of Formula (I) is conjugated to the antibody Ab through C220 of the heavy chain (i.e., C219 of SEQ ID NO: 1). In embodiments, the present disclosure provides methods of using the anti-EGFR antibody drug conjugate for treating non-small cell lung cancer. In embodiments, the present disclosure provides pharmaceutical compositions comprising said anti-hEGFR antibody drug conjugate.

Another aspect pertains to an anti-human Epidermal Growth Factor Receptor antibody-drug conjugate comprising the structure of formula (II) conjugated to an antibody Ab:

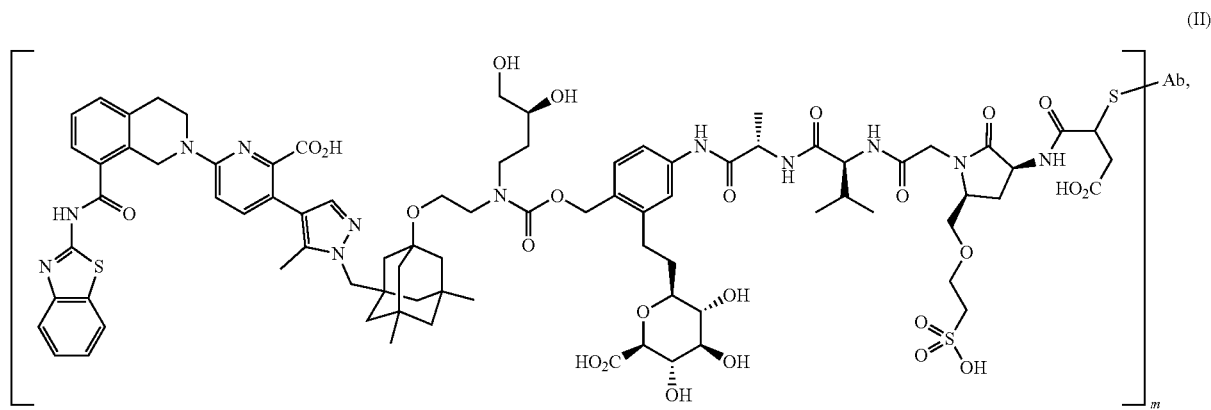

(II)

wherein Ab is an IgG1 anti-human epidermal growth factor receptor antibody comprising a heavy chain comprising the amino acid sequence set forth as SEQ ID NO: 1 and a light chain comprising the amino acid sequence set forth as SEQ ID NO: 5, and wherein m is 2. In embodiments, the structure of Formula (II) is conjugated to the antibody Ab through C220 of the heavy chain (i.e., C219 of SEQ ID NO: 1). In embodiments, the present disclosure provides methods of using the anti-EGFR antibody drug conjugate for treating non-small cell lung cancer. In embodiments, the present disclosure provides pharmaceutical compositions comprising said anti-hEGFR antibody drug conjugate.

Another aspect pertains to an anti-human Epidermal Growth Factor Receptor antibody-drug conjugate comprising the structure of formula (III) conjugated to an antibody Ab:

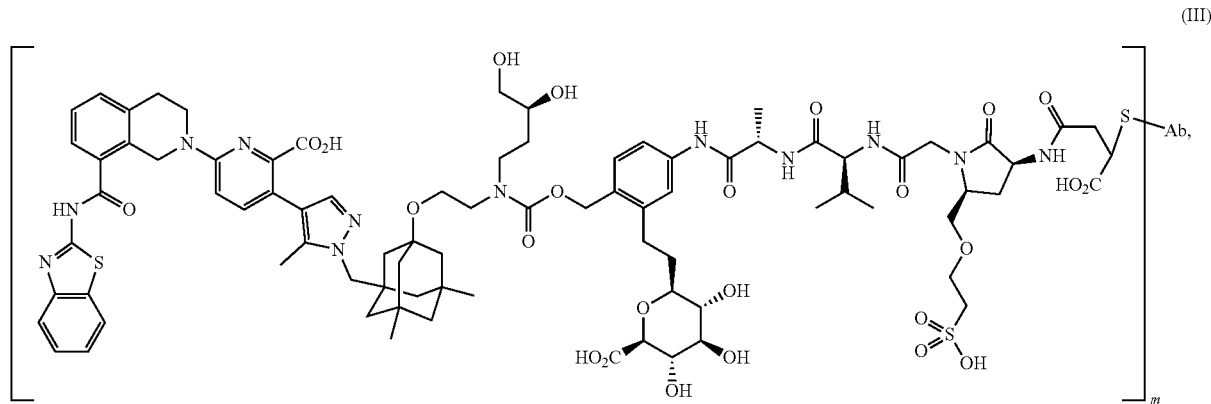

(III)

wherein Ab is an IgG1 anti-human epidermal growth factor receptor antibody comprising a heavy chain comprising the amino acid sequence set forth as SEQ ID NO: 1 and a light chain comprising the amino acid sequence set forth as SEQ ID NO: 5; and wherein m is 2. In embodiments, the structure of Formula (III) is conjugated to the antibody Ab through C220 of the heavy chain (i.e., C219 of SEQ ID NO: 1). In embodiments, the present disclosure provides methods of using the anti-EGFR antibody drug conjugate for treating non-small cell lung cancer. In embodiments, the present disclosure provides pharmaceutical compositions comprising said anti-hEGFR antibody drug conjugate.

Another aspect pertains to a method of producing an antibody drug conjugate (ADC) comprising a step of conjugating a monoclonal human IgG$_1$ anti-EGFR antibody with a synthon comprising the structure (AAA):

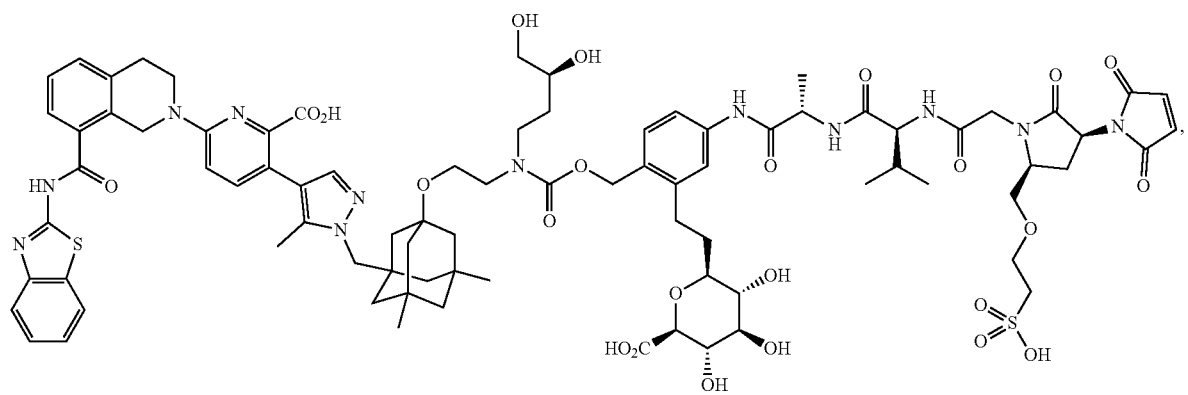

(IV)

to form an antibody-drug conjugate comprising a drug-linker conjugated to the anti-EGFR antibody, wherein the anti-EGFR antibody comprises a heavy chain comprising the amino acid sequence set forth as SEQ ID NO: 1 and a light chain comprising the amino acid sequence set forth as SEQ ID NO: 5. In embodiments, the drug-linker is conjugated to the antibody through C220 of the heavy chain (i.e., C219 of SEQ ID NO: 1).

Another aspect pertains to a process for the preparation of an antibody drug conjugate (ADC) according to Formula (I):

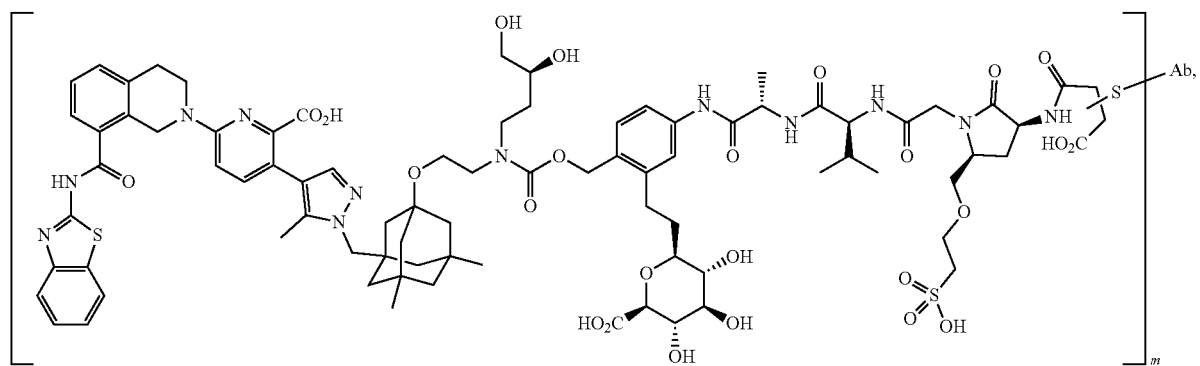

(I)

wherein Ab is an IgG1 anti-human epidermal growth factor receptor antibody comprising a heavy chain comprising the amino acid sequence set forth as SEQ ID NO: 1 and a light chain comprising the amino acid sequence set forth as SEQ ID NO: 5; and m is 2;

the process comprising:

treating an antibody in a buffered aqueous solution with an effective amount of a disulfide reducing agent for about 16-24 hours;

adding to the reduced antibody solution a solution of dimethyl acetamide comprising a synthon having the following structure:

at about 4° C. for about 16-24 hours. In embodiments, the reduced antibody is added to the solution of dimethyl acetamide comprising the synthon, and the reaction is allowed to run for about 60 minutes to form the ADC. In embodiments, after the ADC is formed, the reaction is quenched with about 2 equivalents of N-acetyl-L-cysteine. In embodiments, the process further comprises purifying with hydrophobic interaction chromatography (HIC). In embodiments, the process further comprises hydrolyzing the succinimide with a pH buffer, such as a pH buffer of about (IV)

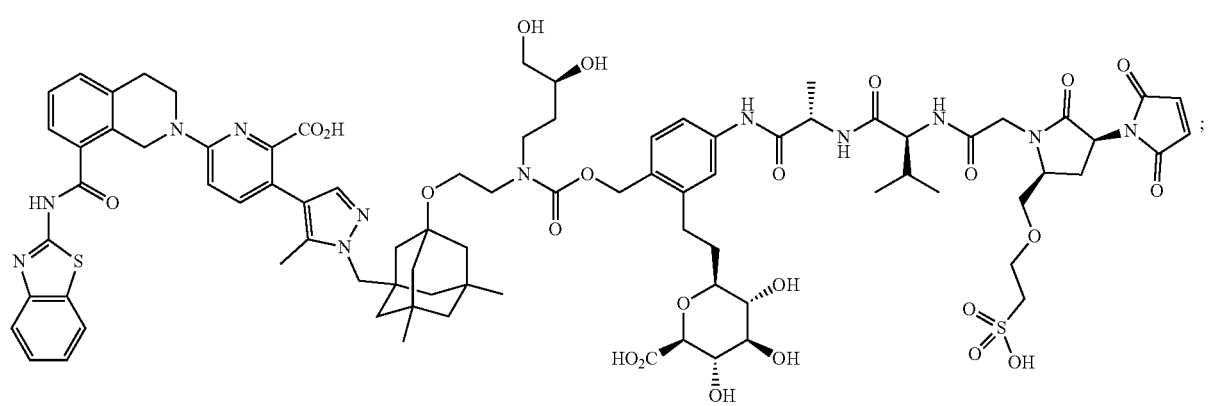

allowing the reaction to run to form the ADC;

wherein the mass is shifted by 18±2 amu for each hydrolysis of a succinimide to a succinamide as measured by electron spray mass spectrometry; and wherein the ADC is optionally purified by hydrophobic interaction chromatography (HIC). In embodiments, the buffered aqueous solution is a buffered aqueous solution of about pH 7.4. In embodiments, the antibody is treated with the disulfide reducing agent in the buffered aqueous solution 8-9. In embodiments, the process further comprises purifying with tangential flow filtration (TFF). In embodiments, the linker-drug is conjugated to the anti-EGFR antibody Ab through C220 of the heavy chain (i.e., C219 of SEQ ID NO: 1).

Another aspect pertains to an antibody-drug conjugate (ADC) prepared by a method comprising a step of conjugating a monoclonal human IgG$_1$ anti-EGFR antibody with a synthon comprising the structure:

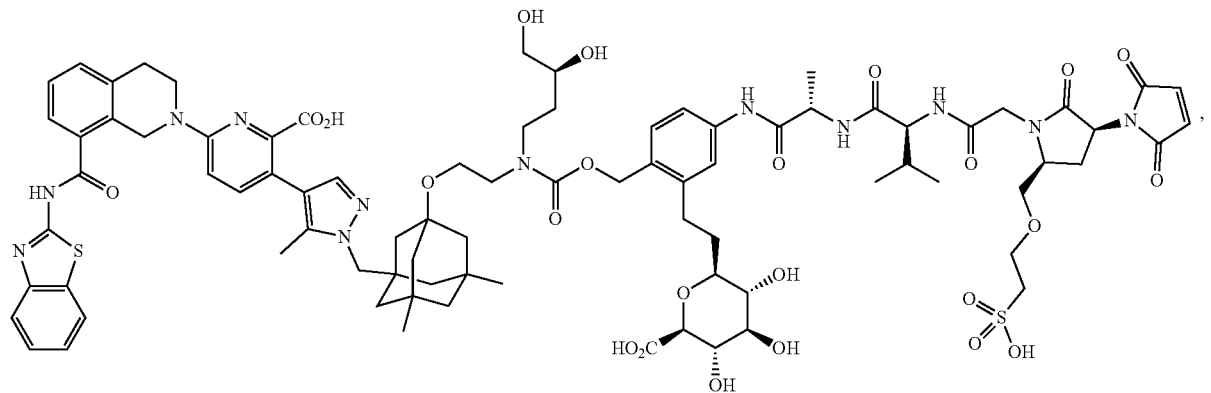

wherein the antibody comprises a heavy chain comprising the amino acid sequence set forth as SEQ ID NO: 1 and a light chain comprising the amino acid sequence set forth as SEQ ID NO: 5. In embodiments, the drug-linker is conjugated to the anti-EGFR antibody through C220 of the heavy chain (i.e., C219 of SEQ ID NO: 1).

Another aspect pertains to a process for the preparation of an antibody drug conjugate (ADC) according to Formula (I):

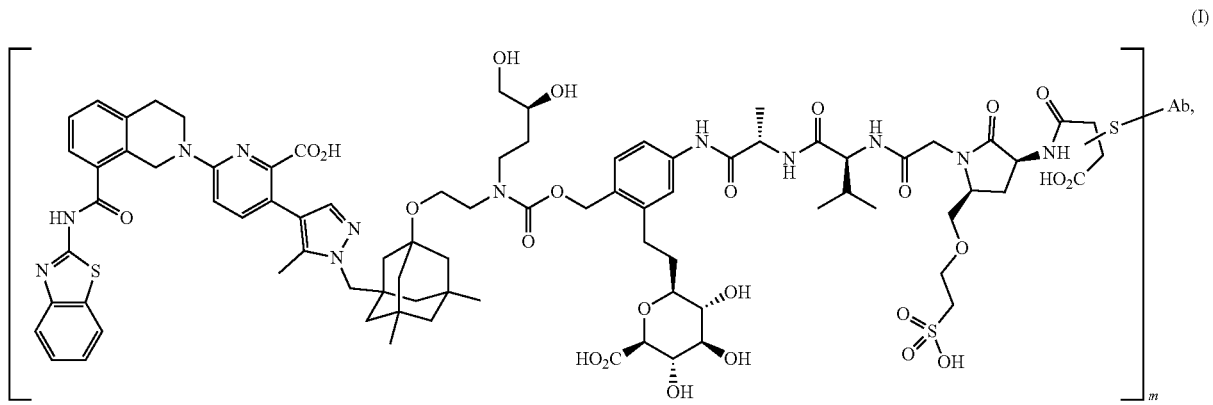

(I)

wherein Ab is an IgG1 anti-human epidermal growth factor receptor antibody comprising a heavy chain comprising the amino acid sequence set forth as NO: 1 and a light chain comprising the amino acid sequence set forth as SEQ ID NO: 5; and m is 2;

the process comprising:

treating an antibody in a buffered aqueous solution of about pH 7.4 with an effective amount of a disulfide reducing agent at about 4° C. for about 16-24 hours;

allowing the reduced antibody solution to warm to ambient temperature;

adding to the reduced antibody solution a solution of dimethyl acetamide comprising a synthon having the following structure:

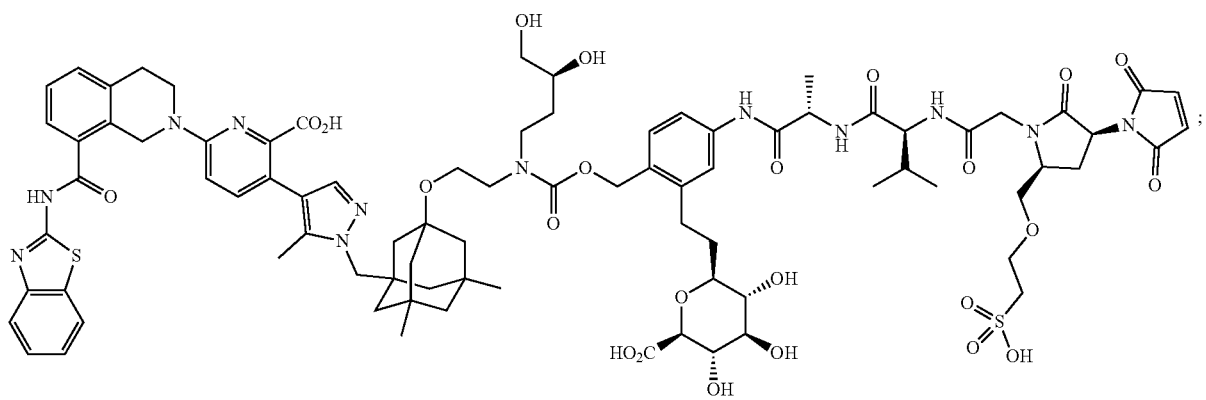

(IV)

allowing the reaction to run for about 60 minutes to form the ADC;

quenching with about 2 equivalents of N-acetyl-L-cysteine;

purifying with hydrophobic interaction Chromatography (HIC);

purifying with tangential flow filtration (TFF);

hydrolyzing the succinimide with a pH buffer of about 8-9; and purifying with tangential flow filtration (TFF);

wherein the mass is shifted by 18±2 amu for each hydrolysis of a succinimide to a succinamide as measured by electron spray mass spectrometry; and wherein the ADC is optionally purified by hydrophobic interaction chromatography. In embodiments, the linker-drug is conjugated to the anti-EGFR antibody through C220 of the heavy chain (i.e., C219 of SEQ ID NO: 1).

BRIEF DESCRIPTION OF THE DRAWINGS

FIG. 1 shows binding of AM2-AAA, AM2, and MSL109 hIgG1, to (A) A-431 (human epidermoid carcinoma) and (B) NCI-H1650 (non-small cell lung cancer) as assessed by FACS.

FIG. 2 shows AM2-AAA disrupts BIM-Bcl-xL complexes and promotes caspase activation and disruption of Bcl-xL-BIM complexes in (A) A-431 (human epidermoid carcinoma) and (B) NCI-H1650 (non-small cell lung cancer) cells following treatment with AM2-AAA, MSL109 hIgG-AAA or AM2.

FIG. 3 shows inhibition of EBC-1 (human lung squamous cell carcinoma) and H441 (human lung adenocarcinoma) xenograft growth after treatment with (A, H441; and C, EBC-1) AM2B-AAA, (B, H441; and D, EBC-1) AM7-AAA, (A-B, H441; and C-D, EBC-1) DTX and combinations of DTX with (A, H441; and C, EBC-1) AM2B-AAA or (B, H441; and D, EBC-1) AM7-AAA. Although AM7 is a higher affinity antibody than AM2B, AM2B-AAA achieved similar efficacy to AM7-AAA in preclinical efficacy models.

BRIEF DESCRIPTION OF THE SEQUENCE LISTING

Incorporated herein by reference in its entirety is a Sequence Listing entitled, "ABV12608USO1 Sequence Listing_ST25.txt", comprising SEQ ID NO: 1 through SEQ ID NO: 30, which includes the amino acid sequence disclosed herein. The Sequence Listing has been submitted herewith in ASCII text format via EFS. The Sequence Listing was first created on Jan. 13, 2022 and is 71,052 bytes in size.

DETAILED DESCRIPTION

Various aspects of the present disclosure relate to new anti-EGFR antibody-drug conjugates (ADCs, also called immunoconjugates), and pharmaceutical compositions thereof. In particular, the present disclosure describes new anti-EGFR ADCs comprising Bcl-xL inhibitors, synthons useful for synthesizing the ADCs, compositions comprising the ADCs, methods of making the ADCs, and various methods of using the ADCs.

As will be appreciated by skilled artisans, the various Bcl-xL inhibitors, ADCs and/or ADC synthons described herein may be in the form of salts, and in certain embodiments, particularly pharmaceutically acceptable salts. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion.

In the disclosure herein, if both structural diagrams and nomenclature are included and if the nomenclature conflicts with the structural diagram, the structural diagram controls.

Definitions

In order that the invention may be more readily understood, certain terms are first defined. In addition, it should be noted that whenever a value or range of values of a parameter are recited, it is intended that values and ranges intermediate to the recited values are also intended to be part of this invention. Further, unless otherwise defined herein, scientific and technical terms used in connection with the present disclosure shall have the meanings that are commonly understood by those of ordinary skill in the art.

The term "anti-Epidermal Growth Factor Receptor (EGFR) antibody" as used herein, refers to an antibody that specifically binds to EGFR. An antibody "which binds" an antigen of interest, i.e., EGFR, is one capable of binding that antigen with sufficient affinity such that the antibody is useful in targeting a cell expressing the antigen. In embodiments, the antibody specifically binds to human EGFR (hEGFR). Examples of anti-EGFR antibodies are disclosed below. Unless otherwise indicated, the term "anti-EGFR antibody" is meant to refer to an antibody which binds to wild type EGFR or any variant of EGFR, such as EGFRvIII.

The amino acid sequence of wild type human EGFR is provided below as SEQ ID NO: 15, including the signal peptide (amino acid residues 1-24), and the amino acid residues of the extracellular domain (ECD, amino acid residues 25-645). A truncated wild type ECD of the EGFR (also referred to herein as EGFR (1-525)) corresponds to SEQ ID NO: 16 and is equivalent to amino acids 1-525 of SEQ ID NO: 15. The mature form of wild type EGFR corresponds to the protein without the signal peptide, i.e., amino acid residues 25 to 1210 of SEQ ID NO: 15.

The amino acid sequence of the ECD of human EGFR is provided below as SEQ ID NO: 17 and includes the signal sequence.

EGFRvIII is the most commonly occurring variant of the EGFR in human cancers (Kuan et al. Endocr Relat Cancer. 8(2):83-96 (2001)). During the process of gene amplification, a 267 amino acid deletion occurs in the extracellular domain of EGFR with a glycine residue inserted at the fusion junction. Thus, EGFRvIII lacks amino acids 6-273 of the extracellular domain of wild type EGFR and includes a glycine residue insertion at the junction. The EGFRvIII variant of EGFR contains a deletion of 267 amino acid residues in the extracellular domain where a glycine is inserted at the deletion junction. The EGFRvIII amino acid sequence is shown below as SEQ ID NO: 18.

The terms "specific binding" or "specifically binding", as used herein, in reference to the interaction of an antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

The term "antibody" refers to an immunoglobulin molecule that specifically binds to an antigen and comprises two heavy (H) chains and two light (L) chains Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

In certain embodiments, an antibody can comprise a heavy chain having 1-5 amino acid deletions at the carboxy end of the heavy chain.

An "isolated antibody", as used herein, is intended to refer to an antibody that is substantially free of other antibodies having different antigenic specificities (e.g., an isolated antibody that specifically binds EGFR is substantially free of antibodies that specifically bind antigens other than EGFR). An isolated antibody that specifically binds EGFR may, however, have cross-reactivity to other antigens, such as EGFR molecules from other species. Moreover, an isolated antibody may be substantially free of other cellular material and/or chemicals.

The term "epitope" refers to a region of an antigen that is bound by an antibody or ADC. In embodiments, epitope determinants include chemically active surface groupings of molecules such as amino acids, sugar side chains, phosphoryl, or sulfonyl, and, in embodiments, may have specific three dimensional structural characteristics, and/or specific charge characteristics. In embodiments, an antibody is said to specifically bind an antigen when it preferentially recognizes its target antigen in a complex mixture of proteins and/or macromolecules. In embodiments, the antibodies of the invention bind to an epitope defined by the amino acid sequence CGADSYEMEEDGVRKC (SEQ ID NO: 20) (which corresponds to amino acid residues 287-302 of the mature form of hEGFR).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_a$", as used herein, is intended to refer to the on rate constant for association of an antibody to the antigen to form the antibody/antigen complex.

The term "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction (e.g., AM2 antibody and EGFR). $K_D$ is calculated by $k_d/k_a$.

The term "antibody-drug-conjugate" or "ADC" refers to a binding protein, such as an antibody or antigen binding fragment thereof, chemically linked to one or more chemical drug(s) (also referred to herein as agent(s), warhead(s), or payload(s)) that may optionally be therapeutic or cytotoxic agents. In embodiments, an ADC includes an antibody, a cytotoxic or therapeutic drug, and a linker that enables attachment or conjugation of the drug to the antibody. Here, the ADC comprises an anti-EGFR antibody conjugated via a linker to a Bcl-xL inhibitor.

The terms "anti-Epidermal Growth Factor antibody drug conjugate," "anti-EGFR antibody drug conjugate," or "anti-EGFR ADC", used interchangeably herein, refer to an ADC comprising an antibody that specifically binds to EGFR, whereby the antibody is conjugated to one or more chemical agent(s). Here, an anti-EGFR ADC comprises antibody AM2 conjugated to a Bcl-xL inhibitor.

Anti-EGFR Antibodies and Antibody Drug Conjugates

The anti-EGFR antibodies described herein provide the ADCs of the present disclosure with the ability to bind to EGFR such that the cytotoxic Bcl-xL drug attached to the antibody may be delivered to the EGFR-expressing cell.

In embodiments, the present disclosure provides an anti-EGFR IgG1 antibody. In embodiments, the humanized IgG1 anti-EGFR antibody is AM2. The AM2 antibody comprises a heavy chain variable region comprising a CDR1 domain comprising the amino acid sequence set forth as SEQ ID NO: 2, a CDR2 domain comprising the amino acid sequence set forth as SEQ ID NO: 3, and a CDR3 domain comprising the amino acid sequence set forth as SEQ ID NO: 4, and a light chain variable region comprising a CDR1 domain comprising the amino acid sequence set forth as SEQ ID NO: 6, a CDR2 domain comprising the amino acid sequence set forth as SEQ ID NO: 7, and a CDR3 domain comprising the amino acid sequence set forth as SEQ ID NO: 8. The AM2 antibody comprises a heavy chain variable region comprising the amino acid sequence set forth as SEQ ID NO: 22 and a light chain variable region comprising the amino acid sequence set forth as SEQ ID NO: 23. The AM2 antibody comprises a heavy chain comprising the amino acid sequence set forth as SEQ ID NO: 1 and a light chain comprising the amino acid sequence set forth as SEQ ID NO: 5.

The AM2 antibody binds a truncated form of the EGFR extracellular domain (ECD) that mimics the conformation of active EGFR with a higher affinity than depatuxizumab (used as the antibody component of depatuxizumab mafodotin, ABT-414). Despite this significantly increased affinity for the active form of EGFR, AM2 lacks any measurable binding to the full-length wild-type EGFR ECD. The AM2 antibody maintains the binding characteristics of the AM1 antibody (losatuxizumab, used as the antibody component of losatuxizumab vedotin, ABBV-221), but has a distinct sequence in order to mitigate potential safety issues, such as the infusion reactions observed with ABBV-221. The AM2 antibody is in the z,a allotype, as opposed to the z, non-a allotype for losatuxizumab. The AM2 antibody incorporates a LALA mutation, which reduces interaction with Fcγ receptors. AM2 also incorporates a C6v1 (LC:C214A) mutation, enabling site-specific conjugation and controlled DAR. Taken together, AM2's novel sequence mitigates potential safety issues, including those seen with previous anti-EGFR ADCs.

Antibodies may be produced by any of a number of techniques. For example, expression from host cells, wherein expression vector(s) encoding the heavy and light chains is (are) transfected into a host cell by standard techniques.

In embodiments, this disclosure provides an anti-hEGFR ADC comprising an anti-hEGFR antibody conjugated to a synthon, wherein the synthon is 6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-(2-{(3S,5S)-3-(2,5-dioxo-2,5-dihydro-1H-pyrrol-1-yl)-2-oxo-5-[(2-sulfoethoxy)methyl]pyrrolidin-1-yl}acetamido)-3-methylbutanoyl]amino}propanoyl]amino}phenyl)methoxy]carbonyl}[(3S)-3,4-dihydroxybutyl]amino)ethoxy]-5,7-dimethyladamantan-1-yl}methyl)-5-methyl-1H-pyrazol-4-yl]pyridine-2-carboxylic acid ("AAA"):

amino acid sequence set forth as SEQ ID NO: 3, and a heavy chain CDR3 domain comprising the amino acid sequence set forth as SEQ ID NO: 4; and a light chain variable region comprising a light chain CDR1 domain comprising the amino acid sequence set forth as SEQ ID NO: 6, a light chain CDR2 domain comprising the amino acid sequence set forth as SEQ ID NO: 7, and a light chain CDR3 domain comprising the amino acid sequence set forth as SEQ ID NO: 8. In embodiments, the antibody Ab comprises a heavy chain variable region comprising the amino acid sequence set forth as SEQ ID NO: 22 and a light chain variable region comprising the amino acid sequence set forth as SEQ ID NO: 23. In embodiments, the antibody Ab comprises a heavy chain comprising the amino acid sequence set forth as SEQ ID NO: 1 and a light chain comprising the amino acid sequence set forth as SEQ ID NO: 5. In embodiments, m is an integer between 1 and 3. In embodiments, m is 2. In embodiments, the antibody is conjugated to the structure of

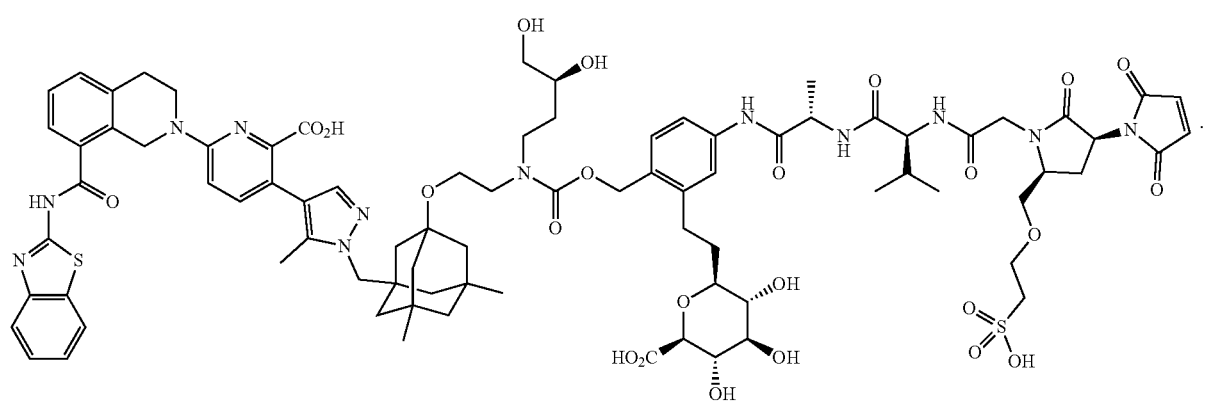 [SMILES: Cc1c(-c2ccc(N3CCc4cccc(C(=O)Nc5nc6ccccc6s5)c4C3)nc2C(=O)O)cnn1CC12CC3(C)CC(C)(C1)CC(OCCN(CC[C@H](O)CO)C(=O)OCc1ccc(NC(=O)[C@H](C)NC(=O)[C@@H](NC(=O)CN4C(=O)[C@@H](N5C(=O)C=CC5=O)C[C@H]4COCCS(=O)(=O)O)C(C)C)cc1CC[C@@H]1O[C@H](C(=O)O)[C@@H](O)[C@H](O)[C@H]1O)(C3)C2]

(IV)

In embodiments, the present disclosure provides an anti-human epidermal growth factor receptor (EGFR) antibody-drug conjugate comprising the following structure:

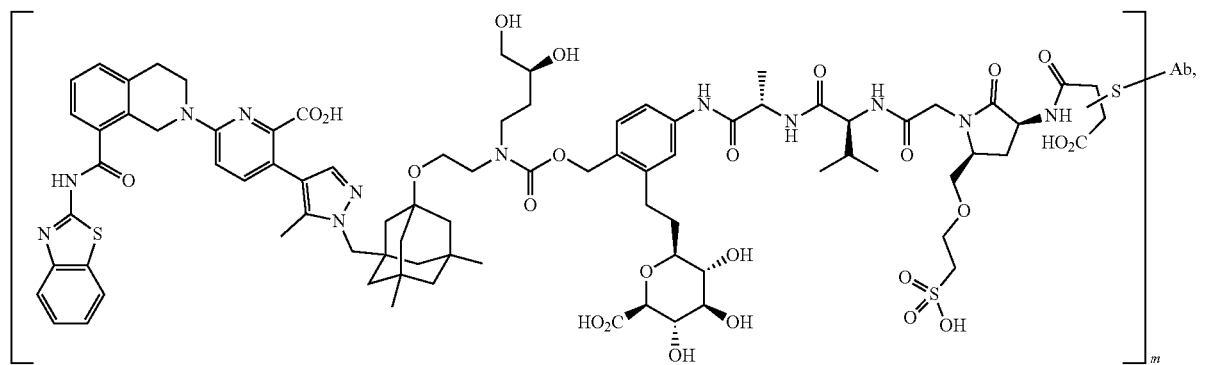

(I)

wherein m is an integer and Ab is an IgG1 anti-hEGFR antibody. In embodiments, the antibody comprises a heavy chain variable region comprising a heavy chain CDR1 domain comprising the amino acid sequence set forth as SEQ ID NO: 2, a heavy chain CDR2 domain comprising the formula (I) through C220 of the heavy chain (i.e., C219 of SEQ ID NO: 1).

In embodiments, the present disclosure provides an anti-human epidermal growth factor receptor (EGFR) antibody-drug conjugate comprising the following structure:

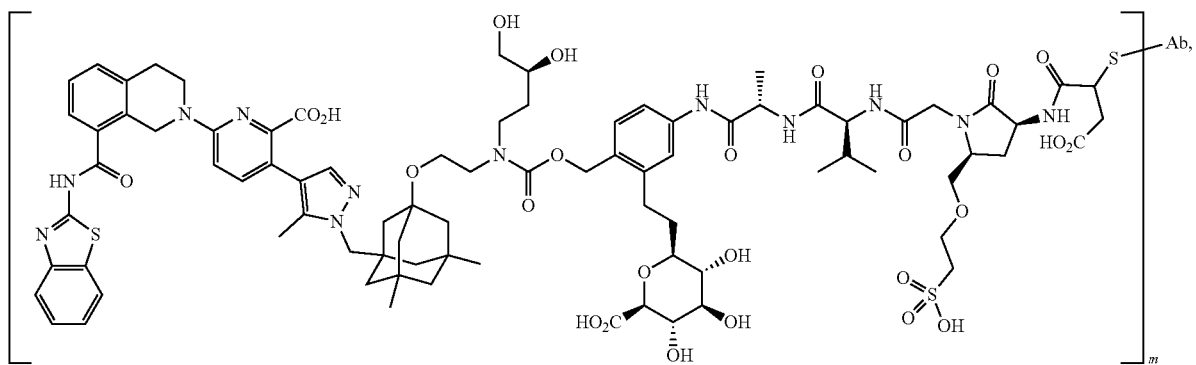

(II)

wherein m is an integer and Ab is an IgG1 anti-hEGFR antibody. In embodiments, the antibody comprises a heavy chain variable region comprising a heavy chain CDR1 domain comprising the amino acid sequence set forth as SEQ ID NO: 2, a heavy chain CDR2 domain comprising the amino acid sequence set forth as SEQ ID NO: 3, and a heavy chain CDR3 domain comprising the amino acid sequence set forth as SEQ ID NO: 4; and a light chain variable region comprising a light chain CDR1 domain comprising the amino acid sequence set forth as SEQ ID NO: 6, a light chain CDR2 domain comprising the amino acid sequence set forth as SEQ ID NO: 7, and a light chain CDR3 domain comprising the amino acid sequence set forth as SEQ ID NO: 8. In embodiments, the antibody Ab comprises a heavy chain variable region comprising the amino acid sequence set forth as SEQ ID NO: 22 and a light chain variable region comprising the amino acid sequence set forth as SEQ ID NO: 23. In embodiments, the antibody Ab comprises a heavy chain comprising the amino acid sequence set forth as SEQ ID NO: 1 and a light chain comprising the amino acid sequence set forth as SEQ ID NO: 5. In embodiments, m is an integer between 1 and 3. In embodiments, m is 2. In embodiments, the antibody is conjugated to the structure of formula (II) through C220 of the heavy chain (i.e., C219 of SEQ ID NO: 1).

In embodiments, the present disclosure provides an anti-human epidermal growth factor receptor (EGFR) antibody-drug conjugate comprising the following structure:

wherein m is an integer and Ab is an IgG1 anti-hEGFR antibody. In embodiments, the antibody comprises a heavy chain variable region comprising a heavy chain CDR1 domain comprising the amino acid sequence set forth as SEQ ID NO: 2, a heavy chain CDR2 domain comprising the amino acid sequence set forth as SEQ ID NO: 3, and a heavy chain CDR3 domain comprising the amino acid sequence set forth as SEQ ID NO: 4; and a light chain variable region comprising a light chain CDR1 domain comprising the amino acid sequence set forth as SEQ ID NO: 6, a light chain CDR2 domain comprising the amino acid sequence set forth as SEQ ID NO: 7, and a light chain CDR3 domain comprising the amino acid sequence set forth as SEQ ID NO: 8. In embodiments, the antibody Ab comprises a heavy chain variable region comprising the amino acid sequence set forth as SEQ ID NO: 22 and a light chain variable region comprising the amino acid sequence set forth as SEQ ID NO: 23. In embodiments, the antibody Ab comprises a heavy chain comprising the amino acid sequence set forth as SEQ ID NO: 1 and a light chain comprising the amino acid sequence set forth as SEQ ID NO: 5. In embodiments, m is an integer between 1 and 3. In embodiments, m is 2. In embodiments, the antibody is conjugated to the structure of formula (III) through C220 of the heavy chain (i.e., C219 of SEQ ID NO: 1).

In embodiments, the antibodies and antibody-drug conjugates of the present disclosure, such as the AM2 antibody and AM2-AAA ADC, bind to EGFR (1-525) (SEQ ID NO:

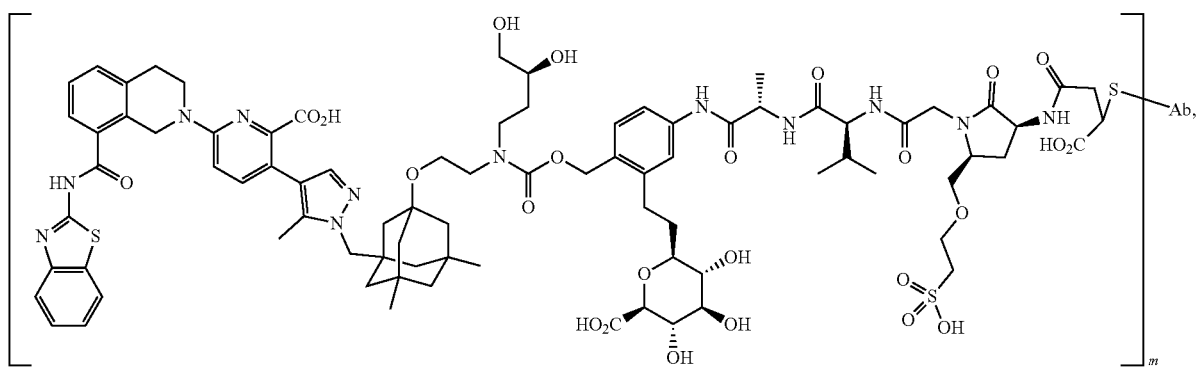

(III)

16) with a dissociation constant ($K_D$) of $1\times10^{-6}$ M or less, such as between $1\times10^{-6}$M and about $1\times10^{-6}$ M, or between about $1\times10^{-6}$M and about $1\times10^{-7}$M, as determined by surface plasmon resonance.

In embodiments, the antibodies of the present disclosure, such as the AM2 antibody and AM2-AAA ADC, bind to EGFRvIII (SEQ ID NO: 18) with a $K_D$ of about $6\times10-9$ M or less, or about $5.5\times10-9$ M or less, or $5.0\times10-9$ M or less, as determined by surface plasmon resonance.

METHODS OF USE

One embodiment pertains to a method of treating non-small cell lung cancer, comprising administering to a subject having non-small cell lung cancer an anti-EGFR ADC as described herein, in an amount effective to provide therapeutic benefit.

EXAMPLES

The following examples provide synthetic methods for Bcl-$X_L$ inhibitor (Example 1.1.17) and synthon (AAA, Example 1). Methods of synthesizing bcl-xL inhibitors and synthons such as AAA may be found, for example, in U.S. Patent Application Publication No. 2019/0343961 (AbbVie, Inc.), which is incorporated by reference herein in its entirety.

The examples were named using ACD/Name 2012 release (Build 56084, 5 Apr. 2012, Advanced Chemistry Development Inc., Toronto, Ontario), ACD/Name 2014 release (Build 66687, 25 Oct. 2013, Advanced Chemistry Development Inc., Toronto, Ontario), ACD/Name 2019.1.1 release (Build 110555, 18 Jul. 2019, Advanced Chemistry Development Inc., Toronto, Ontario), ChemDraw© Ver. 9.0.7 (CambridgeSoft, Cambridge, Mass.), ChemDraw® Ultra Ver. 12.0 (CambridgeSoft, Cambridge, Mass.), or ChemDraw® Professional Ver. 15.0.0.106. Bcl-$X_L$ inhibitor and synthon intermediates were named with ACD/Name 2012 release (Build 56084, 5 Apr. 2012, Advanced Chemistry Development Inc., Toronto, Ontario), ACD/Name 2014 release (Build 66687, 25 Oct. 2013, Advanced Chemistry Development Inc., Toronto, Ontario), ACD/Name 2019.1.1 release (Build 110555, 18 Jul. 2019, Advanced Chemistry Development Inc., Toronto, Ontario), ChemDraw® Ver. 9.0.7 (CambridgeSoft, Cambridge, Mass.), ChemDraw® Ultra Ver. 12.0 (CambridgeSoft, Cambridge, Mass.), or ChemDraw® Professional Ver. 15.0.0.106.

Abbreviations that may be used herein are:

| Abbreviation | Definition | Abbreviation | Definition |
| --- | --- | --- | --- |
| FACS | fluorescent activated cell sorting | HIC | hydrophobic interaction chromatography |
| HEPES | N-2-hydroxyethylpiperazine-N-ethanesulfonic acid buffer | HPLC | high performance liquid chromatography |
| DAR | drug to antibody ratio | MS | mass spectrometry |
| DMA | dimethyl acetamide | PBS | phosphate buffer saline |
| DMSO | dimethyl sulfoxide | NSCLC | non-small-cell lung carcinoma |
| FBS | fetal bovine serum | SEC | size exclusion chromatography |
| TCEP | (tris(2-carboxyethyl)phosphine) | q | quartet |
| mL | milliliter | min | minute |
| NMR | nuclear magnetic resonance | mL | milliliter |
| LC/MS or LCMS or LC-MS | liquid chromatography- mass spectrometry | μL | microliter |
| s | singlet | L | liter |
| br s | broad singlet | g | gram |
| d | duplet or doublet | mg | milligram |
| m | multiplet | mmol | millimoles |
| t | triplet | dd | doublet of doublets |
| td | triplet of doublets | br t | broad triplet |
| br d | broad doublet | mM | millimolar |
| br m | broad multiplet | ppm | parts per million |
| M | molarity (moles/liter) | DCI | desorption chemical ionization |
| N | normality (equivalent/liter) | w/w | weight for weight |
| APCI | atmospheric pressure chemical ionization | mm | millimeter |
| ESI | electrospray ionization | MHz | megahertz |
| m/z | mass divided by charge number | μm | micrometer |
| psi | pounds per square inch | BIM | Bcl-2-like protein 11 |
| v/v | volume for volume | DPBS | Dulbecco's phosphate-buffered saline |
| SCID | Severe combined immunodeficiency | | |
| TMP | transmembrane pressure | | |

Example 1: 6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-(2-{(3S,5S)-3-(2,5-dioxo-2,5-dihydro-1H-pyrrol-1-yl)-2-oxo-5-[(2-sulfoethoxy)methyl]pyrrolidin-1-yl}acetamido)-3-methylbutanoyl]amino}propanoyl]amino}phenyl)methoxy]carbonyl}[(3S)-3,4-dihydroxybutyl]amino)ethoxy]-5,7-dimethyladamantan-1-yl}methyl)-5-methyl-1H-pyrazol-4-yl]pyridine-2-carboxylic acid (Synthon AAA)

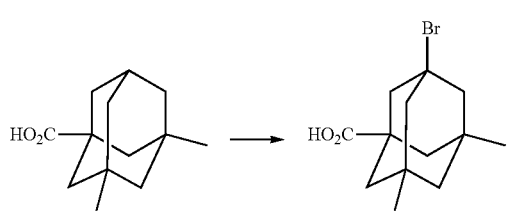 [SMILES: CC12CC3CC(C)(C1)CC(C(=O)O)(C3)C2 ; CC12CC3(C)CC(Br)(C1)CC(C(=O)O)(C2)C3]

Example 1.1.1:
3-bromo-5,7-dimethyladamantane-1-carboxylic acid

Into a 50 mL round-bottomed flask at 0° C., was added bromine (16 mL). Iron powder (7 g) was added, and the reaction mixture was stirred at 0° C. for 30 minutes. 3,5-Dimethyladamantane-1-carboxylic acid (12 g) was added. The mixture was warmed up to room temperature and stirred for 3 days. A mixture of ice and concentrated HCl was poured into the reaction mixture. The resulting suspension was treated twice with Na$_2$SO$_3$ (50 g in 200 mL water) and extracted three times with dichloromethane. The combined organic fractions were washed with 1 N aqueous HCl, dried over sodium sulfate, filtered, and concentrated to give the title compound.

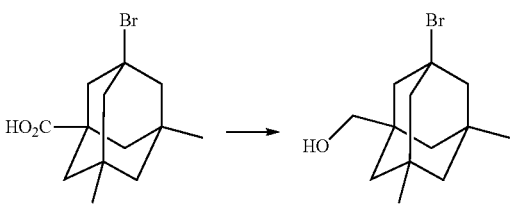 [SMILES: CC12CC3(C)CC(Br)(C1)CC(C(=O)O)(C2)C3 ; CC12CC3(C)CC(Br)(C1)CC(CO)(C2)C3]

Example 1.1.2:
(3-bromo-5,7-dimethyladamantan-1-yl)methanol

To a solution of Example 1.1.1 (15.4 g) in tetrahydrofuran (200 mL) was added BH$_3$ (1 M in tetrahydrofuran, 150 mL), and the mixture was stirred at room temperature overnight. The reaction mixture was then carefully quenched by adding methanol dropwise. The mixture was then concentrated under vacuum, and the residue was partitioned between ethyl acetate (500 mL) and 2 N aqueous HCl (100 mL). The aqueous layer was further extracted twice with ethyl acetate, and the combined organic extracts were washed with water and brine, dried over sodium sulfate, and filtered. The filtrate was concentrated to give the title compound.

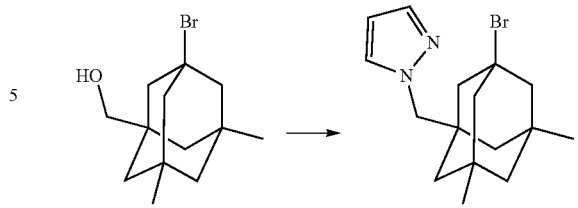

Example 1.1.3: 1-[(3-bromo-5,7-dimethyladamantan-1-yl)methyl]-1H-pyrazole

To a solution of Example 1.1.2 (8.0 g) in toluene (60 mL) was added 1H-pyrazole (1.55 g) and cyanomethylenetributylphosphorane (2.0 g), and the mixture was stirred at 90° C. overnight. The reaction mixture was concentrated, and the residue was purified by silica gel column chromatography (10:1 heptane:ethyl acetate) to give the title compound. MS (ESI) m/z 324.2 (M+H)$^+$.

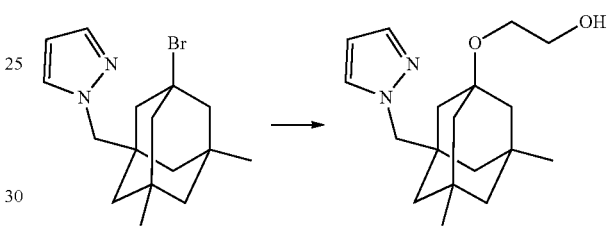

Example 1.1.4: 2-({3,5-dimethyl-7-[(1H-pyrazol-1-yl)methyl]adamantan-1-yl}oxy)ethan-1-ol To a solution of Example 1.1.3 (4.0 g) in ethane-1,2-diol (12 mL) was added triethylamine (3 mL). The mixture was stirred at 150° C. under microwave conditions (Biotage® Initiator) for 45 minutes. The mixture was poured into water (100 mL) and extracted three times with ethyl acetate. The combined organic extracts were washed with water and brine, dried over sodium sulfate, and filtered. Concentration of the filtrate gave a residue that was purified by silica gel chromatography, eluted with 20% ethyl acetate in heptane, followed by 5% methanol in dichloromethane, to give the title compound. MS (ESI) m/z 305.2 (M+H)$^+$.

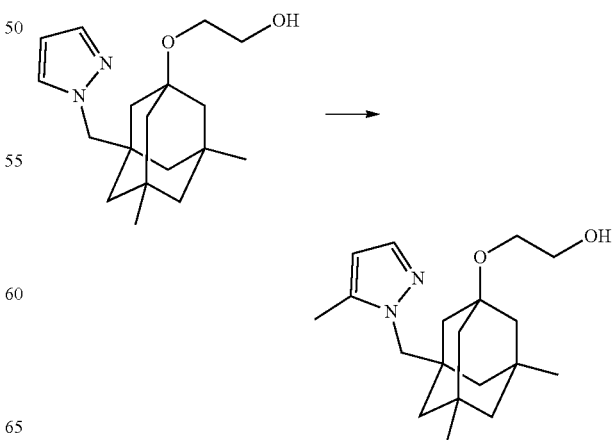

Example 1.1.5: 2-({3,5-dimethyl-7-[(5-methyl-1H-pyrazol-1-yl)methyl]adamantan-1-yl}oxy)ethan-1-ol To a cooled (-78° C.) solution of Example 1.1.4 (6.05 g) in tetrahydrofuran (100 mL) was added n-butyllithium (40 mL, 2.5 M in hexane), and the mixture was stirred at -78° C. for 1.5 hours. Iodomethane (10 mL) was added through a syringe, and the mixture was stirred at -78° C. for 3 hours. The reaction mixture was then quenched with aqueous NH₄Cl and extracted twice with ethyl acetate, and the combined organic extracts were washed with water and brine. After drying over sodium sulfate, the solution was filtered and concentrated, and the residue was purified by silica gel column chromatography, eluted with 5% methanol in dichloromethane, to give the title compound. MS (ESI) m/z 319.5 (M+H)⁺.

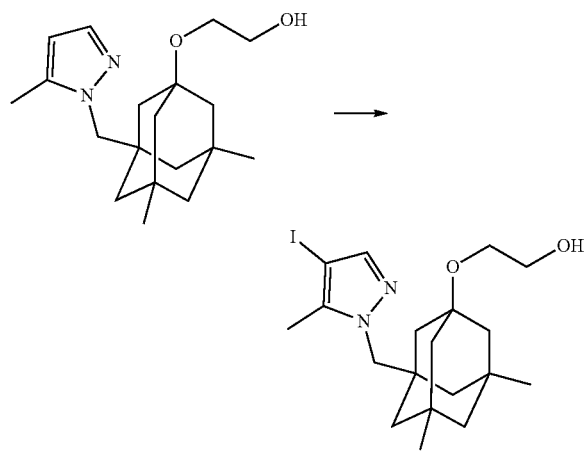

Example 1.1.6: 2-({3-[(4-iodo-5-methyl-1H-pyrazol-1-yl)methyl]-5,7-dimethyladamantan-1-yl}oxy)ethan-1-ol To a solution of Example 1.1.5 (3.5 g) in N,N-dimethylformamide (30 mL) was added N-iodosuccinimide (3.2 g), and the mixture was stirred at room temperature for 1.5 hours. The reaction mixture was diluted with ethyl acetate (600 mL) and washed with aqueous 10% w/w NaHSO₃, water and brine. The organic layer was dried over sodium sulfate, filtered, and concentrated under reduced pressure. The residue was purified by silica gel chromatography, eluted with 20% ethyl acetate in dichloromethane, to give the title compound. MS (ESI) m/z 445.3 (M+H)⁺.

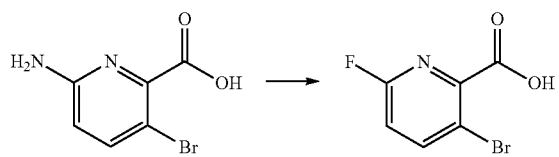 [SMILES: Nc1ccc(Br)c(C(=O)O)n1 ; O=C(O)c1nc(F)ccc1Br]

Example 1.1.7: 3-bromo-6-fluoropyridine-2-carboxylic acid

A slurry of 6-amino-3-bromopyridine-2-carboxylic acid (25 g) in 1:1 dichloromethane/chloroform (400 mL) was added to nitrosonium tetrafluoroborate (18.2 g) in dichloromethane (100 mL) at 5° C. over 1 hour. The resulting mixture was stirred for another 30 minutes, then warmed to 35° C. and stirred overnight. The reaction was cooled to room temperature, and then adjusted to pH 4 with aqueous NaH₂PO₄ solution. The resulting solution was extracted three times with dichloromethane, and the combined extracts were washed with brine, dried over sodium sulfate, filtered, and concentrated to provide the title compound.

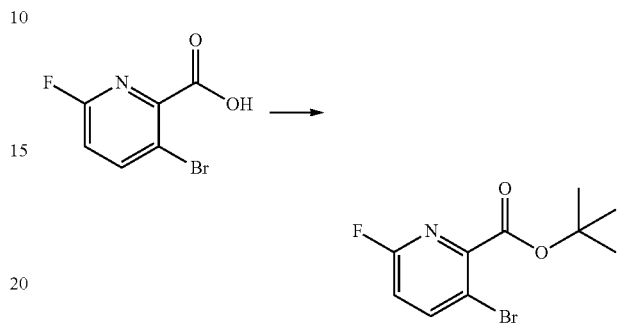

Example 1.1.8: tert-butyl 3-bromo-6-fluoropyridine-2-carboxylate para-Toluenesulfonyl chloride (27.6 g) was added to a solution of Example 1.1.7 (14.5 g) and pyridine (26.7 mL) in dichloromethane (100 mL) and tert-butanol (80 mL) at 0° C. The reaction was stirred for 15 minutes, and then warmed to room temperature, and stirred overnight. The solution was concentrated and partitioned between ethyl acetate and saturated aqueous Na₂CO₃ solution. The layers were separated, and the aqueous layer extracted with ethyl acetate. The organic layers were combined, rinsed with aqueous Na₂CO₃ solution and brine, dried over sodium sulfate, filtered, and concentrated to provide the title compound.

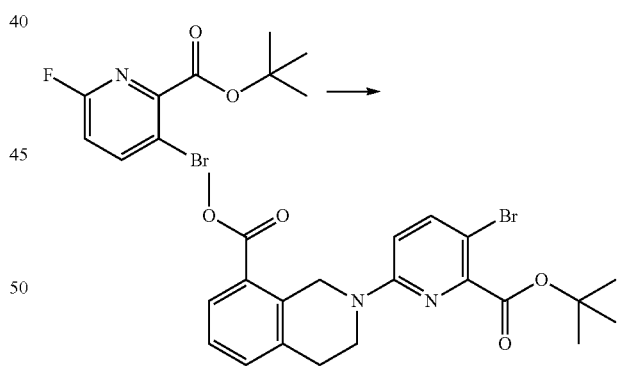

Example 1.1.9: methyl 2-[5-bromo-6-(tert-butoxycarbonyl)pyridin-2-yl]-1,2,3,4-tetrahydroisoquinoline-8-carboxylate To a solution of methyl 1,2,3,4-tetrahydroisoquinoline-8-carboxylate hydrochloride (12.37 g) and Example 1.1.8 (15 g) in dimethyl sulfoxide (100 mL) was added N,N-diisopropylethylamine (12 mL), and the mixture was stirred at 50° C. for 24 hours. The mixture was then diluted with ethyl acetate (500 mL) and washed with water and brine. The organic layer was dried over sodium sulfate, filtered, and concentrated under reduced pressure. The residue was purified by silica gel chromatography, eluted with 20% ethyl acetate in hexane, to give the title compound. MS (ESI) m/z 448.4 (M+H)⁺.

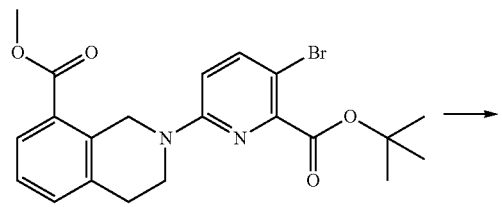

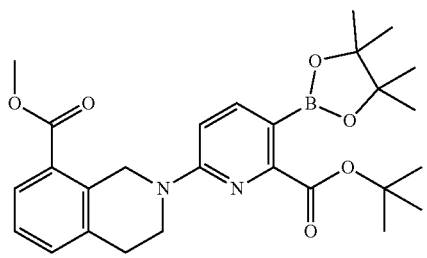

Example 1.1.10: methyl 2-[6-(tert-butoxycarbonyl)-5-(4,4,5,5-tetramethyl-1,3,2-dioxaborolan-2-yl)pyridin-2-yl]-1,2,3,4-tetrahydroisoquinoline-8-carboxylate To a solution of Example 1.1.9 (2.25 g) and [1,1'-bis(diphenylphosphino)ferrocene]dichloropalladium(II) (205 mg) in acetonitrile (30 mL) was added triethylamine (3 mL) and pinacolborane (2 mL), and the mixture was stirred at reflux for 3 hours. The mixture was diluted with ethyl acetate (200 mL) and washed with water and brine. The organic layer was dried over sodium sulfate, filtered, and concentrated under reduced pressure. Purification of the residue by silica gel chromatography, eluted with 20% ethyl acetate in hexane, provided the title compound.

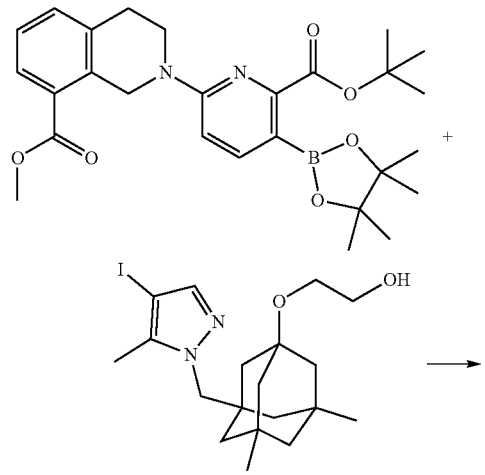

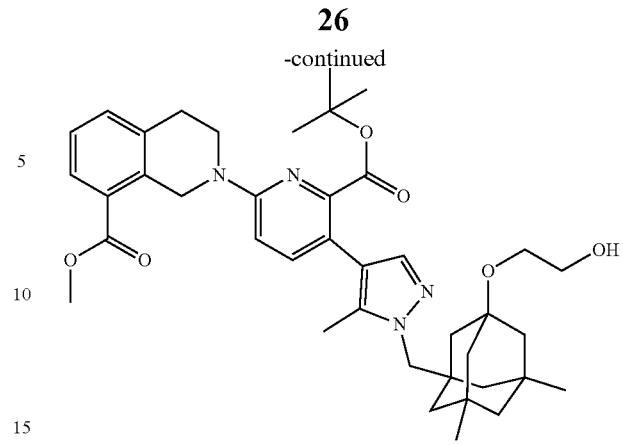

Example 1.1.11: methyl 2-[6-(tert-butoxycarbonyl)-5-(1-{[3-(2-hydroxyethoxy)-5,7-dimethyladamantan-1-yl]methyl}-5-methyl-1H-pyrazol-4-yl)pyridin-2-yl]-1,2,3,4-tetrahydroisoquinoline-8-carboxylate To a solution of Example 1.1.10 (2.25 g) in tetrahydrofuran (30 mL) and water (10 mL) was added Example 1.1.6 (2.0 g), 1,3,5,7-tetramethyl-6-phenyl-2,4,8-trioxa-6-phosphaadamantane (329 mg), tris(dibenzylideneacetone)dipalladium(0) (206 mg) and potassium phosphate tribasic (4.78 g). The mixture was refluxed overnight, cooled, and diluted with ethyl acetate (500 mL). The resulting mixture was washed with water and brine, and the organic layer was dried over sodium sulfate, filtered, and concentrated. The residue was purified by flash chromatography on silica gel, eluted with 20% ethyl acetate in heptanes followed by 5% methanol in dichloromethane, to provide the title compound.

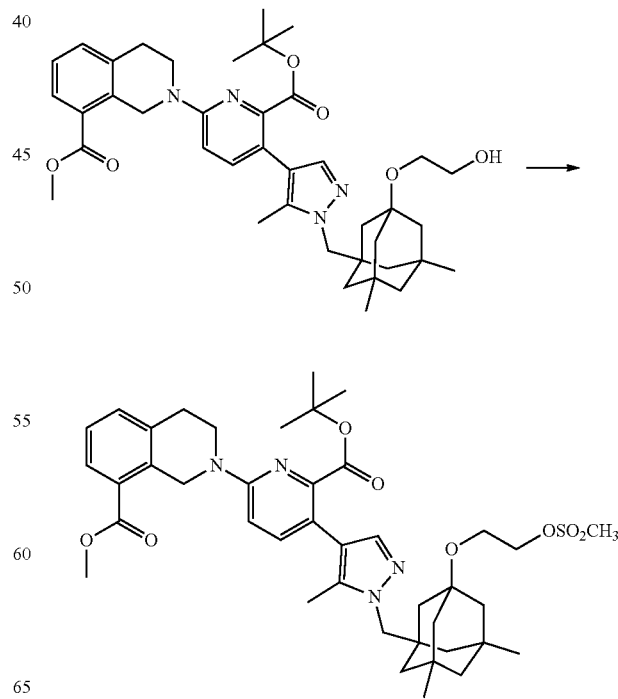

Example 1.1.12: methyl 2-[6-(tert-butoxycarbonyl)-5-{1-[(3-{2-[(methanesulfonyl)oxy]ethoxy}-5,7-dimethyladamantan-1-yl)methyl]-5-methyl-1H-pyrazol-4-yl}pyridin-2-yl]-1,2,3,4-tetrahydroisoquinoline-8-carboxylate To a cold solution of Example 1.1.11 (3.32 g) in dichloromethane (100 mL) in an ice-bath was sequentially added triethylamine (3 mL) and methanesulfonyl chloride (1.1 g). The reaction mixture was stirred at room temperature for 1.5 hours, diluted with ethyl acetate, and washed with water and brine. The organic layer was dried over sodium sulfate, filtered, and concentrated to provide the title compound.

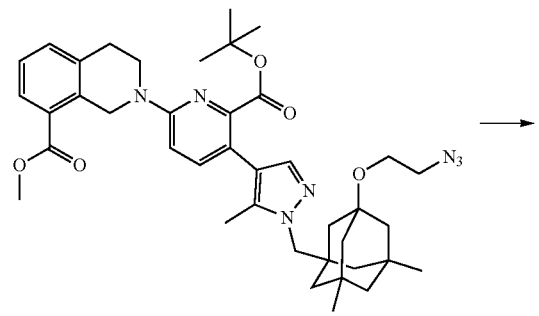

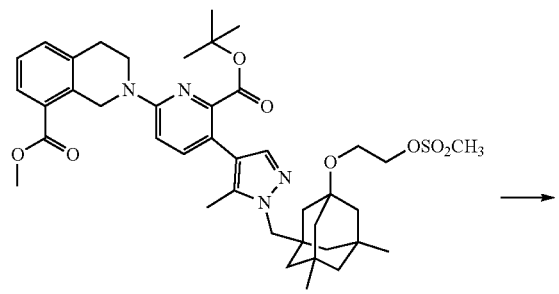

Example 1.1.13: methyl 2-[5-(1-{[3-(2-azidoethoxy)-5,7-dimethyladamantan-1-yl]methyl}-5-methyl-1H-pyrazol-4-yl)-6-(tert-butoxycarbonyl)pyridin-2-yl]-1,2,3,4-tetrahydroisoquinoline-8-carboxylate To a solution of Example 1.1.12 (16.5 g) in N,N-dimethylformamide (120 mL) was added sodium azide (4.22 g). The mixture was heated at 80° C. for 3 hours, cooled, diluted with ethyl acetate, and washed with water and brine. The organic layer was dried over sodium sulfate, filtered, and concentrated. The residue was purified by flash chromatography on silica gel, eluted with 20% ethyl acetate in heptanes, to provide the title compound.

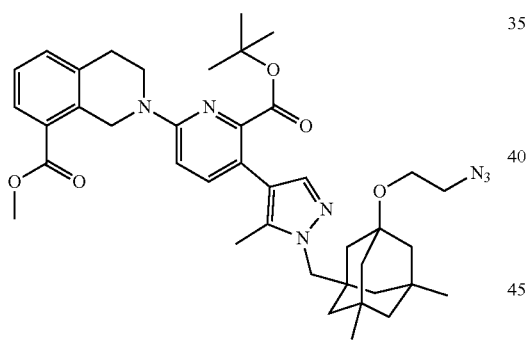

Example 1.1.14: 2-[5-(1-{[3-(2-azidoethoxy)-5,7-dimethyladamantan-1-yl]methyl}-5-methyl-1H-pyrazol-4-yl)-6-(tert-butoxycarbonyl)pyridin-2-yl]-1,2,3,4-tetrahydroisoquinoline-8-carboxylic acid To a solution of Example 1.1.13 (10 g) in a mixture of tetrahydrofuran (60 mL), methanol (30 mL) and water (30 mL) was added lithium hydroxide monohydrate (1.2 g). The mixture was stirred at room temperature overnight and neutralized with 2% aqueous HCl. The resulting mixture was concentrated, and the residue was dissolved in ethyl acetate (800 mL) and washed with brine. The organic layer was dried over sodium sulfate, filtered, and concentrated to provide the title compound.

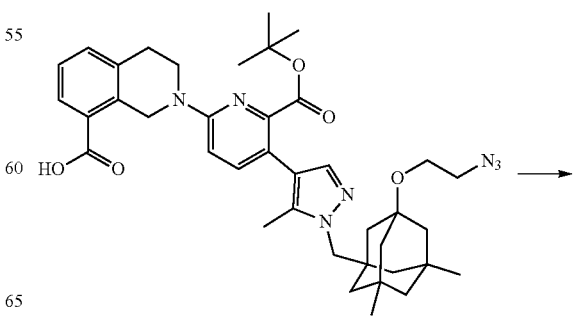

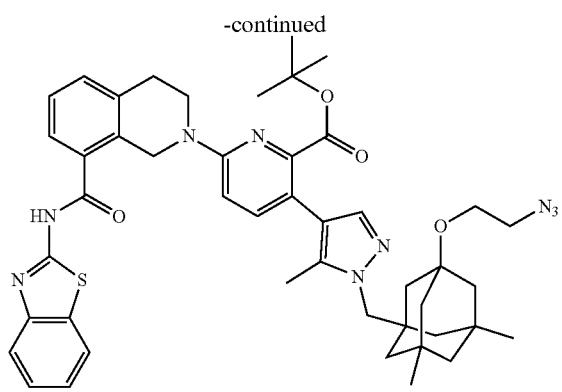

Example 1.1.15: tert-butyl 3-(1-{[3-(2-azidoethoxy)-5,7-dimethyladamantan-1-yl]methyl}-5-methyl-1H-pyrazol-4-yl)-6-{8-[(1,3-benzothiazol-2-yl)carbamoyl]-3,4-dihydroisoquinolin-2(1H)-yl}pyridine-2-carboxylate A mixture of Example 1.1.14 (10 g), benzo[d]thiazol-2-amine (3.24 g), fluoro-N,N,N',N'-tetramethylformamidinium hexafluorophosphate (5.69 g) and N,N-diisopropylethylamine (5.57 g) in N,N-dimethylformamide (20 mL) was heated at 60° C. for 3 hours, cooled and diluted with ethyl acetate. The resulting mixture was washed with water and brine. The organic layer was dried over sodium sulfate, filtered, and concentrated. The residue was purified by flash chromatography on silica gel, eluted with 20% ethyl acetate in dichloromethane to give the title compound.

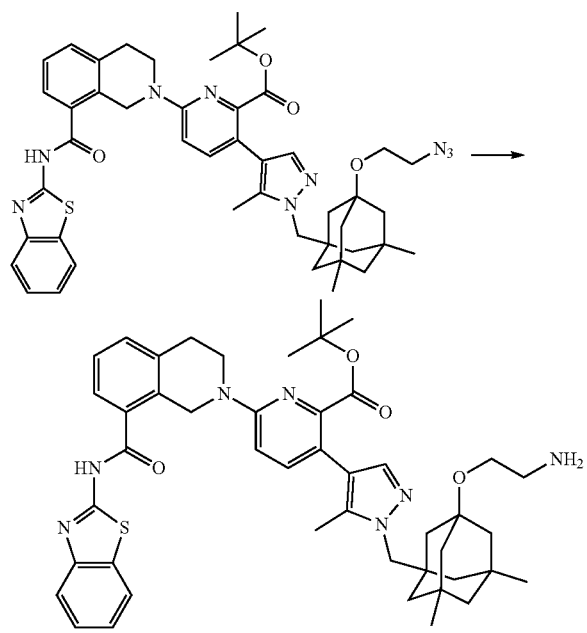

Example 1.1.16: tert-butyl 3-(1-{[3-(2-aminoethoxy)-5,7-dimethyladamantan-1-yl]methyl}-5-methyl-1H-pyrazol-4-yl)-6-{8-[(1,3-benzothiazol-2-yl)carbamoyl]-3,4-dihydroisoquinolin-2(1H)-yl}pyridine-2-carboxylate To a solution of Example 1.1.15 (2.0 g) in tetrahydrofuran (30 mL) was added Pd/C (10%, 200 mg). The mixture was stirred under a hydrogen atmosphere (18 psi) overnight. The insoluble material was filtered off and the filtrate was concentrated to provide the title compound.

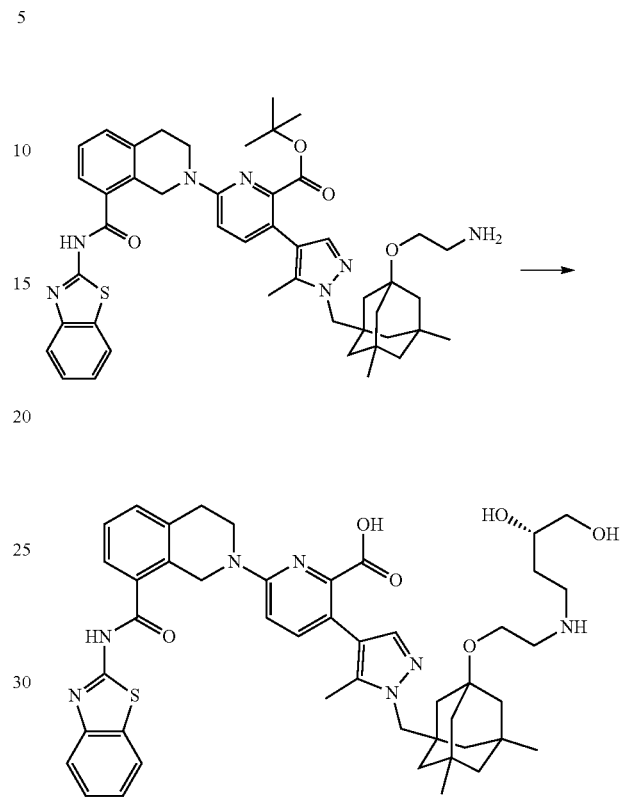

Example 1.1.17: 6-{8-[(1,3-benzothiazol-2-yl)carbamoyl]-3,4-dihydroisoquinolin-2(1H)-yl}-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid To a solution of Example 1.1.16 (213 mg) in dichloromethane (2 mL) was added (S)-2-(2,2-dimethyl-1,3-dioxolan-4-yl)acetaldehyde (42 mg). After stirring at room temperature for 30 minutes, sodium triacetoxyborohydride (144 mg) was added. The reaction mixture was stirred at room temperature overnight. Trifluoroacetic acid (2 mL) was added and stirring was continued overnight. The reaction mixture was concentrated, and the residue was purified by reverse-phase HPLC using a Gilson system (Phenomenex® Luna® C18 250×50 mm column), eluted with 5-85% acetonitrile in water containing 0.1% v/v trifluoroacetic acid (100 mL/minute). The desired fractions were combined and freeze-dried to provide the title compound. $^1$H NMR (400 MHz, dimethyl sulfoxide-$d_6$) δ ppm 12.86 (s, 1H), 8.22 (d, 2H), 8.05-8.01 (m, 1H), 7.79 (d, 1H), 7.61 (d, 1H), 7.53-7.41 (m, 3H), 7.36 (td, 2H), 7.28 (s, 1H), 6.95 (d, 1H), 4.95 (s, 2H), 3.88 (t, 2H), 3.82 (s, 2H), 3.26-2.94 (m, 7H), 2.10 (s, 3H), 1.84-1.75 (m, 1H), 1.52-1.63 (m, 1H), 1.45-1.23 (m, 6H), 1.19-0.96 (m, 7H), 0.86 (s, 6H); MS (ESI) m/z 834.3 (M+H)$^+$.

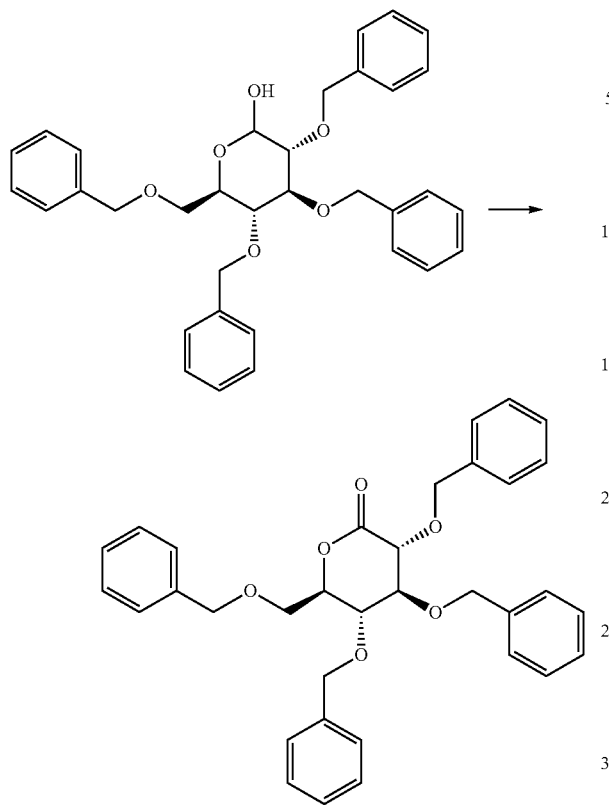

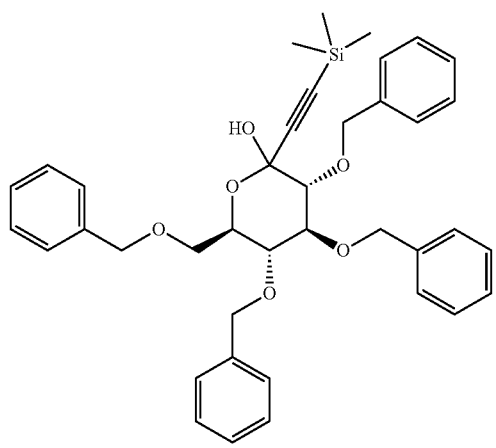

Example 1.2.1: (3R,4S,5R,6R)-3,4,5-tris(benzyloxy)-6-[(benzyloxy)methyl]oxan-2-one To a mixture of (3R,4S,5R,6R)-3,4,5-tris(benzyloxy)-6-[(benzyloxy)methyl]oxan-2-ol (75 g) in dimethyl sulfoxide (400 mL) at 0° C. was added acetic anhydride (225 mL). The mixture was stirred for 16 hours at room temperature before it was cooled to 0° C. A large volume of water was added and stirring was stopped allowing the reaction mixture to settle for 3 hours (the crude lactone migrated to the bottom of the flask). The supernatant was removed, and the crude mixture was diluted with ethyl acetate and was washed 3 times with water, neutralized with a saturated aqueous mixture of $NaHCO_3$, and washed again twice with water. The organic layer was then dried over magnesium sulfate, filtered, and concentrated to give the title compound. MS (ESI) m/z 561 $(M+Na)^+$.

Example 1.2.2: (3R,4S,5R,6R)-3,4,5-tris(benzyloxy)-6-((benzyloxy)methyl)-2-((trimethylsilyl)ethynyl)tetrahydro-2H-pyran-2-ol To a mixture of ethynyltrimethylsilane (18.23 g) in tetrahydrofuran (400 mL) under nitrogen and chilled in a dry ice/acetone bath (internal temp −65° C.) was added 2.5 M butyllithium in hexane (55.7 mL) dropwise, keeping the temperature below −60° C. The mixture was stirred in a cold bath for 40 minutes, followed by an ice-water bath (internal temperature rose to 0.4° C.) for 40 minutes, and finally cooled to −75° C. again. A mixture of Example 1.2.1 (50 g) in tetrahydrofuran (50 mL) was added dropwise, keeping the internal temperature below −70° C. The mixture was stirred in a dry ice/acetone bath for an additional 3 hours. The reaction was quenched with saturated aqueous $NaHCO_3$ (250 mL). The mixture was allowed to warm to room temperature, extracted with ethyl acetate (3×300 mL), dried over $MgSO_4$, filtered, and concentrated in vacuo to give the title compound. MS (ESI) m/z 659 $(M+Na)^+$.

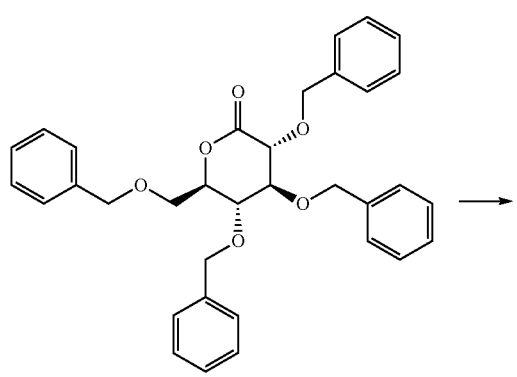

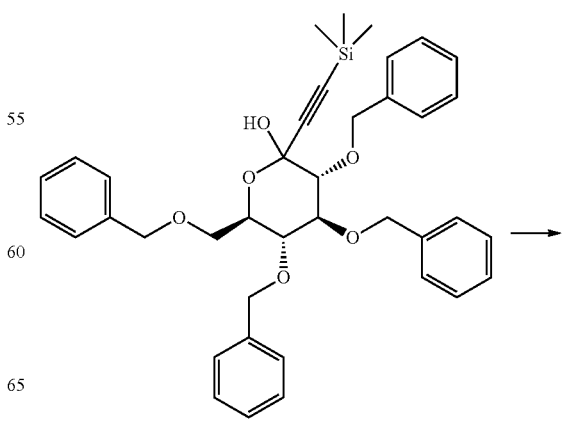

-continued

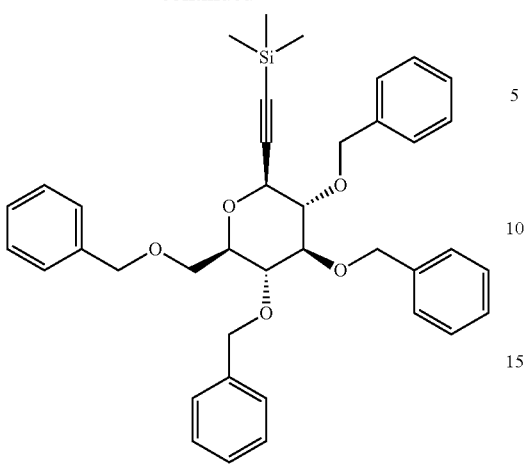

Example 1.2.3: trimethyl({(2S,3S,4R,5R,6R)-3,4,5-tris(benzyloxy)-6-[(benzyloxy)methyl]oxan-2-yl}ethynyl)silane To a mixed mixture of Example 1.2.2 (60 g) in acetonitrile (450 mL) and dichloromethane (150 mL) at −15° C. in an ice-salt bath was added triethylsilane (81 mL) dropwise, followed by addition of boron trifluoride diethyl ether complex (40.6 mL) at such a rate that the internal temperature did not exceed −10° C. The mixture was then stirred at −15° C. to −10° C. for 2 hours. The reaction was quenched with saturated aqueous NaHCO$_3$ (275 mL) and stirred for 1 hour at room temperature. The mixture was then extracted with ethyl acetate (3×550 mL). The combined extracts were dried over MgSO$_4$, filtered, and concentrated. The residue was purified by flash chromatography eluted with a gradient of 0% to 7% ethyl acetate/petroleum ether to give the title compound. MS (ESI) m/z 643 (M+Na)$^+$.

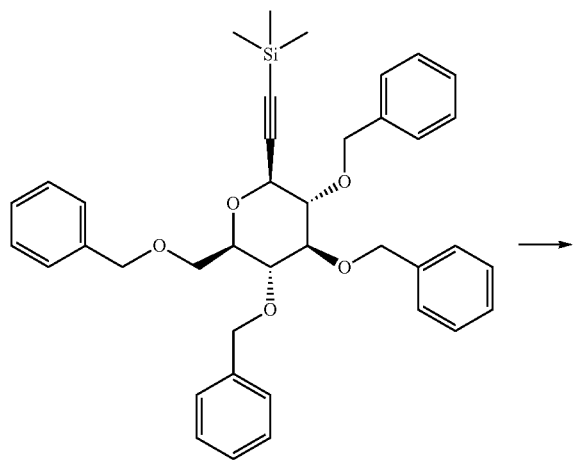

-continued

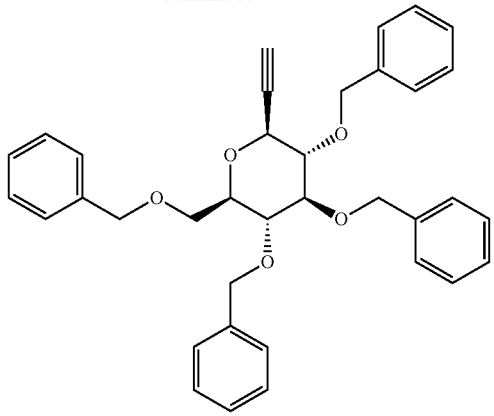

Example 1.2.4: (2R,3R,4R,5S,6S)-3,4,5-tris(benzyloxy)-2-[(benzyloxy)methyl]-6-ethynyloxane To a mixture of Example 1.2.3 (80 g) in dichloromethane (200 mL) and methanol (1000 mL) was added 1 N aqueous NaOH (258 mL). The mixture was stirred at room temperature for 2 hours and then concentrated. The residue was then partitioned between water and dichloromethane. The combined organic extracts were washed with brine, dried over Na$_2$SO$_4$, filtered, and concentrated to give the title compound. MS (ESI) m/z 571 (M+Na)$^+$.

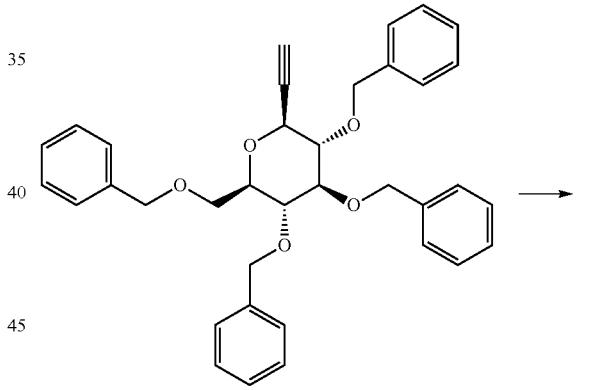

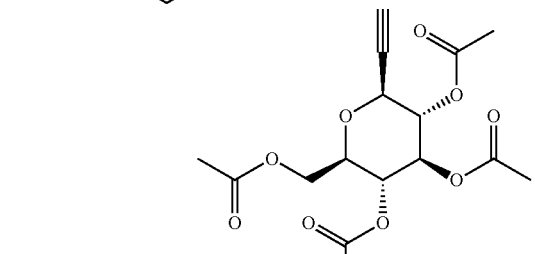

Example 1.2.5: (2R,3R,4R,5S,6S)-2-[(acetyloxy)methyl]-6-ethynyloxane-3,4,5-triyl triacetate To a mixture of Example 1.2.4 (66 g) in acetic anhydride (500 mL) cooled by an ice/water bath was added boron trifluoride diethyl ether complex (152 mL) dropwise. The mixture was stirred at room temperature for 16 hours, cooled with an ice/water bath and neutralized with saturated aqueous NaHCO$_3$. The mixture was extracted with ethyl acetate (3×500 mL), dried over Na$_2$SO$_4$, filtered, and concentrated in vacuo. The residue was purified by flash chromatography eluted with a gradient of 0% to 30% ethyl acetate/petroleum ether to give the title compound. MS (ESI) m/z 357 (M+H)$^+$.

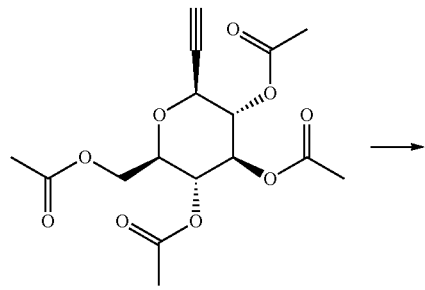

Example 1.2.6: (2S,3R,4R,5S,6R)-2-ethynyl-6-(hydroxymethyl)oxane-3,4,5-triol To a mixture of Example 1.2.5 (25 g) in methanol (440 mL) was added sodium methanolate (2.1 g). The mixture was stirred at room temperature for 2 hours, and then neutralized with 4 M HCl in dioxane. The mixture was concentrated, and the residue was adsorbed onto silica gel and loaded onto a silica gel column. The column was eluted with a gradient of 0 to 100% ethyl acetate/petroleum ether then 0% to 12% methanol/ethyl acetate to give the title compound. MS (ESI) m/z 211 (M+Na)$^+$.

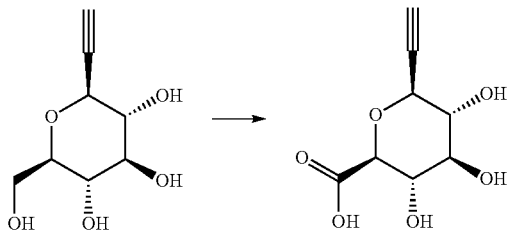

Example 1.2.7: (2S,3S,4R,5R,6S)-6-ethynyl-3,4,5-trihydroxyoxane-2-carboxylic acid A three-necked round bottom flask was charged with Example 1.2.6 (6.00 g), KBr (0.30 g), tetrabutylammonium bromide (0.41 g) and 60 mL of saturated aqueous NaHCO$_3$. TEMPO ((2,2,6,6-tetramnethylpiperidin-1-yl)oxyl, 0.15 g) in dichloromethane (60 mL) was added. The mixture was stirred vigorously and cooled in an ice-salt bath to −2° C. internal temperature. A mixture of brine (12 mL), saturated aqueous NaHCO$_3$ (24 mL) and 10 weight % aqueous NaOCl (154 mL) solution was added dropwise such that the internal temperature was maintained below 2° C. The pH of the reaction mixture was maintained in the 8.2-8.4 range with the addition of solid Na$_2$CO$_3$. After a total of 6 hours, the reaction mixture was cooled to 3° C. internal temperature and ethanol (~20 mL) was added dropwise. The mixture was stirred for ~30 minutes. The mixture was transferred to a separatory funnel, and the dichloromethane layer was discarded. The pH of the aqueous layer was adjusted to 2-3 using 1 M aqueous HCl. The aqueous layer was then concentrated to dryness to afford a solid. Methanol (100 mL was) added to the dry solid, and the slurry was stirred for ~30 minutes. The mixture was filtered over a pad of diatomaceous earth, and the residue in the funnel was washed with ~100 mL of methanol. The filtrate was concentrated under reduced pressure to obtain the title compound.

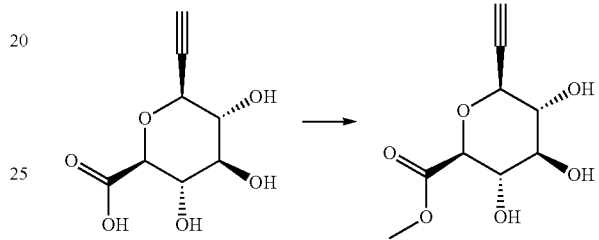

Example 1.2.8: methyl (2S,3S,4R,5R,6S)-6-ethynyl-3,4,5-trihydroxyoxane-2-carboxylate A 500 mL three-necked round bottom flask was charged with a suspension of Example 1.2.7 (6.45 g) in methanol (96 mL), and the mixture was cooled in an ice-salt-bath with internal temperature of −1° C. Neat thionyl chloride (2.79 mL) was carefully added. The internal temperature kept rising throughout the addition but did not exceed 10° C. The reaction was allowed to slowly warm up to 15-20° C. over 2.5 hours. After 2.5 hours, the reaction was concentrated to give the title compound.

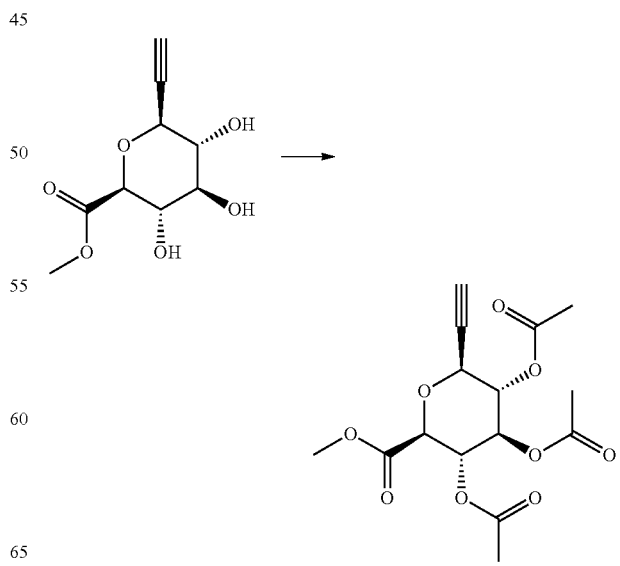

Example 1.2.9: methyl (2S,3S,4R,5S,6S)-3,4,5-tris(acetyloxy)-6-ethynyloxane-2-carboxylate To Example 1.2.8 (6.9 g) as a mixture in N,N-dimethylformamide (75 mL) was added 4-(dimethylamino)pyridine (0.17 g) and acetic anhydride (36.1 mL). The suspension was cooled in an ice-bath and pyridine (18.04 mL) was added via syringe over 15 minutes. The reaction was allowed to warm to room temperature overnight. Additional acetic anhydride (12 mL) and pyridine (6 mL) were added and stirring was continued for an additional 6 hours. The reaction was cooled in an ice-bath and 250 mL of saturated aqueous $NaHCO_3$ mixture was added and stirred for 1 hour. Water (100 mL) was added, and the mixture was extracted with ethyl acetate. The organic extract was washed twice with saturated $CuSO_4$ mixture, dried, filtered, and concentrated. The residue was purified by flash chromatography, eluted with 50% ethyl acetate/petroleum ether to give the title compound. $^1$H NMR (500 MHz, methanol-$d_4$) δ ppm 5.29 (t, 1H), 5.08 (td, 2H), 4.48 (dd, 1H), 4.23 (d, 1H), 3.71 (s, 3H), 3.04 (d, 1H), 2.03 (s, 3H), 1.99 (s, 3H), 1.98 (s, 4H).

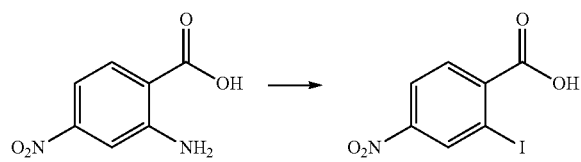 [SMILES: Nc1cc([N+](=O)[O-])ccc1C(=O)O ; O=C(O)c1ccc([N+](=O)[O-])cc1I]

Example 1.2.10: 2-iodo-4-nitrobenzoic acid

A 3-L fully jacketed flask equipped with a mechanical stirrer, temperature probe and an addition funnel under a nitrogen atmosphere, was charged with 2-amino-4-nitrobenzoic acid (69.1 g, Combi-Blocks) and sulfuric acid, 1.5 M aqueous (696 mL). The resulting suspension was cooled to 0° C. internal temperature, and a mixture of sodium nitrite (28.8 g) in water (250 mL) was added dropwise over 43 minutes with the temperature kept below 1° C. The reaction was stirred at ca. 0° C. for 1 hour. A mixture of potassium iodide (107 g) in water (250 mL) was added dropwise over 44 minutes with the internal temperature kept below 1° C. (Initially addition was exothermic and there was gas evolution). The reaction was stirred 1 hour at 0° C. The temperature was raised to 20° C. and then stirred at ambient temperature overnight. The reaction mixture became a suspension. The reaction mixture was filtered, and the collected solid was washed with water. The wet solid (~108 g) was stirred in 10% sodium sulfite (350 mL, with ~200 mL water used to wash in the solid) for 30 minutes. The suspension was acidified with concentrated hydrochloric acid (35 mL), and the solid was collected by filtration and washed with water. The solid was slurried in water (1 L) and re-filtered, and the solid was left to dry in the funnel overnight. The solid was then dried in a vacuum oven for 2 hours at 60° C. The resulting solid was triturated with dichloromethane (500 mL), and the suspension was filtered and washed with additional dichloromethane. The solid was air-dried to give the title compound.

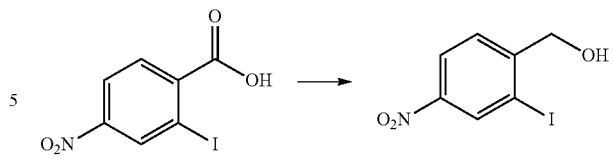

Example 1.2.11: (2-iodo-4-nitrophenyl)methanol

A flame-dried 3-L 3-necked flask was charged with Example 1.2.10 (51.9 g) and tetrahydrofuran (700 mL). The mixture was cooled in an ice bath to 0.5° C., and borane-tetrahydrofuran complex (443 mL, 1 M in tetrahydrofuran) was added dropwise (gas evolution) over 50 minutes, reaching a final internal temperature of 1.3° C. The reaction mixture was stirred for 15 minutes, and the ice bath was removed. The reaction was left to come to ambient temperature over 30 minutes. A heating mantle was installed, and the reaction was heated to an internal temperature of 65.5° C. for 3 hours, and then allowed to cool to room temperature while stirring overnight. The reaction mixture was cooled in an ice bath to 0° C. and quenched by dropwise addition of methanol (400 mL). After a brief incubation period, the temperature rose quickly to 2.5° C. with gas evolution. After the first 100 mL are added over ~30 minutes, the addition was no longer exothermic, and the gas evolution ceased. The ice bath was removed, and the mixture was stirred at ambient temperature under nitrogen overnight. The mixture was concentrated to a solid, dissolved in dichloromethane/methanol and adsorbed on to silica gel (~150 g). The residue was loaded on a plug of silica gel (3000 mL) and eluted with dichloromethane to give the title compound.

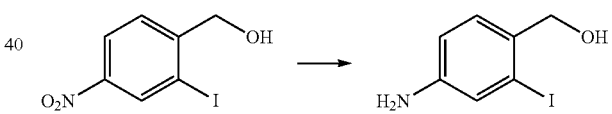

Example 1.2.12: (4-amino-2-iodophenyl)methanol

A 5-L flask equipped with a mechanical stirrer, heating mantle controlled by a JKEM temperature probe and a condenser was charged with Example 1.2.11 (98.83 g) and ethanol (2 L). The reaction was stirred rapidly, and iron (99 g) was added, followed by a mixture of ammonium chloride (20.84 g) in water (500 mL). The reaction was heated over the course of 20 minutes to an internal temperature of 80.3° C., where it began to reflux vigorously. The mantle was dropped until the reflux calmed. Thereafter, the mixture was heated to 80° C. for 1.5 hours. The reaction was filtered hot through a membrane filter, and the iron residue was washed with hot 50% ethyl acetate/methanol (800 mL). The eluent was passed through a diatomaceous earth pad, and the filtrate was concentrated. The residue was partitioned between 50% brine (1500 mL) and ethyl acetate (1500 mL). The layers were separated, and the aqueous layer was extracted with ethyl acetate (400 mL×3). The combined organic layers were dried over sodium sulfate, filtered, and concentrated to give the title compound, which was used without further purification.

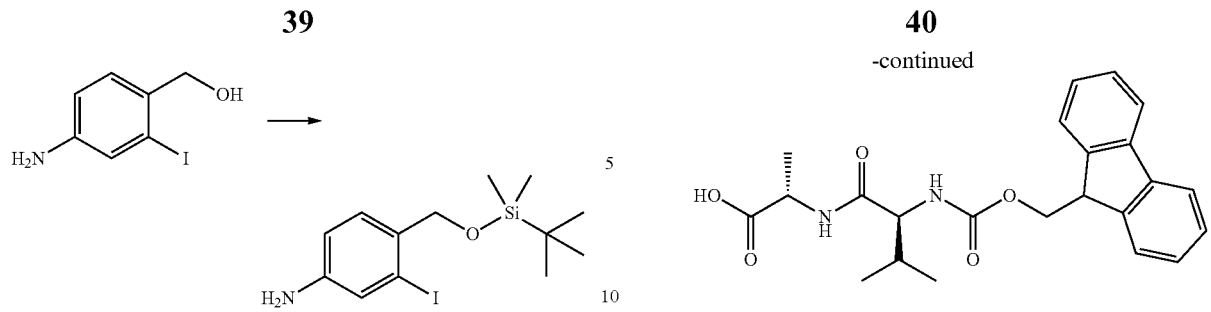

Example 1.2.13: 4-({[tert-butyl(dimethyl)silyl]oxy}methyl)-3-iodoaniline

A 5-L flask with a mechanical stirrer was charged with Example 1.2.12 (88 g) and dichloromethane (2 L). The suspension was cooled in an ice bath to an internal temperature of 2.5° C., and tert-butylchlorodimethylsilane (53.3 g) was added portion-wise over 8 minutes. After 10 minutes, 1H-imidazole (33.7 g) was added portionwise to the cold reaction. The reaction was stirred for 90 minutes while the internal temperature rose to 15° C. The reaction mixture was diluted with water (3 L) and dichloromethane (1 L). The layers were separated, and the organic layer was dried over sodium sulfate, filtered, and concentrated to an oil. The residue was purified by silica gel chromatography (1600 g silica gel), eluted with a gradient of 0-25% ethyl acetate in heptane, to give the title compound.

Example 1.2.14: (2S)-2-{[(2S)-2-({[(9H-fluoren-9-yl)methoxy]carbonyl}amino)-3-methylbutanoyl]amino}propanoic acid To a mixture of (9H-fluoren-9-yl)methyl {(2RS)-1-[(2,5-dioxopyrrolidin-1-yl)oxy]-3-methyl-1-oxobutan-2-yl}carbamate (6.5 g) in dimethoxyethane (40 mL) was added (2S)-2-aminopropanoic acid (1.393 g) and sodium bicarbonate (1.314 g) in water (40 mL). Tetrahydrofuran (20 mL) was added to aid solubility. The resulting mixture was stirred at room temperature for 16 hours. Aqueous citric acid (15%, 75 mL) was added, and the mixture was extracted with 10% 2-propanol in ethyl acetate (2×100 mL). A precipitate formed in the organic layer. The combined organic layers were washed with water (2×150 mL). The organic layer was concentrated under reduced pressure and then triturated with diethyl ether (80 mL). After brief sonication, the title compound was collected by filtration and air-dried. MS (ESI) m/z 411 (M+H)$^+$.

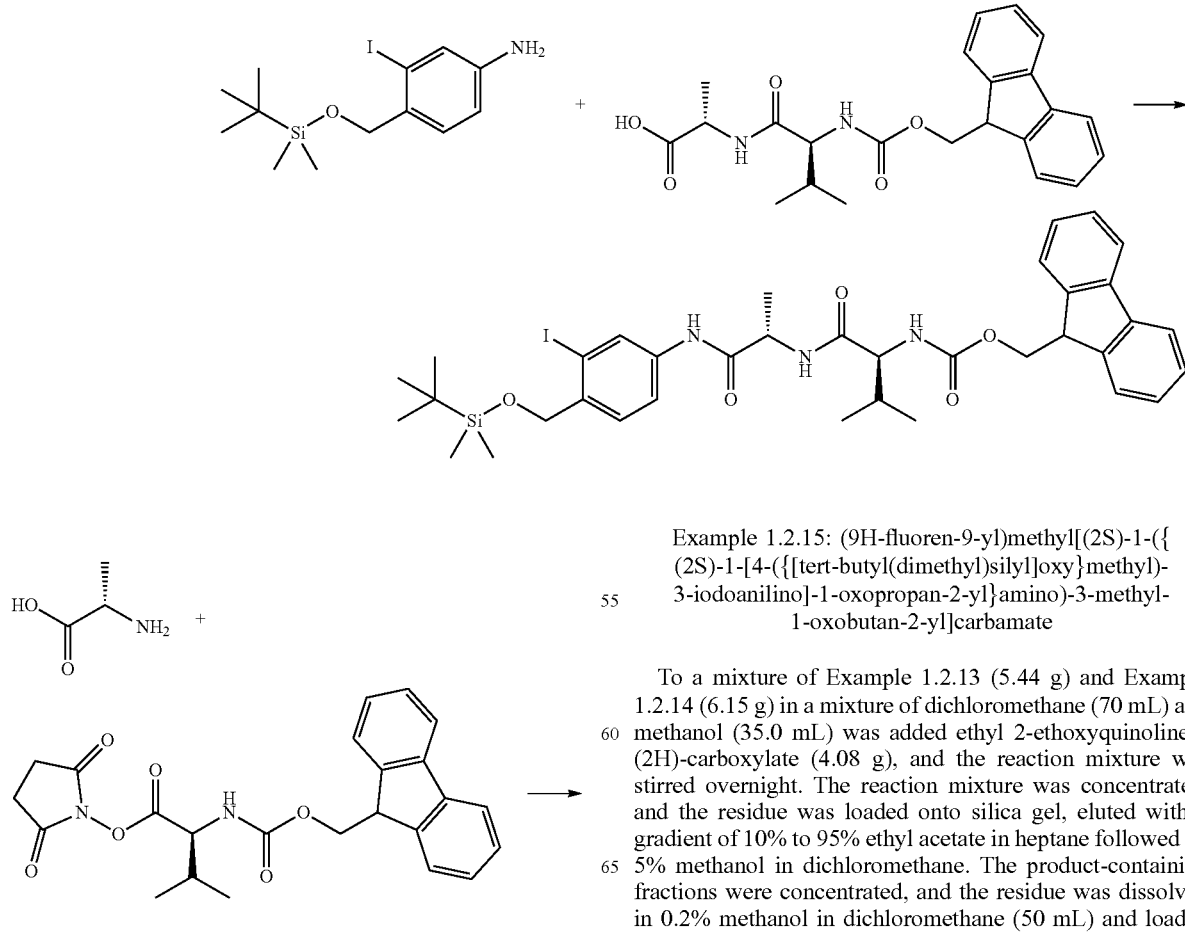

Example 1.2.15: (9H-fluoren-9-yl)methyl[(2S)-1-({(2S)-1-[4-({[tert-butyl(dimethyl)silyl]oxy}methyl)-3-iodoanilino]-1-oxopropan-2-yl}amino)-3-methyl-1-oxobutan-2-yl]carbamate To a mixture of Example 1.2.13 (5.44 g) and Example 1.2.14 (6.15 g) in a mixture of dichloromethane (70 mL) and methanol (35.0 mL) was added ethyl 2-ethoxyquinoline-1(2H)-carboxylate (4.08 g), and the reaction mixture was stirred overnight. The reaction mixture was concentrated, and the residue was loaded onto silica gel, eluted with a gradient of 10% to 95% ethyl acetate in heptane followed by 5% methanol in dichloromethane. The product-containing fractions were concentrated, and the residue was dissolved in 0.2% methanol in dichloromethane (50 mL) and loaded onto silica gel eluted with a gradient of 0.2% to 2% methanol in dichloromethane. The product containing fractions were collected to give the title compound. MS (ESI) m/z 756.0 (M+H)⁺.

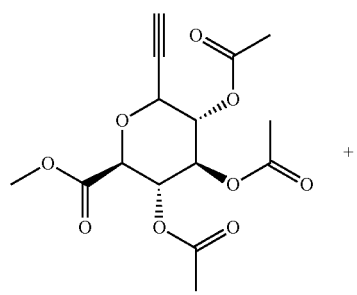

+

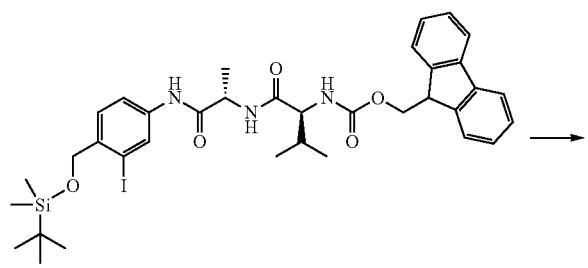

→

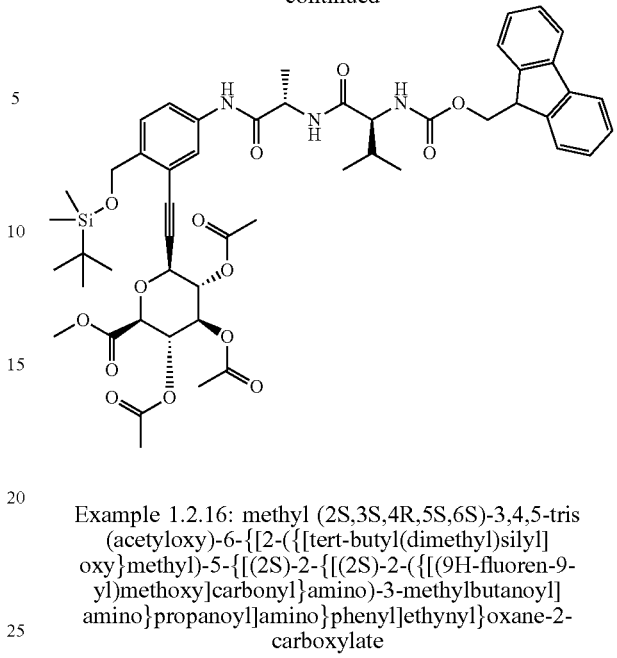

Example 1.2.16: methyl (2S,3S,4R,5S,6S)-3,4,5-tris(acetyloxy)-6-{[2-({[tert-butyl(dimethyl)silyl]oxy}methyl)-5-{[(2S)-2-{[(2S)-2-({[(9H-fluoren-9-yl)methoxy]carbonyl}amino)-3-methylbutanoyl]amino}propanoyl]amino}phenyl]ethynyl}oxane-2-carboxylate A mixture of Example 1.2.9 (4.500 g), Example 1.2.15 (6.62 g), copper(I) iodide (0.083 g) and bis(triphenylphosphine)palladium(II) dichloride (0.308 g) were combined in vial and degassed. N,N-Dimethylformamide (45 mL) and N-ethyl-N-(propan-2-yl)propan-2-amine (4.55 mL) were added, and the reaction vessel was flushed with nitrogen and stirred at room temperature overnight. The reaction was partitioned between water (100 mL) and ethyl acetate (250 mL). The layers were separated, and the organic layer was dried over magnesium sulfate, filtered, and concentrated. The residue was purified by silica gel chromatography, eluted with a gradient of 5% to 95% ethyl acetate in heptane. The product containing fractions were collected and concentrated. The residue was purified by silica gel chromatography, eluted with a gradient of 0.25% to 2.5% methanol in dichloromethane to give the title compound. MS (ESI) m/z 970.4 (M+H)⁺.

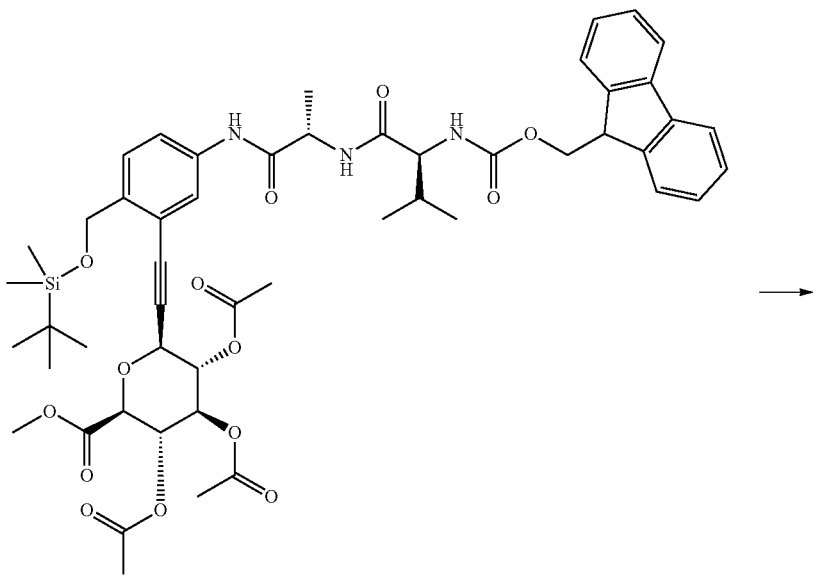

→

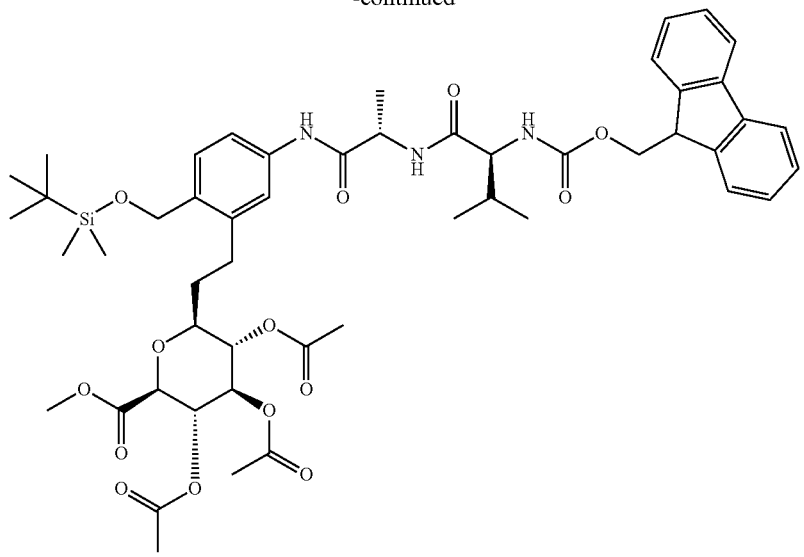

Example 1.2.17: methyl (2S,3S,4R,5S,6S)-3,4,5-tris(acetyloxy)-6-{2-[2-({[tert-butyl(dimethyl)silyl]oxy}methyl)-5-{[(2S)-2-{[(2S)-2-({[(9H-fluoren-9-yl)methoxy]carbonyl}amino)-3-methylbutanoyl]amino}propanoyl]amino}phenyl]ethyl}oxane-2-carboxylate Example 1.2.16 (4.7 g) and tetrahydrofuran (95 mL) were added to 5% Pt/C (2.42 g, wet) in a 50 mL pressure bottle and shaken for 90 minutes at room temperature under 50 psi of hydrogen. The reaction mixture was filtered and concentrated to give the title compound. MS (ESI) m/z 974.6 (M+H)$^+$.

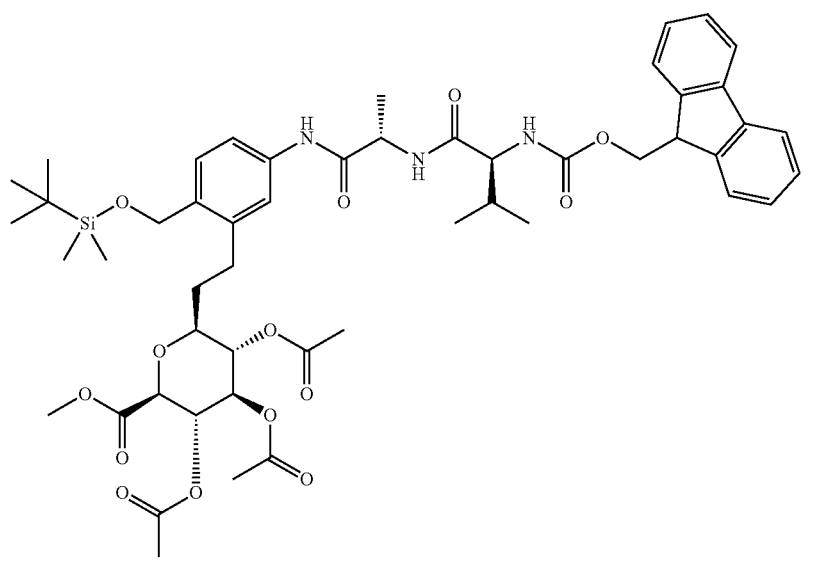

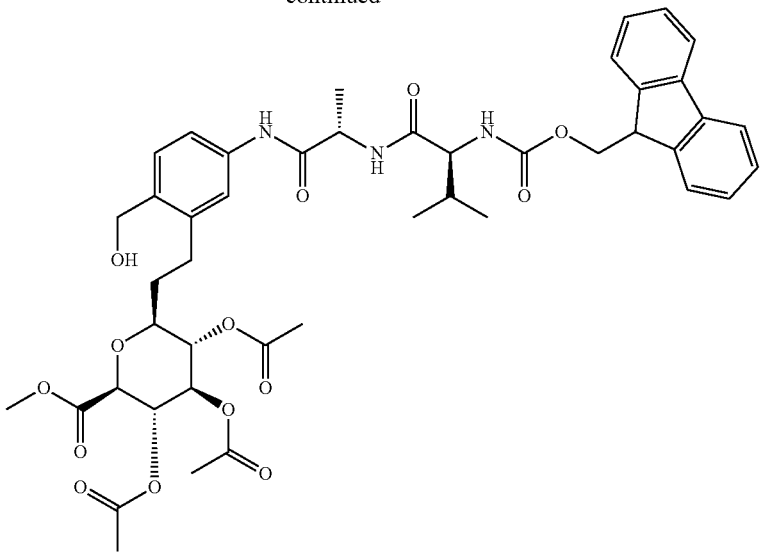

Example 1.2.18: methyl (2S,3S,4R,5S,6S)-3,4,5-tris(acetyloxy)-6-{2-[5-{[(2S)-2-{[(2S)-2-({[(9H-fluoren-9-yl)methoxy]carbonyl}amino)-3-methylbutanoyl]amino}propanoyl]amino}-2-(hydroxymethyl)phenyl]ethyl}oxane-2-carboxylate A mixture of Example 1.2.17 (5.4 g) in tetrahydrofuran (7 mL), water (7 mL) and glacial acetic acid (21 mL) was stirred overnight at room temperature. The reaction mixture was diluted with ethyl acetate (200 mL) and washed with water (100 mL), saturated aqueous NaHCO$_3$ (100 mL), and brine (100 mL). The organic fraction was dried over magnesium sulfate, filtered, and concentrated. The residue was purified by silica gel chromatography, eluted with a gradient of 0.5% to 5% methanol in dichloromethane, to give the title compound. MS (ESI) m/z 860.4 (M+H)$^+$.

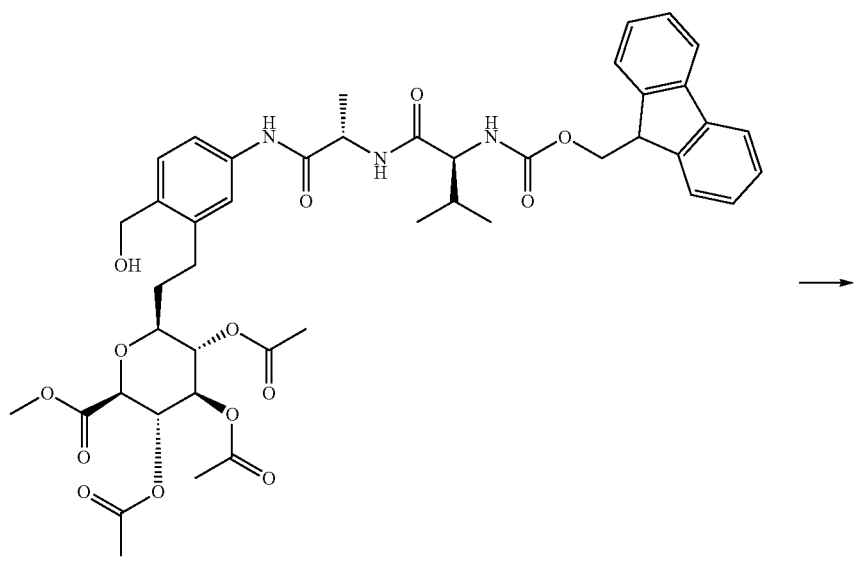

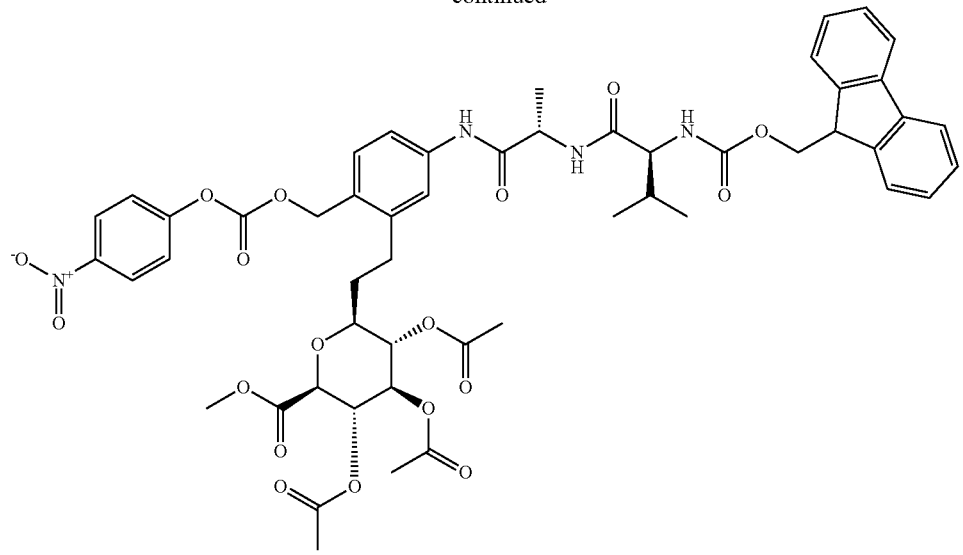

Example 1.2.19: methyl (2S,3S,4R,5S,6S)-3,4,5-tris(acetyloxy)-6-{2-[5-{[(2S)-2-{[(2S)-2-({[(9H-fluoren-9-yl)methoxy]carbonyl}amino)-3-methylbutanoyl]amino}propanoyl]amino}-2-({[(4-nitrophenoxy)carbonyl]oxy}methyl)phenyl]ethyl}oxane-2-carboxylate To a mixture of Example 1.2.18 (4.00 g) and bis(4-nitrophenyl) carbonate (2.83 g) in acetonitrile (80 mL) was added N-ethyl-N-(propan-2-yl)propan-2-amine (1.22 mL) at room temperature. After stirring overnight, the reaction was concentrated, dissolved in dichloromethane (250 mL) and washed with saturated aqueous NaHCO₃ mixture (4×150 mL). The organic layer was dried over magnesium sulfate, filtered, and concentrated. The resulting foam was purified by silica gel chromatography, eluted with a gradient of 5% to 75% ethyl acetate in hexanes to give the title compound. MS (ESI) m/z 1025.5 (M+H)⁺.

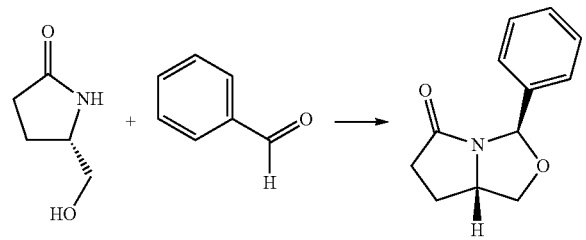 [SMILES: O=C1CC[C@@H](CO)N1 ; O=Cc1ccccc1 ; O=C1CC[C@H]2CO[C@H](c3ccccc3)N12]

Example 1.3.1: (3R,7aS)-3-phenyltetrahydro-3H,5H-pyrrolo[1,2-c][1,3]oxazol-5-one A mixture of (5S)-5-(hydroxymethyl)pyrrolidin-2-one (25 g), benzaldehyde (25.5 g) and para-toluenesulfonic acid monohydrate (0.50 g) in toluene (300 mL) was heated to reflux using a Dean-Stark trap under a drying tube for 16 hours. The reaction mixture was cooled to room temperature, and the solvent was decanted from the insoluble materials. The decanted organic layer was washed with saturated aqueous sodium bicarbonate mixture (twice) and brine (once). The organic layer was dried over sodium sulfate, filtered, and concentrated under reduced pressure. The residue was purified by flash chromatography on silica gel, eluted with 35/65 heptane/ethyl acetate, to give the title compound. MS (DCI) m/z 204.0 (M+H)⁺.

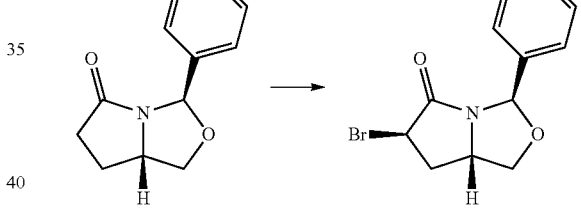

Example 1.3.2: (3R,6R,7aS)-6-bromo-3-phenyltetrahydro-3H,5H-pyrrolo[1,2-c][1,3]oxazol-5-one To a cold (−77° C.) mixture of Example 1.3.1 (44.6 g) in tetrahydrofuran (670 mL) was added lithium bis(trimethylsilyl)amide (1.0 M in hexanes, 250 mL) dropwise over 40 minutes, keeping the reaction mixture temperature less than −73° C. The reaction was stirred at −77° C. for 2 hours, and bromine (12.5 mL) was added dropwise over 20 minutes, keeping the reaction mixture temperature less than −64° C. The reaction was stirred at −77° C. for 75 minutes and was quenched by the addition of cold 10% aqueous sodium thiosulfate (150 mL) to the −77° C. reaction. The mixture was warmed to room temperature and partitioned between half-saturated aqueous ammonium chloride and ethyl acetate. The layers were separated, and the organic layer was washed with water and brine, dried over sodium sulfate, filtered, and concentrated under reduced pressure. The residue was purified by silica gel chromatography, eluted with gradients of 80/20, 75/25, and 70/30 heptane/ethyl acetate to give the title compound. MS (DCI) m/z 299.0 and 301.0 (M+NH₃+H)⁺.

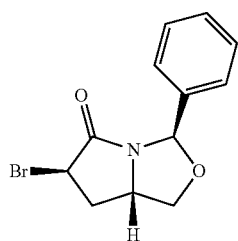

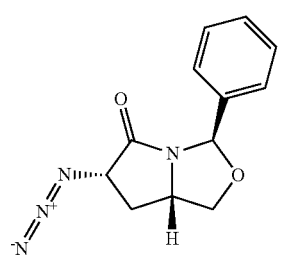

Example 1.3.3: (3R,6S,7aS)-6-azido-3-phenyltetrahydro-3H,5H-pyrrolo[1,2-c][1,3]oxazol-5-one To a mixture of Example 1.3.2 (19.3 g) in N,N-dimethylformamide (100 mL) was added sodium azide (13.5 g). The reaction was heated to 60° C. for 2.5 hours. The reaction was cooled to room temperature and quenched by the addition of water (500 mL) and ethyl acetate (200 mL). The layers were separated, and the organic layer was washed brine. The combined aqueous layers were back-extracted with ethyl acetate (50 mL). The combined organic layers were dried with sodium sulfate, filtered, and concentrated under reduced pressure. The residue was purified by silica gel chromatography, eluted with 78/22 heptane/ethyl acetate, to give the title compound. MS (DCI) m/z 262.0 $(M+NH_3+H)^+$.

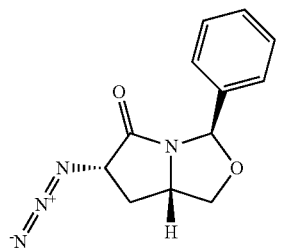

Example 1.3.4: (3R,6S,7aS)-6-amino-3-phenyltetrahydro-3H,5H-pyrrolo[1,2-c][1,3]oxazol-5-one To a mixture of Example 1.3.3 (13.5 g) in tetrahydrofuran (500 mL) and water (50 mL) was added polymer-supported triphenylphosphine (55 g, Aldrich catalog #366455, loading—3 mmol/g). The reaction mixture was mechanically stirred overnight at room temperature. The reaction mixture was filtered through diatomaceous earth, eluted with ethyl acetate and toluene. The mixture was concentrated under reduced pressure, dissolved in dichloromethane (100 mL), dried with sodium sulfate, then filtered and concentrated to give the title compound, which was used in the subsequent step without further purification. MS (DCI) m/z 219.0 $(M+H)^+$.

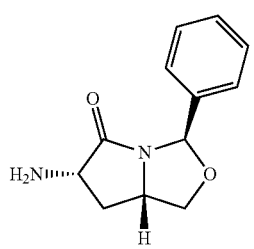

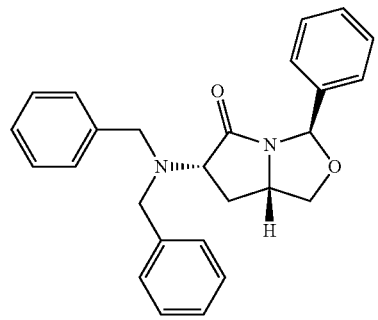

Example 1.3.5: (3R,6S,7aS)-6-(dibenzylamino)-3-phenyltetrahydro-3H,5H-pyrrolo[1,2-c][1,3]oxazol-5-one To a mixture of Example 1.3.4 (11.3 g) in N,N-dimethylformamide (100 mL) was added potassium carbonate (7.0 g), potassium iodide (4.2 g), and benzyl bromide (14.5 mL). The reaction mixture was stirred at room temperature overnight and quenched by the addition of water and ethyl acetate. The layers were separated, and the organic layer was washed with brine. The combined aqueous layers were back-extracted with ethyl acetate. The combined organic layers were dried with sodium sulfate, filtered, and concentrated under reduced pressure. The residue was purified by silica gel chromatography, eluted with a gradient of 10 to 15% ethyl acetate in heptane to give a solid that was triturated with heptane to give the title compound. MS (DCI) m/z 399.1 $(M+H)^+$.

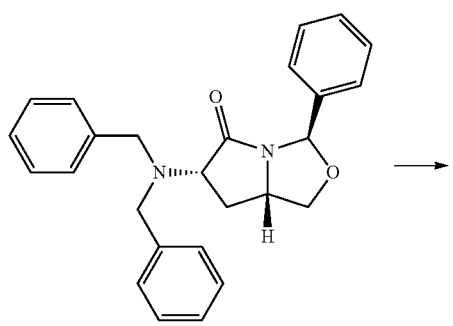

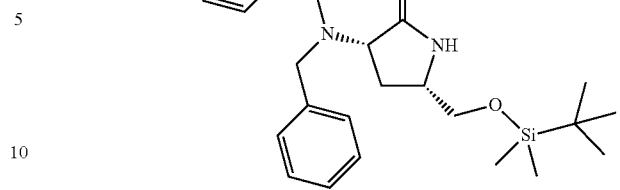

Example 1.3.7: (3S,5S)-5-({[tert-butyl(dimethyl)silyl]oxy}methyl)-3-(dibenzylamino)pyrrolidin-2-one To a mixture of Example 1.3.6 (9.3 g) and 1H-imidazole (2.2 g) in N,N-dimethylformamide was added tert-butylchlorodimethylsilane (11.2 mL, 50 weight % in toluene), and the reaction mixture was stirred overnight. The reaction mixture was quenched by the addition of water and diethyl ether. The layers were separated, and the organic layer was washed with brine. The combined aqueous layers were back-extracted with diethyl ether. The combined organic layers were dried with sodium sulfate, filtered, and concentrated under reduced pressure. The residue was purified by silica gel chromatography, eluted with 35% ethyl acetate in heptane, to give the title compound. MS (DCI) m/z 425.1 (M+H)$^+$.

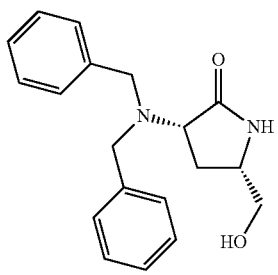

Example 1.3.6: (3S,5S)-3-(dibenzylamino)-5-(hydroxymethyl)pyrrolidin-2-one

To a mixture of Example 1.3.5 (13 g) in tetrahydrofuran (130 mL) was added para-toluene sulfonic acid monohydrate (12.4 g) and water (50 mL), and the reaction was heated to 65° C. for 6 days. The reaction was cooled to room temperature and quenched by the addition of saturated aqueous sodium bicarbonate and ethyl acetate. The layers were separated, and the organic layer was washed with brine. The combined aqueous layers were back-extracted with ethyl acetate. The combined organic layers were dried with sodium sulfate, filtered, and concentrated under reduced pressure. The waxy solids were triturated with heptane (150 mL) to give the title compound. MS (DCI) m/z 311.1 (M+H)$^+$.

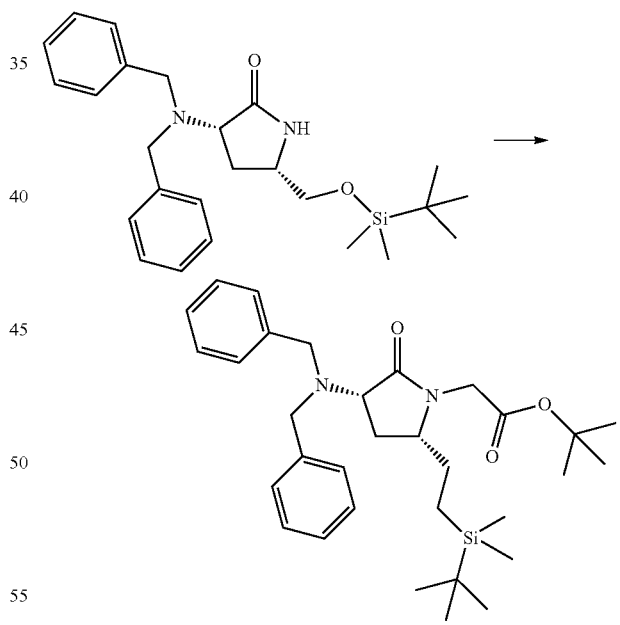

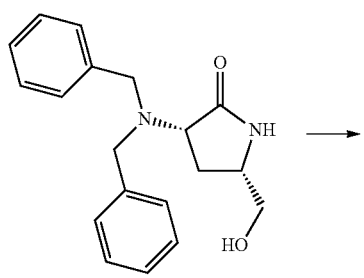

Example 1.3.8: tert-butyl [(3S,5S)-5-({[tert-butyl(dimethyl)silyl]oxy}methyl)-3-(dibenzylamino)-2-oxopyrrolidin-1-yl]acetate To a cold (0° C.) mixture of Example 1.3.7 (4.5 g) in tetrahydrofuran (45 mL) was added 95% sodium hydride (320 mg) in two portions. The cold mixture was stirred for 40 minutes, and tert-butyl 2-bromoacetate (3.2 mL) was added. The reaction mixture was warmed to room temperature and stirred overnight. The reaction was quenched by the addition of water and ethyl acetate. The layers were separated, and the organic layer was washed with brine. The combined aqueous layers were back-extracted with ethyl acetate. The combined organic layers were dried with sodium sulfate, filtered, and concentrated under reduced pressure. The residue was purified by silica gel chromatography, eluted with a gradient of 5-12% ethyl acetate in heptane, to give the title compound. MS (DCI) m/z 539.2 (M+H)$^+$.

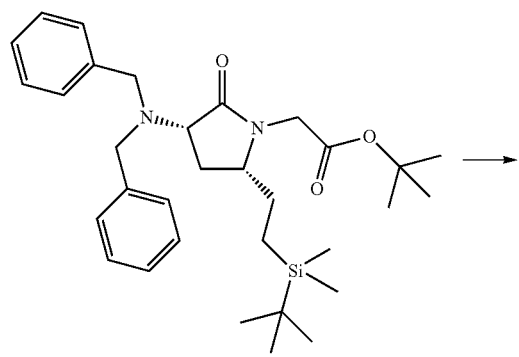

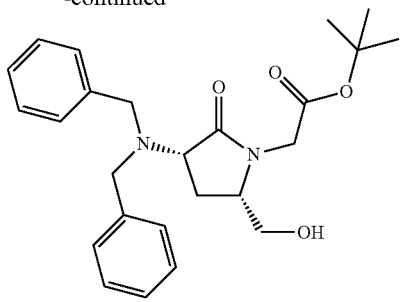

Example 1.3.9: tert-butyl [(3S,5S)-3-(dibenzylamino)-5-(hydroxymethyl)-2-oxopyrrolidin-1-yl] acetate To a mixture of Example 1.3.8 (5.3 g) in tetrahydrofuran (25 mL) was added tetrabutylammonium fluoride (11 mL, 1.0 M in 95/5 tetrahydrofuran/water). The reaction mixture was stirred at room temperature for one hour and then quenched by the addition of saturated aqueous ammonium chloride, water and ethyl acetate. The layers were separated, and the organic layer was washed with brine. The combined aqueous layers were back-extracted with ethyl acetate. The combined organic layers were dried with sodium sulfate, filtered, and concentrated under reduced pressure. The residue was purified by silica gel chromatography, eluted with 35% ethyl acetate in heptane, to give the title compound. MS (DCI) m/z 425.1 (M+H)$^+$.

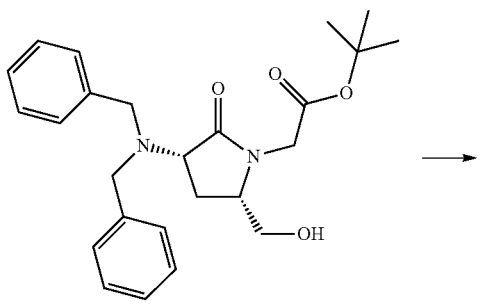

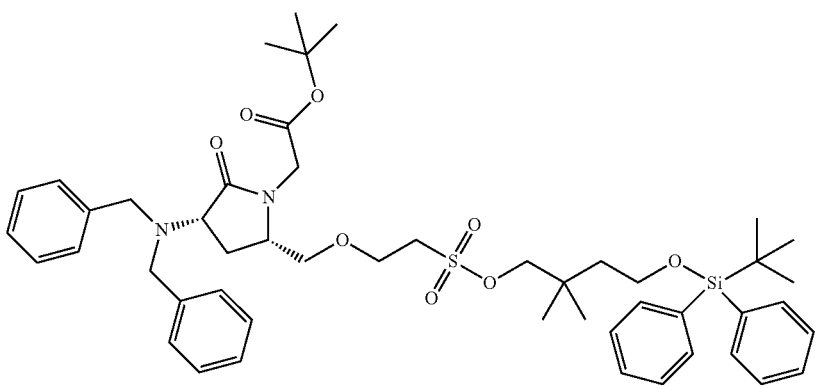

Example 1.3.10: tert-butyl [(3S,5S)-3-(dibenzylamino)-2-oxo-5-(8,8,13,13-tetramethyl-5,5-dioxo-12,12-diphenyl-2,6,11-trioxa-5λ⁶-thia-12-silatetradecan-1-yl)pyrrolidin-1-yl]acetate To a mixture of Example 1.3.9 (4.7 g) in dimethyl sulfoxide (14 mL) was added a mixture of 4-((tert-butyldiphenylsilyl)oxy)-2,2-dimethylbutyl ethenesulfonate (14.5 g) in dimethyl sulfoxide (14 mL). Potassium carbonate (2.6 g) and water (28 µL) were added, and the reaction mixture was heated at 60° C. under nitrogen for one day. The reaction was cooled to room temperature and then quenched by the addition of brine, water and diethyl ether. The layers were separated, and the organic layer was washed with brine. The combined aqueous layers were back-extracted with diethyl ether. The combined organic layers were dried with sodium sulfate, filtered, and concentrated under reduced pressure. The residue was purified by silica gel chromatography, eluted with a gradient of 15-25% ethyl acetate in heptane to give the title compound. MS (ESI+) m/z 871.2 (M+H)⁺.

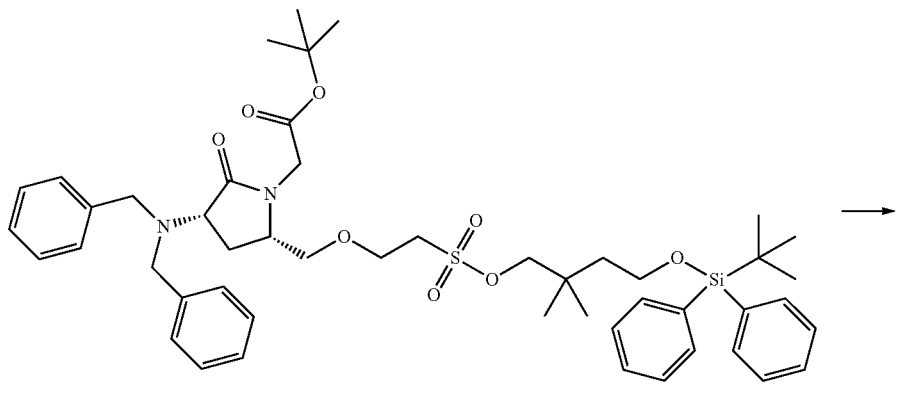

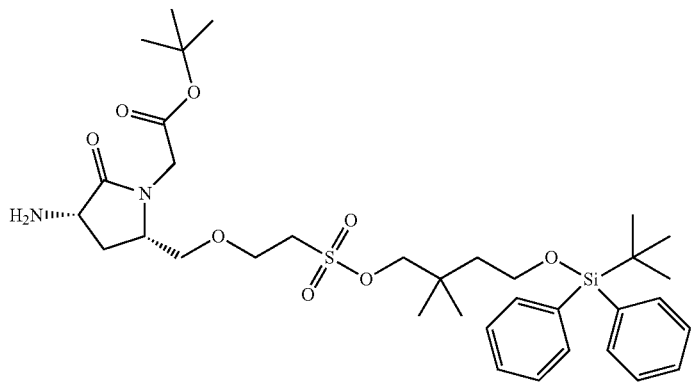

Example 1.3.11: tert-butyl [(3S,5S)-3-amino-2-oxo-5-(8,8,13,13-tetramethyl-5,5-dioxo-12,12-diphenyl-2,6,11-trioxa-5λ⁶-thia-12-silatetradecan-1-yl)pyrrolidin-1-yl]

Example 1.3.10 (873 mg) was dissolved in ethyl acetate (5 mL) and methanol (15 mL), and palladium hydroxide on carbon, 20% by weight (180 mg) was added. The reaction mixture was stirred under a hydrogen atmosphere (30 psi) at room temperature for 30 hours, then at 50° C. for one hour. The reaction mixture was cooled to room temperature, filtered, and concentrated to give the title compound. MS (ESI+) m/z 691.0 (M+H)⁺.

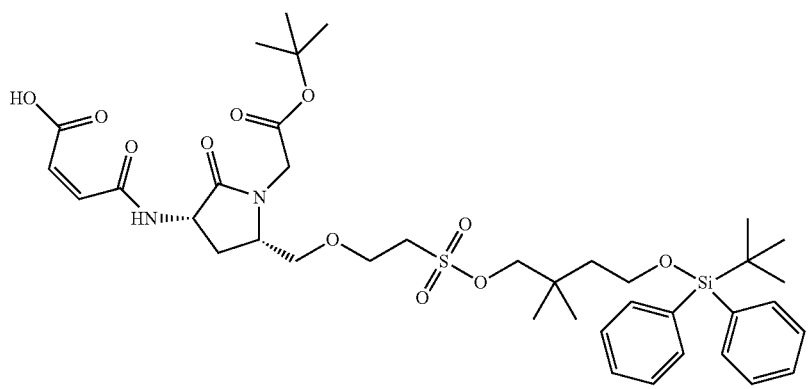

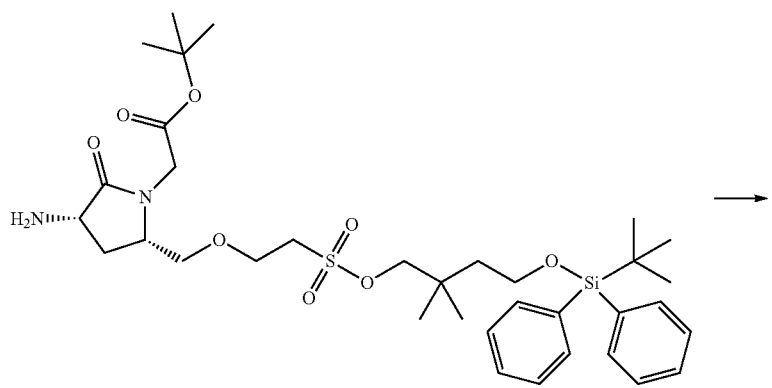

Example 1.3.12: (2Z)-4-{[(3S,5S)-1-(2-tert-butoxy-2-oxoethyl)-2-oxo-5-(8,8,13,13-tetramethyl-5,5-dioxo-12,12-diphenyl-2,6,11-trioxa-5λ⁶-thia-12-silatetradecan-1-yl)pyrrolidin-3-yl]amino}-4-oxobut-2-enoic acid Maleic anhydride (100 mg) was dissolved in dichloromethane (0.90 mL), and a mixture of Example 1.3.11 (650 mg) in dichloromethane (0.90 mL) was added dropwise followed by heating at 40° C. for 2 hours. The reaction mixture was directly purified by silica gel chromatography, eluted with a gradient of 1.0-2.5% methanol in dichloromethane containing 0.2% acetic acid. After concentrating the product-bearing fractions, toluene (10 mL) was added, and the mixture was concentrated again to give the title compound. MS (ESI−) m/z 787.3 (M−H)⁻.

Example 1.3.13: tert-butyl [(3S,5S)-3-(2,5-dioxo-2,5-dihydro-1H-pyrrol-1-yl)-2-oxo-5-(8,8,13,13-tetramethyl-5,5-dioxo-12,12-diphenyl-2,6,11-trioxa-5λ⁶-thia-12-silatetradecan-1-yl)pyrrolidin-1-yl] acetate Example 1.3.12 (560 mg) was slurried in toluene (7 mL), and triethylamine (220 μL) and sodium sulfate (525 mg) were added. The reaction was heated at reflux under a nitrogen atmosphere for 6 hours, and the reaction mixture was stirred at room temperature overnight. The mixture was filtered, and the solids were rinsed with ethyl acetate. The eluent was concentrated under reduced pressure, and the residue was purified by silica gel chromatography, eluted with 45/55 heptane/ethyl acetate to give the title compound.

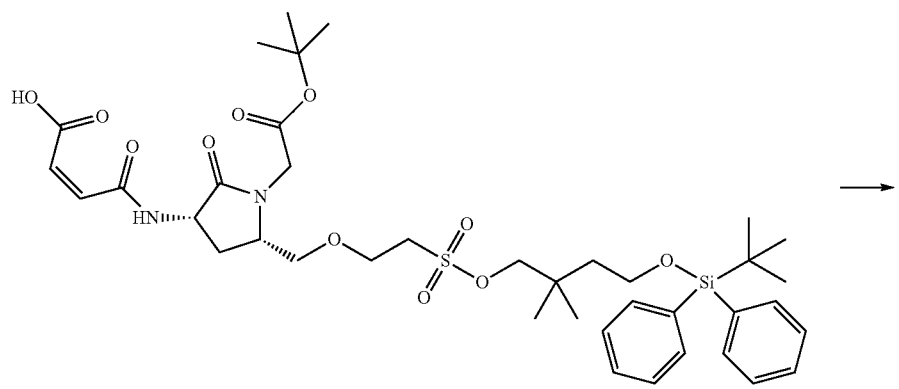

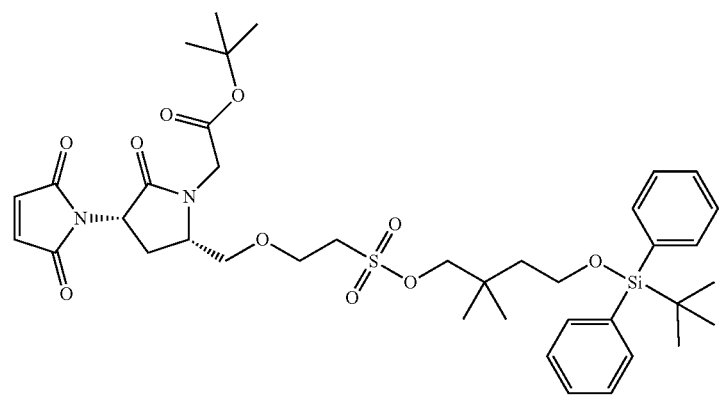

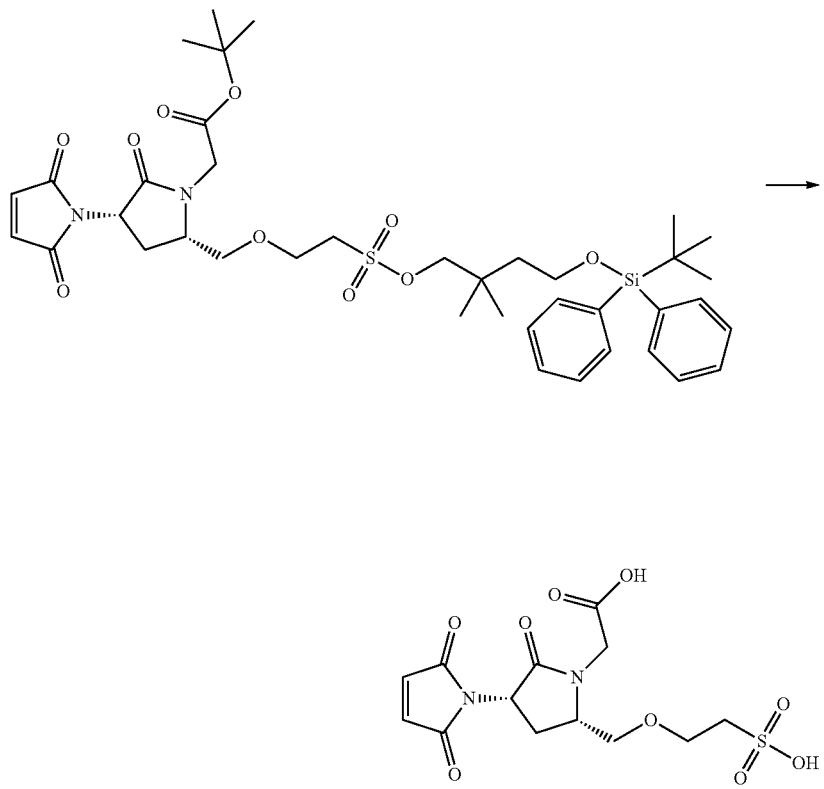

Example 1.3.14: {(3S,5S)-3-(2,5-dioxo-2,5-dihydro-1H-pyrrol-1-yl)-2-oxo-5-[(2-sulfoethoxy)methyl]pyrrolidin-1-yl}acetic acid Example 1.3.13 (1.2 g) was dissolved in trifluoroacetic acid (15 mL) and heated to 65-70° C. under nitrogen overnight. The trifluoroacetic acid was removed under reduced pressure. The residue was dissolved in acetonitrile (2.5 mL) and purified by preparative reverse-phase high-pressure liquid chromatography on a Phenomenex® Luna® C18(2) AXIA™ column (250×50 mm, 10 μm particle size) using a gradient of 5-75% acetonitrile containing 0.1% trifluoroacetic acid in water (70 mL/minute) over 30 minutes, to give the title compound. MS (ESI−) m/z 375.2 (M−H)−.

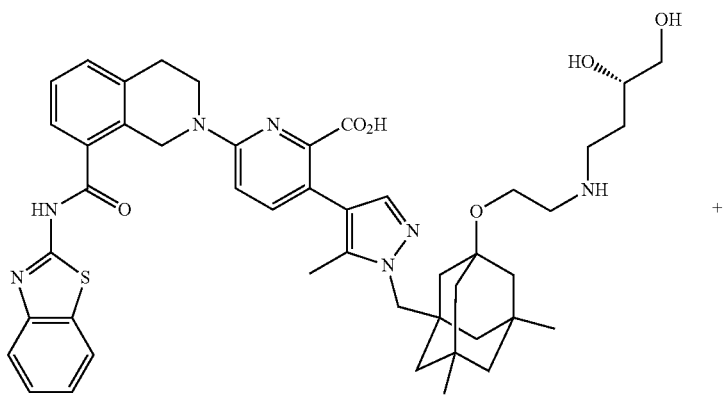

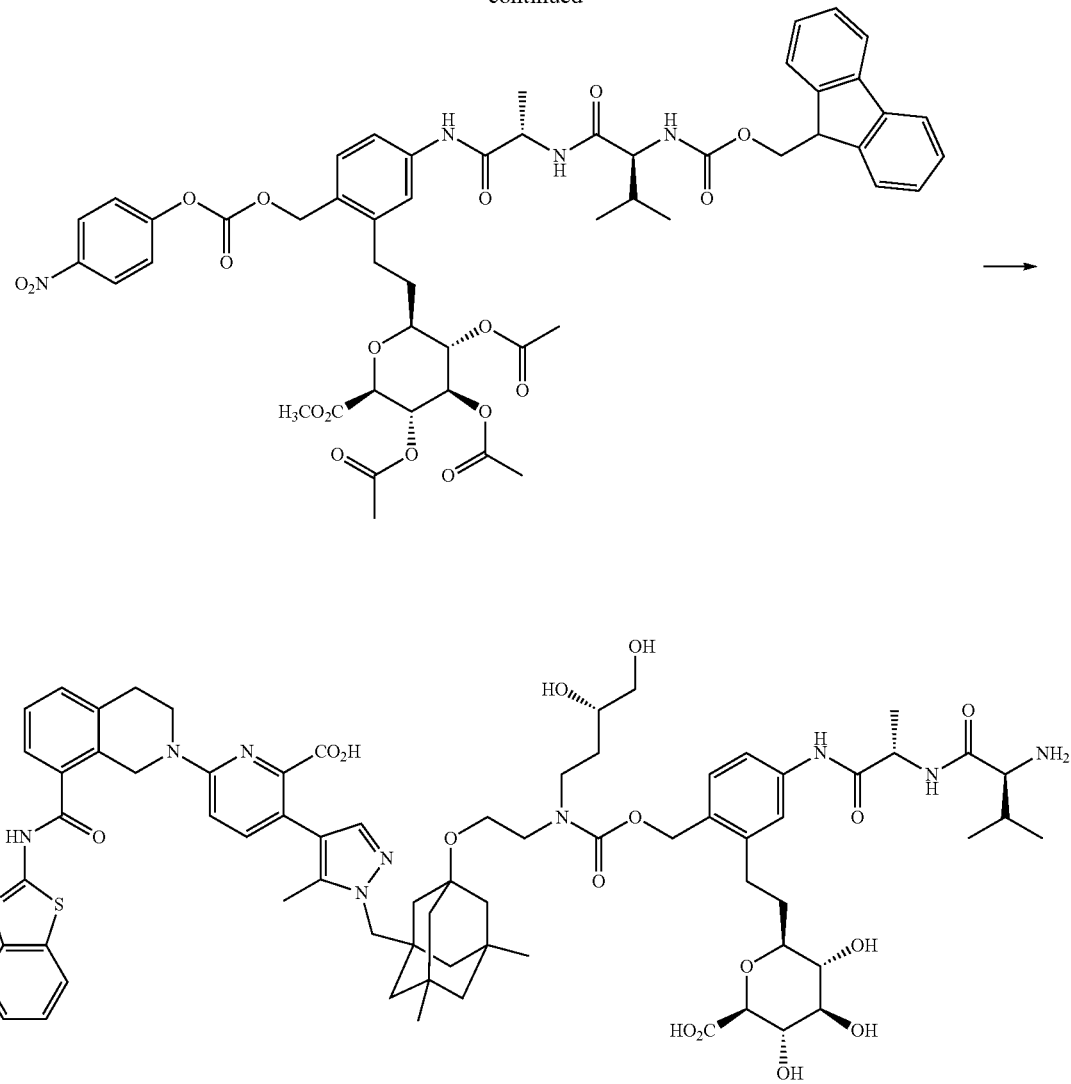

Example 1.4.1: 3-[1-({3-[2-({[(4-{[(2S)-2-{[(2S)-2-amino-3-methylbutanoyl]amino}propanoyl]amino}-2-{2-[(2S,3R,4R,5S,6S)-6-carboxy-3,4,5-trihydroxyoxan-2-yl]ethyl}phenyl)methoxy]carbonyl}[(3S)-3,4-dihydroxybutyl]amino)ethoxy]-5,7-dimethyladamantan-1-yl}methyl)-5-methyl-1H-pyrazol-4-yl]-6-{8-[(1,3-benzothiazol-2-yl)carbamoyl]-3,4-dihydroisoquinolin-2(1H)-yl}pyridine-2-carboxylic acid To a suitably sized reactor was charged Example 1.1.17 (5.17 g), Example 1.2.19 (6.99 g), N,N-dimethylformamide (50 mL) and N,N-diisopropylethylamine (7.6 mL). After the solids were dissolved, 1-hydroxybenzotriazole hydrate (1.21 g) was charged to the reactor, and the reaction progress was monitored by HPLC (Ascentis® Express® C18, 4.6×150 mm, 2.7 μm, 1.5 mL/minute flow rate, eluted with a gradient of 40 to 100% acetonitrile in 0.05% $HClO_4$ in water over 18 minutes). After coupling was determined to be complete, tetrahydrofuran (62 mL) was charged to the reactor, and the reaction mixture was cooled to 0° C. Lithium methoxide (62 mL, 1.0 M solution in methanol) was charged over 1 hour, and the reaction mixture was allowed to warm to ambient temperature. The reaction progress was monitored by HPLC (Ascentis® Express® C18, 4.6×150 mm, 2.7 μm, 1.5 mL/minute flow rate, eluted with a gradient of 40 to 100% acetonitrile in 0.05% $HClO_4$ in water over 18 minutes), and after hydrolysis was determined to be complete, acetonitrile (110 mL) was charged to the reactor over 2 hours. The slurry was allowed to stir for an additional 2 hours, and the solids were isolated via vacuum filtration, followed by washing the wet cake with acetonitrile (2×10 mL). The residue was purified via reverse phase chromatography (Phenomenex® Luna® C18, 50×250 mm, 10 μm, 80 mL/minute flow rate, 25 mM ammonium acetate/acetonitrile, 64/36 isocratic), and the desired fractions were lyophilized to give the title compound as an acetate salt. MS (ESI) m/z 1357.5 $(M+H)^+$.

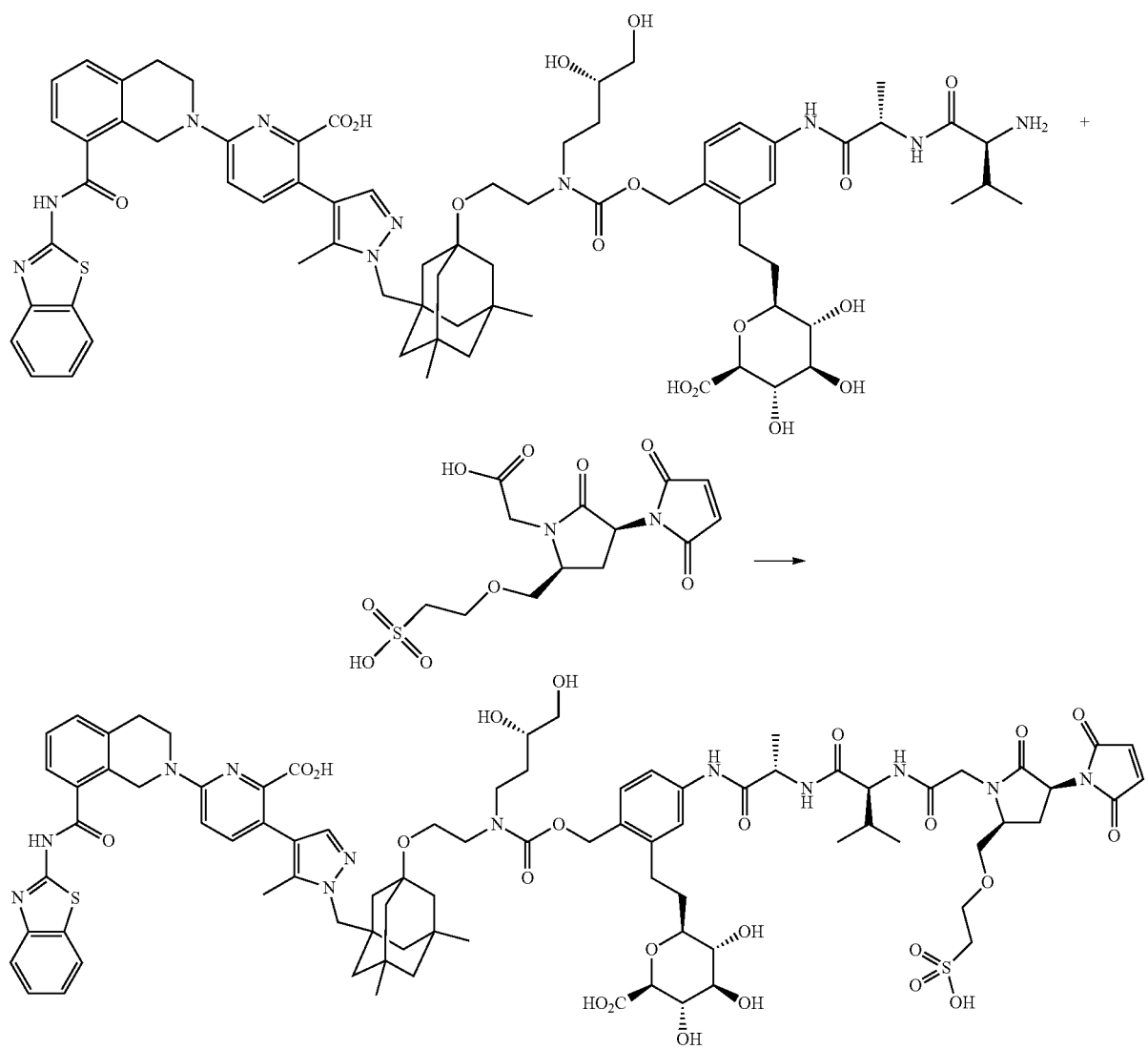

Example 1: 6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-(2-{(3S,5S)-3-(2,5-dioxo-2,5-dihydro-1H-pyrrol-1-yl)-2-oxo-5-[(2-sulfoethoxy)methyl]pyrrolidin-1-yl}acetamido)-3-methylbutanoyl]amino}propanoyl]amino}phenyl)methoxy]carbonyl}[(3S)-3,4-dihydroxybutyl]amino)ethoxy]-5,7-dimethyladamantan-1-yl}methyl)-5-methyl-1H-pyrazol-4-yl]pyridine-2-carboxylic acid (Synthon AAA)

Example 1.3.14 (17.7 mg) was dissolved in N,N-dimethylformamide (0.14 mL), and O-(7-azabenzotriazol-1-yl)-N,N,N',N'-tetramethyluronium hexafluorophosphate (16.9 mg) and N,N-diisopropylethylamine (18.5 µL) were added. The mixture was stirred for 3 minutes at room temperature and then added to a mixture of Example 1.4.1 (52.0 mg) and N,N-diisopropylethylamine (24.7 µL) in N,N-dimethylformamide (0.2 mL). After 1 hour, the reaction was diluted with N,N-dimethylformamide/water 1/1 (1.0 mL) and purified by reverse-phase HPLC (Phenomenex® Luna® C18 250×50 mm column), eluted with 5-75% acetonitrile in 0.1% trifluoroacetic acid/water (100 mL/minute), to provide the title compound. $^1$H NMR (500 MHz, dimethyl sulfoxide-d$_6$) δ ppm 9.86 (br d, 1H), 8.17 (br d, 1H), 8.04 (m, 2H), 7.78 (d, 1H), 7.61 (d, 1H), 7.51 (br d, 1H), 7.49-7.39 (m, 4H), 7.36 (m, 2H), 7.29 (s, 1H), 7.21 (d, 1H), 7.07 (s, 2H), 6.95 (d, 1H), 5.00 (s, 2H), 4.96 (s, 2H), 4.64 (t, 1H), 4.36 (m, 1H), 4.19 (m, 1H), 4.16 (d, 1H), 4.01 (d, 1H), 3.88 (br t, 2H), 3.82 (br m, 3H), 3.75 (br m, 1H), 3.64 (t, 2H), 3.54 (d, 2H), 3.47 (m, 4H), 3.43 (br m, 4H), 3.23 (br m, 5H), 3.13 (t, 1H), 3.10 (br m, 1H), 3.01 (br m, 2H), 2.93 (t, 1H), 2.83-2.68 (m, 3H), 2.37 (m, 1H), 2.08 (s, 3H), 1.99 (br m, 2H), 1.85 (m, 1H), 1.55 (br m, 1H), 1.37 (br m, 1H), 1.28 (br m, 6H), 1.10 (br m, 7H), 0.93 (br m, 1H), 0.88-0.69 (m, 12H); MS (ESI) m/z 1713.6 (M–H)$^-$.

Example 2: Preparation of AM2 Antibody

The amino acid sequence of the VH region for AM2 is provided in SEQ ID NO: 22. The amino acid sequence of the VL region for AM2 is provided in SEQ ID NO: 23. The heavy chain of AM2 is provided as SEQ ID NO: 1 and the light chain is provided as SEQ ID NO: 5.

The full-length nucleic acid sequences heavy and light chains of AM2 were expressed by transiently transfecting expression vectors encoded the heavy and light chains of AM2 in HEK293 cells. The amino acid sequence of the leader sequence used for expression of the heavy chain was MEFGLSWLFLVAILKGVQC (SEQ ID NO: 25) while the amino acid sequence used for expression of the light chain was MDMRVPAQLLGLLLLWFPGSRC (SEQ ID NO: 26). AM2, having a heavy chain of SEQ ID NO: 1 and a light chain of SEQ ID NO: 5, was subsequently purified for subsequent functional assessment.

Relative to anti-EGFR antibody AM2B, which comprises a heavy chain of SEQ ID NO: 21 and a light chain of SEQ ID NO: 24, amino acid mutations in AM2 represent (1) human IgG allotype changes from a z, non-a allotype to a z,a allotype; (2) a C6v1 (LC:C214A) mutation, enabling site-specific conjugation, and (3) a LALA mutation (two leucine to alanine substitutions, L234A, L235A).

Example 3: Conjugation of Synthon AAA with EGFR AM2 Antibody

A 10 mM solution of 2-(diphenylphosphino) benzoic acid (DPPBA, Sigma Aldrich) was prepared in dimethylacetamide (DMA). 2.42 equivalents of DPPBA was added to a solution of EGFR AM2 antibody pre-equilibrated at 4° C. (~10 mg/mL, formulated in 1× Dulbecco's phosphate-buffered saline (DPBS), pH 7.4 with 2 mM ethylenediaminetetraacetic acid (EDTA)). The reaction mixture was gently mixed and incubated at 4° C. for 16-24 hours. 3.7 Equivalents of 10 mM Synthon AAA (6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-(2-{(3S,5S)-3-(2,5-dioxo-2,5- dihydro-1H-pyrrol-1-yl)-2-oxo-5-[(2-sulfoethoxy)methyl]pyrrolidin-1-yl}acetamido)-3-methylbutanoyl]amino}propanoyl]amino}phenyl)methoxy]carbonyl}[(3S)-3,4-dihydroxybutyl]amino)ethoxy]-5,7-dimethyladamantan-1-yl}methyl)-5-methyl-1H-pyrazol-4-yl]pyridine-2-carboxylic acid (see U.S. Patent Application Publication No. 2019/0343961) (dissolved in DMA) was added into the reduced antibody solution and gently mixed. The reaction mixture was incubated at room temperature for 60 minutes, and subsequently quenched by 2 equivalents of N-acetyl-L-cysteine (NAC, Sigma Aldrich A-8199-10G). The antibody-drug conjugate (ADC) was purified by Hydrophobic Interaction Chromatography (HIC).

Example 4: EGFR-Targeted ADCs Inhibit the Growth of Cancer Cells In Vivo

The NSCLC cell lines, EBC-1 and NCI-H441 (called H441 hereafter) were obtained from JCRB and ATCC, respectively. Cells were maintained in monolayer culture for at most 3 passages according to recommendations of the supplier. A suspension of 5×10$^6$ cells in culture medium mixed with Matrigel (1:1, volume:volume) was injected subcutaneously in the right flank of female SCID/beige mice. Treatment started when the sizes of the flank tumors were approximately 200 mm$^3$.

| Antibody Heavy Chain (SEQ ID NO) | Antibody Light Chain (SEQ ID NO) | Synthon | Average DAR | DAR Method |
|---|---|---|---|---|
| AM2B-AAA | 21 | 24 | AAA | 2 | HIC |
| AM7-AAA | 9 | 11 | AAA | 2 | HIC |

Average DAR represents the average number of drugs coupled to the antibodies for the composition.

FIG. 3 shows AM2B-AAA and AM7-AAA inhibited growth of human NSCLC grown as xenografts in immune-compromised mice. Moderate growth inhibition was observed after administration of the ADCs as single agent. Durability of the inhibition caused by docetaxel (DTX) increased after coadministration with either AM2B-AAA or AM7-AAA. The activity of ADCs was compared to a non-targeting IgG antibody (AB095) (a human IgG1 antibody recognizing tetanus toxoid; see Larrick et al, 1992, Immunological Reviews 69-85).

FIGS. 3A and 3B show changes of tumor volume following treatment of the papillary adenocarcinoma, H441.

FIGS. 3C and 3D show changes of tumor volume following treatment of the squamous carcinoma, EBC-1.

Each point of the curve represents the mean volume of 8 tumors.

Error bars depict the standard error of the mean.

Example 5: FACS Analysis AM2-AAA Inhibits Bcl-xL in Cells Overexpressing EGFR To assay binding of AM2-AAA to cell surface overexpressed wt EGFR and to mutant forms of EGFR including the activating mutations found in NSCLC (mutEGFR), tumor cells overexpressing wt EGFR (A431) and mutEGFR (NCI-H1650) were assessed by fluorescence activated cell sorting (FACS).

Cells were harvested from flasks when at approximately 1.5×10$^6$ cells/mL. Cells were washed once in PBS/1% FBS (FACS buffer) then resuspended at 2.5×10$^6$ cells/mL in FACS buffer. 50 μL of cells were added to a round bottom 96-well plate. 50 μL of a 2× concentration of mAb/ADC (final concentrations are indicated in the figures) was added to wells and the plate was incubated at 4° C. for one hour. The cells were washed twice in FACS buffer and resuspended in 50 μL of a 1:100 dilution of secondary Ab (AlexaFluor 488, Invitrogen, 11013) diluted in FACS buffer. The plate was incubated at 4° C. for one hour and washed twice with FACS buffer. Cells were resuspended in 100 μL of PBS/1% formaldehyde and analyzed on a Becton Dickinson FACSCanto™ (fluidics system) II flow cytometer. Data was analyzed using WinList flow cytometry analysis software.

| | Antibody Heavy Chain (SEQ ID NO) | Antibody Light Chain (SEQ ID NO) | Synthon | Average DAR | DAR Method |
|---|---|---|---|---|---|
| AM2 | 1 | 5 | — | — | — |
| AM2-AAA | 1 | 5 | AAA | 2 | HIC |
| MSL109 hIgG | 29 | 30 | — | — | — |

AM2-AAA and AM2 were shown to bind to both cell lines with similar apparent affinity, indicating no impact of the linker drug on Ab binding properties. No binding was observed using a non-binding control MSL109 hIgG (FIG.

1). Monoclonal antibody to CMV glycoprotein H (MSL109) is a non-targeting control that has a heavy chain set forth as SEQ ID NO: 29 and a light chain as set forth as SEQ ID NO: 30.

Example 6: BIM-Bcl-xL Complex Disruption Assay

To assess if treatment of cells with AM2-AAA inhibited Bcl-xL in an EGFR-dependent manner, disruption of Bcl-xL-BIM complexes in both wt EGFR and mutEGFR expressing cell lines was assessed.

Cells were plated at 50×10³ cells/well in 96-well plates in growth media RPMI-1640 (GibcoInvitrogen, 22400-089) supplemented with 10% fetal bovine serum in the morning. In the afternoon, treatments were added in fresh media to triplicate wells. Twenty-four hours later, cells were lysed with 10 mM HEPES, 150 mM NaCl, 1% CHAPS buffer and Bcl-xL/BIM complexes in protein lysates were captured on plates (MesoScale Diagnostics LLC, L15SA-1) previously coated with anti-Bcl-xL capture antibody (R&D systems, biotinylated anti-Bcl-xL 840768, DYC894-2 kit). Plates were washed with PBS and detection antibody anti-BIM (Cell Signaling, 2933) was added to wells for one hour at room temperature. Plates were then washed with PBS and Sulfo-tagged anti rabbit antibody (MesoScale Diagnostics LLC, R32AB-1) was added to wells, and then incubated at room temperature for one hour. Plates were washed and MSD read buffer (MesoScale Diagnostics LLC, R92TC-2) was added to wells and plates were read on MesoScale Diagnostics LLC instrument (Sector S 600). Data was plotted as percent remaining BIM/BCL-xL complex. (FIG. 2)

Example 7: Caspase Assay

| | Antibody Heavy Chain (SEQ ID NO) | Antibody Light Chain (SEQ ID NO) | Synthon | Average DAR | DAR Method |
|---|---|---|---|---|---|
| AM2 | 1 | 5 | — | — | — |
| AM2-AAA | 1 | 5 | AAA | 2 | HIC |
| MSL109 hIgG-AAA | 29 | 30 | AAA | 1.6 | MS |

A431 cells were plated at 50,000 cells per well in 96 well plates (Costar, 3610) in growth media. After 24 hours in culture at 37° C., ADCs were added to wells and incubated at 37° C. in a CO₂ incubator for 24 hours. After incubation, 100 μL of Caspase-Glo® (caspase luminescent assay) 3/7 Assay reagent (Promega, G8093) was added to each well and shaken for 10 minutes. Plates were then incubated at 37° C. for 20 minutes. Caspase 3/7 activity was assessed using a Victor luminescence plate reader (Perkin Elmer).

While a non-targeting ADC (MSL109 hIgG-AAA) or AM2 failed to disrupt Bcl-xL-BIM complexes, AM2-AAA treatment resulted in efficient complex disruption in both cell lines. These results indicate that the AAA warhead was specifically delivered via AM2-AAA to EGFR expressing cells (See FIG. 2) and inhibited Bcl-xL activity.

The ability of AM2-AAA to promote caspase activation, a downstream consequence of Bcl-xL inhibition, was also assessed in the A-431 cells. AM2-AAA, but not AM2 or the non-targeting MSL109 hIgG-AAA induced caspase activation supporting EGFR-dependent on mechanism activity of the targeted ADC.

Example 8: Toxicity Study

| | Antibody Heavy Chain (SEQ ID NO) | Antibody Light Chain (SEQ ID NO) | Synthon | Average DAR | DAR method |
|---|---|---|---|---|---|
| AM2B-AAA | 21 | 24 | AAA | 1.97 | HIC |
| AM2-AAA | 1 | 5 | AAA | 2 | MS |

Study A: Four week toxicity study of two intravenous doses (once every three weeks) of AM2B-AAA in cynomolgus monkeys Two intravenous administrations of AM2B-AAA were administered to male and female cynomolgus monkeys in four groups: control (0 mg/kg/dose), dose A (low; X mg/kg/dose), dose B (mid; 3× mg/kg/dose), and dose C (high; 6× mg/kg/dose). Administration of AM2B-AAA resulted in adverse findings in the arteries of multiple organs at the high dose (dose C). Inflammation, artery (minimal to moderate) at Dose C, with positive immunohistochemical staining for human IgG and complement, consistent with immune complex disease secondary to administration of foreign protein, was observed. This was interpreted as secondary to immune complex formation and deposition with fixation of complement, as demonstrated by immunohistochemistry. Non-adverse findings attributed to AB2B-AAA included increased glomerular matrix in the kidney at all dose levels.

Noteworthy test item-related changes considered not adverse due to low magnitude and absence of functional effect included kidney [increase, glomerular matrix (minimal to mild) at ≥Dose A); dilation, tubules (minimal) at ≥Dose B]. RBC mass (decrease; minimal at ≥Dose B); platelet count (decrease; mild to moderate at ≥Dose B); acute phase inflammatory response characterized by globulin (minimal increase at Dose A and Dose B; mild to moderate increase at Dose C), CRP (mild increase at Dose C), albumin (minimal to mild decrease at ≥Dose B), and fibrinogen (minimal increase at ≥Dose B).

Study B: A five-week (two dose; Q3W) intravenous exploratory toxicity study of AM2-AAA in cynomolgus monkeys Two intravenous administrations of AM2-AAA were administered to male and female cynomolgus monkeys at 0 mg/kg/dose (control), Dose 1 (6× mg/kg/dose, where X is the same as in Study A), and Dose 2 (15× mg/kg/dose). There was no finding of immune complex disease detected.

Kidney findings consisted of mild to moderate increases in glomerular matrix with accompanying mild increases in urea nitrogen at ≥Dose 1. Hematology findings included test-item related mild to moderate decreases in RBC mass, non-adverse reticulocyte decreases, and moderate to marked platelet decreases at ≥Dose 1 (considered adverse only at Dose 2). Other test item-related changes considered not adverse included mildly to moderately decreased number of lymphocytes in the thymus at ≥Dose 1, minimally to mildly increased AST activity at ≥Dose 1, increased bilirubin at Dose 1, mildly to moderately decreased calcium at ≥Dose 1, and minimally to mildly decreased albumin at ≥Dose 1.

Example 9: Biacore Binding Analysis of AM2 and AM2-AAA

Biacore analysis was performed to compare the affinity of the AM2 antibody and the AM2-AAA ADC to three forms of recombinant EGFR, specifically the wild-type EGFR extra-cellular domain (ECD) (EGFR(h)(1-645)), EGFRvIII (EGFR(h)(1-29)-G-(298-645)) and a truncated wild-type EGFR1-525 (EGFR1(h)(1-525)). AM2 includes the heavy and light chain amino acid sequences of AM2 as provided in SEQ ID NOs: 1 and 5, respectively, and was made according to standard methods. AM2-AAA comprises the AM2 antibody having the heavy and light chain amino acid sequences provided in SEQ ID NOs: 1 and 5, respectively, conjugated to the AAA synthon (average DAR 2).

Binding kinetics for AM2 and AM2-AAA for recombinant soluble EGFR extracellular domains (ECDs) were determined by surface plasmon resonance-based measurements made on a Biacore T200 instrument (GE Healthcare) at 25° C. using an anti-Fc capture assay approach. Recombinant soluble ECDs for the three isoforms of EGFR were expressed from transiently transfected HEK293 cells as secreted proteins with a C-terminal myc and histidine tag, and purified by Ni-IMAC (immobilized metal affinity chromatography) and SEC. In particular, the EGFR ECD tested included amino acids 1-645 of EGFR fused to a myc and histidine tag [(EGFR (1-645)-LESRGPF-Myc-NMHTG-6His ("LESRGPF" (SEQ ID NO: 27))]. The EGFRvIII variant was also fused to a myc and histidine tag (EGFR(h)(1-29)-G-(298-645)-LESRGPF-Myc-NMHTG-6His (SEQ ID NO: 31)), as was the ECD EGFR1-525 [EGFR1(h)(1-525)]-LESRGPF-Myc-NMHTG-6His ("LESRGPF" (SEQ ID NO: 28))]. All ECDs were expressed with the signal sequence MRPSGTAGAALLALLAALCPASRA (SEQ ID NO: 32) which was cleaved during secretion.

Chip preparation and binding kinetic measurements were made in the assay buffer HBS-EP+ (10 mM Hepes, pH 7.4, 150 mM NaCl, 3 mM EDTA, 0.05% Tween 20). For anti-Fc capture chip preparation, approximately 2000 RU of goat anti-human IgG Fc polyclonal antibody (Thermo Fisher Scientific Inc., cat. 31125), diluted to 25 µg/mL in 10 mM sodium acetate (pH 4.5) was directly immobilized across a CM5 biosensor chip using a standard amine coupling kit according to manufacturer's instructions and procedures (GE Healthcare). Unreacted moieties on the biosensor surface were blocked with ethanolamine. For binding kinetics measurements each assay cycle consisted of the following steps: (1) capture of test antibody on test surface only; (2) analyte injection (EGFR ECD or buffer only) over both reference and test surface (240 µL at 80 µl/min), after which the dissociation was monitored for 900 seconds at 80 µl/min; (3) regeneration of the capture surface by 10 mM Glycine-HCl, pH 1.5 injections over both reference and test surface.

For kinetic determinations, analytes were randomized 3-fold dilution series from 3 uM top dose. During the assay, all measurements were referenced against the capture surface alone (i.e., with no captured test antibody) and buffer-only injections were used for secondary referencing. Data were processed and fitted globally to a 1:1 binding model using Biacore T200 Evaluation software to determine the binding kinetic rate constants, $k_a$ $(M^{-1}s^{-1})$ and $k_d$ $(s^{-1})$, and the equilibrium dissociation constant $K_D(M)$. Results of the Biacore analysis are shown in Table 1.

TABLE 1

Binding Kinetics of AM2 Antibody and AM2-AAA ADC

| | EGFRvIII (hEGFR de2-7) [EGFR(H)(1-29)-G-(298-645)] | | | EGFRs1-501 (EGFR(1-525)) [EGFR1(h)(1-525)] | | | hEGFR WT [EGFR(1-645)] | | |
|---|---|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | $k_a$ (1/Ms) | $k_d$ (1/s) | $K_D$ (M) |
| AM2 | $3.3 \times 10^4$ | $1.7 \times 10^{-4}$ | $5.0 \times 10^{-9}$ | $2.8 \times 10^3$ | $1.2 \times 10^{-3}$ | $4.2 \times 10^{-7}$ | No observable binding (at 3 µM top dose) | | |
| AM2-AAA | $3.5 \times 10^4$ | $1.7 \times 10^{-4}$ | $4.9 \times 10^{-9}$ | $2.9 \times 10^3$ | $1.2 \times 10^{-3}$ | $4.0 \times 10^{-7}$ | No observable binding (at 3 µM top dose) | | |

While various specific embodiments have been illustrated and described, it will be appreciated that various changes can be made without departing from the spirit and scope of the disclosure.

TABLE 2

Sequence Table

| SEQ ID NO | Clone | Protein Region | V Region |
|---|---|---|---|
| 1 | AM2 | Heavy Chain | EVQLQESGPGLVKPSQTLSLTCTVSGYSISNDFAWNWIRQPPG KGLEWMGYISYKGNTRYQPSLKSRITISRDTSKNQFFLKLNSV TAADTATYYCVTASRGFPWWGQGTLVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVDK KVEPKS<u>C</u>DKTHTCPPCPAPEAAGGPSVFLFPPKPKDTLMISRT PEVTCVVVDVSHEDPEVKFNWYVDGVEVHNAKTKPREEQY NSTYRVVSVLTVLHQDWLNGKEYKCKVSNKALPAPIEKTISK AKGQPREPQVYTLPPS*RDELT*KNQVSLTCLVKGFYPSDIAVE WESNGQPENNYKTTPPVLDSDGSFFLYSKLTVDKSRWQQGN VFSCSVMHEALHNHYTQKSLSLSPGK |

TABLE 2-continued

Sequence Table

| SEQ ID NO | Clone | Protein Region | V Region |
|---|---|---|---|
| 2 | AM2 | HC CDR1 | GYSISNDFAWN |
| 3 | AM2 | HC CDR2 | YISYKGNTRYQPSLKS |
| 4 | AM2 | HC CDR3 | ASRGFPW |
| 5 | AM2 Light Chain | | DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEA |
| 6 | AM2 | LC CDR1 | HSSQDINSNIG |
| 7 | AM2 | LC CDR2 | HGTNLDD |
| 8 | AM2 | LC CDR3 | VQYAQFPWT |
| 9 | AM7 Heavy Chain | | EVQLQESGPGLVKPSQTLSLTCTVSGYSISNDFAWNWIRQLPGKGLEWMGYISYKGNTRYQPSLKSRITISRDTSKNQFFLKLNSVTAADTATYYCVTASRGLPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 2 | AM7 | HC CDR1 | GYSISNDFAWN |
| 3 | AM7 | HC CDR2 | YISYKGNTRYQPSLKS |
| 10 | AM7 | HC CDR3 | ASRGLPY |
| 11 | AM7 Light Chain | | DIQMTQSPSSMSVSVGDRVTITCHSSQDITYNIGWLQQKPGKSFKGLIYHGANLDDGVPSRFSGSGSGTDYTLTISSLQPEDFATYYCVQYDEFPWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEA |
| 12 | AM7 | LC CDR1 | HSSQDITYNIG |
| 13 | AM7 | LC CDR2 | HGANLDD |
| 14 | AM7 | LC CDR3 | VQYDEFPWT |
| 15 | wild type human EGFR | | MRPSGTAGAALLALLAALCPASRALEEKKVCQGTSNKLTQLGTFEDHFLSLQRMFNNCEVVLGNLEITYVQRNYDLSFLKTIQEVAGYVLIALNTVERIPLENLQIIRGNMYYENSYALAVLSNYDANKTGLKELPMRNLQEILHGAVRFSNNPALCNVESIQWRDIVSSDFLSNMSMDFQNHLGSCQKCDPSCPNGSCWGAGEENCQKLTKIICAQQCSGRCRGKSPSDCCHNQCAAGCTGPRESDCLVCRKFRDEATCKDTCPPLMLYNPTTYQMDVNPEGKYSFGATCVKKCPRNYVVTDHGSCVRACGADSYEMEEDGVRKCKKCEGPCRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFMRRRHIVRKRTLRRLLQERELVEPLTPSGEAPNQALLRILKETEFKKIKVLGSGAFGTVYKGLWIPEGEKVKIPVAIKELREATSPKANKEILDEAYVMASVDNPHVCRLLGICLTSTVQLITQLMPFGCLLDYVREHKDNIGSQYLLNWCVQIAKGMNYLEDRRLVHRDLAARNVLVKTP |

TABLE 2-continued

Sequence Table

| SEQ ID NO | Clone | Protein Region | V Region |
|---|---|---|---|
| | | | QHVKITDFGLAKLLGAEEKEYHAEGGKVPIKWMALESI LHRIYTHQSDVWSYGVTVWELMTFGSKPYDGIPASEISS ILEKGERLPQPPICTIDVYMIMVKCWMIDADSRPKFRELI IEFSKMARDPQRYLVIQGDERMHLSPTDSNFYRALMD EEDMDDVVDADEYLIPQQGFFSSPSTSRTPLLSSLSATSN NSTVACIDRNGLQSCPIKEDSFLQRYSSDPTGALTEDSID DTFLPVPEYINQSVPKRPAGSVQNPVYHNQPLNPAPSRD PHYQDPHSTAVGNPEYLNTVQPTCVNSTFDSPAHWAQ KGSHQISLDNPDYQQDFFPKEAKPNGIFKGSTAENAEYL RVAPQSSEFIGA |
| 16 | truncated wild type ECD of the EGFR (EGFR (1-525)) | | MRPSGTAGAALLALLAALCPASRALEEKKVCQGTSNKLT QLGTFEDHFLSLQRMFNNCEVVLGNLEITYVQRNYDLSFL KTIQEVAGYVLIALNTVERIPLENLQIIRGNMYYENSYALA VLSNYDANKTGLKELPMRNLQEILHGAVRFSNNPALCNV ESIQWRDIVSSDFLSNMSMDFQNHLGSCQKCDPSCPNGSC WGAGEENCQKLTKIICAQQCSGRCRGKSPSDCCHNQCAA GCTGPRESDCLVCRKFRDEATCKDTCPPLMLYNPTTYQM DVNPEGKYSFGATCVKKCPRNYVVTDHGSCVRACGADSY EMEEDGVRKCKKCEGPCRKVCNGIGIGEFKDSLSINATNI KHFKNCTSISGDLHILPVAFRGDSFTHTPPLDPQELDILKT VKEITGFLLIQAWPENRTDLHAFENLEIIRGRTKQHGQFS LAVVSLNITSLGLRSLKEISDGDVIISGNKNLCYANTINWK KLFGTSGQKTKIISNRGENSCKATGQVCHALCSPEGCWG PEPRDCVS |
| 17 | ECD of human EGFR | | MRPSGTAGAA LLALLAALCP ASRALEEKKV CQGTSNKLTQ LGTFEDHFLS LQRMFNNCEV VLGNLEITYV QRNYDLSFLK TIQEVAGYVL IALNTVERIP LENLQIIRGN MYYENSYALA VLSNYDANKT GLKELPMRNL QEILHGAVRF SNNPALCNVE SIQWRDIVSS DFLSNMSMDF QNHLGSCQKC DPSCPNGSCW GAGEENCQKL TKIICAQQCS GRCRGKSPSD CCHNQCAAGC TGPRESDCLV CRKFRDEATC KDTCPPLMLY NPTTYQMDVN PEGKYSFGAT CVKKCPRNYV VTDHGSCVRACGADSYEMEE DGVRKCKKCEGPCRKVCNGI GIGEFKDSLS INATNIKHFK NCTSISGDLH ILPVAFRGDS FTHTPPLDPQ ELDILKTVKE ITGFLLIQAW PENRTDLHAF ENLEIIRGRT KQHGQFSLAV VSLNITSLGL RSLKEISDGD VIISGNKNLC YANTINWKKL FGTSGQKTKI ISNRGENSCK ATGQVCHALC SPEGCWGPEP RDCVSCRNVS RGRECVDKCN LLEGEPREFV ENSECIQCHP ECLPQAMNIT CTGRGPDNCI QCAHYIDGPH CVKTCPAGVM GENNTLVWKY ADAGHVCHLC HPNCTYGCTG PGLEGCPTNG PKIPS |
| 18 | EGFRvIII | | <u>MRPSGTAGAALLALLAALCPASRA</u>LEEKKGNYVVTDHGSC VRACGADSYEMEEDGVRKCKKCEGPCRKVCNGIGIGEFK DSLSINATNIKHFKNCTSISGDLHILPVAFRGDSFTHTPPLD PQELDILKTVKEITGFLLIQAWPENRTDLHAFENLEIIRGR TKQHGQFSLAVVSLNITSLGLRSLKEISDGDVIISGNKNLC YANTINWKKLFGTSGQKTKIISNRGENSCKATGQVCHAL CSPEGCWGPEPRDCVSCRNVSRGRECVDKCNLLEGEPRE FVENSECIQCHPECLPQAMNITCTGRGPDNCIQCAHYIDG PHCVKTCPAGVMGENNTLVWKYADAGHVCHLCHPNCT YGCTGPGLEGCPTNGPKIPSIATGMVGALLLLLVVALGIGLF MRRRHIVRKRTLRRLLQERELVEPLTPSGEAPNQALLRILKET EFKKIKVLGSGAFGTVYKGLWIPEGEKVKIPVAIKELREATSP KANKEILDEAYVMASVDNPHVCRLLGICLTSTVQLITQLMPF GCLLDYVREHKDNIGSQYLLNWCVQIAKGMNYLEDRRLVH RDLAARNVLVKTPQHVKITDFGLAKLLGAEEKEYHAEGGKV PIKWMALESILHRIYTHQSDVWSYGVTVWELMTFGSKPYDGI PASEISSILEKGERLPQPPICTIDVYMIMVKCWMIDADSRPKFR ELIIEFSKMARDPQRYLVIQGDERMHLSPTDSNFYRALMDEE DMDDVVDADEYLIPQQGFFSSPSTSRTPLLSSLSATSNNSTVA CIDRNGLQSCPIKEDSFLQRYSSDPTGALTEDSIDDTFLPVPEY INQSVPKRPAGSVQNPVYHNQPLNPAPSRDPHYQDPHSTAVG NPEYLNTVQPTCVNSTFDSPAHWAQKGSHQISLDNPDYQQD FFPKEAKPNGIFKGSTAENAEYLRVAPQSSEFIGA |
| 19 | EGFRvIII ECD | | LEEKKGNYVVTDHGSCVRACGADSYEMEEDGVRKCKKC EGPCRKVCNGIGIGEFKDSLSINATNIKHFKNCTSISGDLHI LPVAFRGDSFTHTPPLDPQELDILKTVKEITGFLLIQAWPE NRTDLHAFENLEIIRGRTKQHGQFSLAVVSLNITSLGLRSL KEISDGDVIISGNKNLCYANTINWKKLFGTSGQKTKIISNR GENSCKATGQVCHALCSPEGCWGPEPRDCVSCRNVSRGR |

TABLE 2-continued

Sequence Table

| SEQ ID NO | Clone | Protein Region | V Region |
|---|---|---|---|
| | | | ECVDKCNLLEGEPREFVENSECIQCHPECLPQAMNITCTG RGPDNCIQCAHYIDGPHCVKTCPAGVMGENNTLVWKYA DAGHVCHLCHPNCTYGCTGPGLEGCPTNGP |
| 20 | Binding epitope (amino acid residues 287-302 of the mature form of hEGFR) | | CGADSYEMEEDGVRKC |
| 21 | AM2B Heavy Chain | | EVQLQESGPGLVKPSQTLSLTCTVGYSISNDFAWNWIRQPPG KGLEWMGYISYKGNTRYQPSLKSRITISRDTSKNQFFLKLNSV TAADTATYYCVTASRGFPWWGQGTLVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYN STYRVVSVLTVLHQDWLNGKEYKCKVSNKALPAPIEKTISKA KGQPREPQVYTLPPSREEMTKNQVSLTCLVKGFYPSDIAVEW ESNGQPENNYKTTPPVLDSDGSFFLYSKLTVDKSRWQQGNV FSCSVMHEALHNHYTQKSLSLSPGK |
| 2 | AM2B/ AM2 HC CDR1 | CDR1 | GYSISNDFAWN |
| 3 | AM2B/ AM2 HC CDR2 | CDR2 | YISYKGNTRYQPSLKS |
| 4 | AM2B/ AM2 HC CDR3 | CDR3 | ASRGFPW |
| 22 | AM2/ AM2B VH | | EVQLQESGPGLVKPSQTLSLTCTVGYSISNDFAWNWIRQPPG KGLEWMGYISYKGNTRYQPSLKSRITISRDTSKNQFFLKLNSV TAADTATYYCVTASRGFPWWGQGTLVTVSS |
| 23 | AM2/ AM2B VL | | DIQMTQSPSSMSVSVGDRVTITCHSSQDINSNIGWLQQKPGK SFKGLIYHGTNLDDGVPSRFSGSGSGTDYTLTISSLQPEDFAT YYCVQYAQFPWTFGGGTKLEIK |
| 24 | AM2B Light Chain | | DIQMTQSPSSMSVSVGDRVTITCHSSQDINSNIGWLQQKPGK SFKGLIYHGTNLDDGVPSRFSGSGSGTDYTLTISSLQPEDFAT YYCVQYAQFPWTFGGGTKLEIKRTVAAPSVFIFPPSDEQLKSG TASVVCLLNNFYPREAKVQWKVDNALQSGNSQESVTEQDSK DSTYSLSSTLTLSKADYEKHKVYACEVTHQGLSSPVTKSFNR GEC |
| 6 | AM2B/ AM2 LCDR1 | CDR1 | HSSQDINSNIG |
| 7 | AM2B/ AM2 LCDR2 | CDR2 | HGTNLDD |
| 8 | AM2B/ AM2 LCDR3 | CDR3 | VQYAQFPWT |
| 29 | MSL109 hIgG1 Heavy Chain | Heavy Chain | EEQVLESGGGLVKPGGSLRLSCAASGFTFSPYSVFWVRQAPG KGLEWVSSINSDSTYKYYADSVKGRFTISRDNAENSIFLQMN SLRAEDTAVYYCARDRSYYAFSSGSLSDYYYGLDVWGQGTT VIVSSASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGPS VFLFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSREEMTKNQVS |

TABLE 2-continued

Sequence Table

| SEQ ID NO | Clone | Protein Region | V Region |
|---|---|---|---|
| | | | LTCLVKGFYPSDIAVEWESNGQPENNYKTTPPVLDSDGSFFL YSKLTVDKSRWQQGNVFSCSVMHEALHNHYTQKSLSLSPGK |
| 30 | MSL109 light chain | Light Chain | DIVMTQSPLSLSVTPGEPASISCRSSQSLLHTNGYNYLDWYVQ KPGQSPQLLIYLASNRASGVPDRFSGSGSGTDFTLKISRVETE DVGVYYCMQALQIPRTFGQGTKVEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVTK SFNRGEC |

We claim:

1. An anti-human epidermal growth factor receptor (hEGFR) antibody-drug conjugate comprising the following structure:

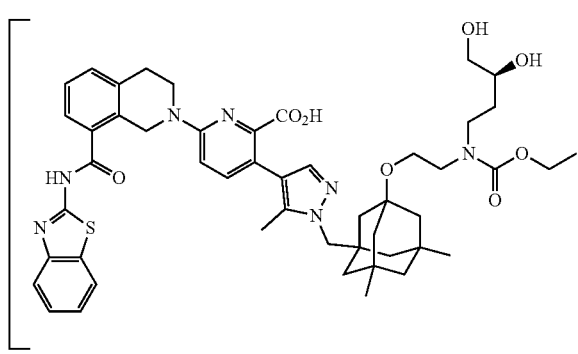

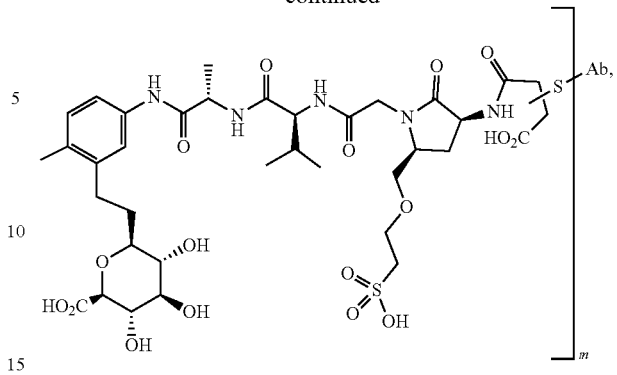

wherein Ab is an IgG1 anti-hEGFR antibody comprising a heavy chain comprising the amino acid sequence set forth as SEQ ID NO: 1 and a light chain comprising the amino acid sequence set forth as SEQ ID NO: 5; and wherein m is 2.

2. The antibody-drug conjugate of claim 1, wherein the structure of formula (I) is conjugated to antibody Ab through C220 of the heavy chain.

3. The ADC of claim 1, comprising the structure of formula (II):

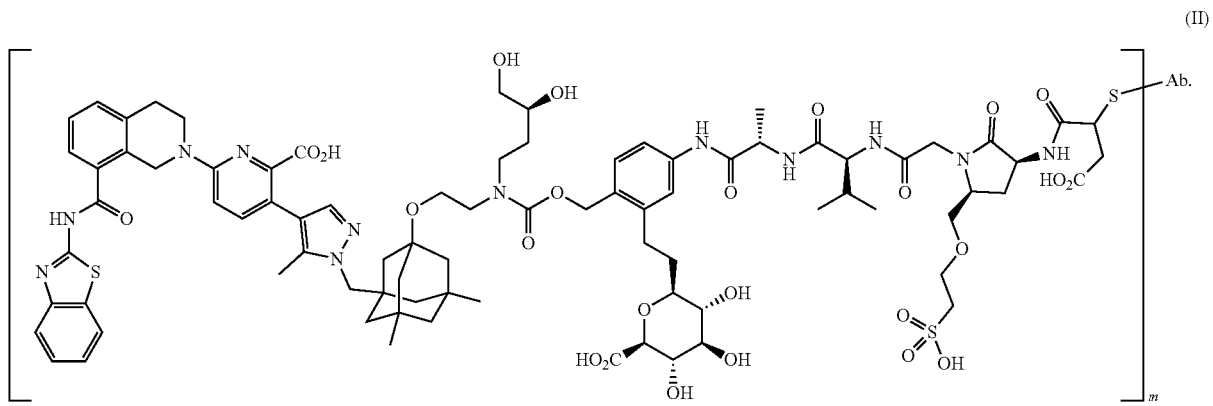

* * * * *

UNITED STATES PATENT AND TRADEMARK OFFICE
CERTIFICATE OF CORRECTION

PATENT NO. : 11,759,527 B2
APPLICATION NO. : 17/580134
DATED : September 19, 2023
INVENTOR(S) : Erwin R. Boghaert et al.

It is certified that error appears in the above-identified patent and that said Letters Patent is hereby corrected as shown below:

On the Title Page

On page 4, in Column 1, item (56), under FOREIGN PATENT DOCUMENTS, Line 49, delete "A61K 47/65" and insert -- A61K47/65 --, therefor.

On page 4, in Column 2, item (56), under OTHER PUBLICATIONS, Line 9, delete "forthe" and insert -- for the --, therefor.

On page 4, in Column 2, item (56), under OTHER PUBLICATIONS, Line 40, delete "forthe" and insert -- for the --, therefor.

On page 5, in Column 2, item (56), under OTHER PUBLICATIONS, Line 17, delete ""Self-lmmolative Dendrimers," and insert -- "Self-Immolative Dendrimers," --, therefor.

On page 5, in Column 2, item (56), under OTHER PUBLICATIONS, Line 50, delete "ReceptorChimeric" and insert -- Receptor Chimeric --, therefor.

On page 6, in Column 1, item (56), under OTHER PUBLICATIONS, Line 7, delete "Biologies," and insert -- Biologics, --, therefor.

On page 7, in Column 2, item (56), under OTHER PUBLICATIONS, Line 22, delete "("TBDPSA"):" and insert -- ("TBDPSE"): --, therefor.

On page 8, in Column 2, item (56), under OTHER PUBLICATIONS, Line 26, delete "Jeffrey S.C et al.," and insert -- Jeffrey S.C. et al., --, therefor.

On page 11, in Column 1, item (56), under OTHER PUBLICATIONS, Line 35, delete ""ChimericAntibodies,"" and insert -- "Chimeric Antibodies," --, therefor.

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 11,759,527 B2

On page 11, in Column 2, item (56), under OTHER PUBLICATIONS, Line 11, delete "Streptomyces griseoluteus,"" and insert -- Streptomyces Griseoluteus," --, therefor.

On page 13, in Column 1, item (56), under OTHER PUBLICATIONS, Line 17, delete "EGFr_Human," and insert -- EGFR_Human --, therefor.

In the Specification

In Column 15, Line 11, delete "5- trihy-" and insert -- 5-trihy- --, therefor.

In Column 19, Line 1, delete "1X10$^{-6}$" and insert -- 1x10$^{-10}$ --, therefor.

In Column 19, Line 6, delete "6X10-9" and insert -- 6x10$^{-9}$ --, therefor.

In Column 19, Line 7, delete "5.5X10-9" and insert -- 5.5x10$^{-9}$ --, therefor.

In Column 19, Line 7, delete "5.0X10-9" and insert -- 5.0x10$^{-9}$ --, therefor.

In Column 20, Line 9, delete "ChemDraw©" and insert -- ChemDraw® --, therefor.

In Column 35, Line 62, delete "6-tetramnethylpiperidin-" and insert -- 6-tetramethylpiperidin- --, therefor.